(12) United States Patent
Haruta et al.

(10) Patent No.: US 6,174,887 B1
(45) Date of Patent: Jan. 16, 2001

(54) AMIDE COMPOUNDS AND USE OF THE SAME

(75) Inventors: Junichi Haruta; Kazuhiko Sakuma; Yoshihiro Watanabe, all of Takatsuki (JP)

(73) Assignee: Japan Tobacco Inc., Tokyo (JP)

( * ) Notice: Under 35 U.S.C. 154(b), the term of this patent shall be extended for 0 days.

(21) Appl. No.: 09/011,983

(22) PCT Filed: Aug. 15, 1996

(86) PCT No.: PCT/JP96/02305

§ 371 Date: Feb. 20, 1998

§ 102(e) Date: Feb. 20, 1998

(87) PCT Pub. No.: WO97/08133

PCT Pub. Date: Mar. 6, 1997

(30) Foreign Application Priority Data

Aug. 22, 1995 (JP) .................................................... 7-213855

(51) Int. Cl.[7] ...................... A61K 31/166; C07C 237/28; C07C 237/32; C07C 237/34
(52) U.S. Cl. ..................... 514/252.12; 514/331; 514/364; 514/395; 514/539; 514/542; 514/563; 544/400; 546/234; 548/131; 548/221; 560/39; 560/40; 562/444; 562/445
(58) Field of Search ............................. 544/400; 546/234; 548/131, 221; 560/39, 40; 562/444, 445; 514/255, 331, 364, 395, 539, 542, 563, 252.12

(56) References Cited

FOREIGN PATENT DOCUMENTS

| 48-18241 | * 3/1973 | (JP) . |
| 63-138051 | * 10/1988 | (JP) . |
| 63-239256 | * 10/1988 | (JP) . |

* cited by examiner

*Primary Examiner*—Richard L. Raymond
(74) *Attorney, Agent, or Firm*—Foley & Lardner

(57) ABSTRACT

An amide compound of the formula (I):

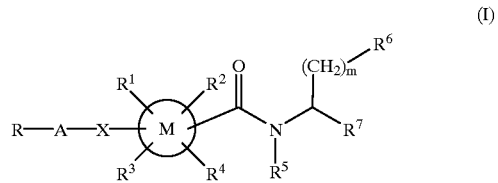

wherein R is amino and the like, A is alkylene and the like, X is O, S and the like, M is arylene and the like, $R^1$, $R^2$, $R^3$ and $R^4$ are H, hydroxy and the like, $R^5$ is H, alkyl and the like, m is an integer of 0-6, $R^6$ is an optionally substituted aryl and the like, and $R^7$ is H, an optionally substituted alkyl and the like, a pharmaceutically acceptable acid addition salt thereof and a pharmaceutical containing same as an active ingredient. The amide compounds exhibit superior suppressive effects on cytokines directly or indirectly involved in inflammations, such as IL-8, IL-1, IL-6, TNF-α, GM-CSF and the like, and are useful for the prophylaxis and treatment of rheumatic diseases, arthritis due to gout and the like.

9 Claims, No Drawings

AMIDE COMPOUNDS AND USE OF THE SAME

This application is a 371 of PCT/JP96/02305, filed Aug. 15, 1996.

TECHNICAL FIELD

The present invention relates to a novel compound exhibiting superior suppressive effects on cytokines directly or indirectly involved in inflammations, such as interleukin-8 (IL-8), interleukin-1 (IL-1), interleukin-6 (IL-6), tumor necrosis factor (TNF-$\alpha$), GM-CSF and the like, and pharmaceutical agents comprising said compound, such as anti-inflammatory agents.

BACKGROUND ART

An inflammation is one of the protective responses in the living organisms which aims at removal of foreign substances, pathogenic bacteria and so on, as well as repair of damaged tissues. When inflammatory stimulation is received, the microcirculatory system responds and particularly increases vascular permeability. The vascular permeability is promoted by chemical mediators and cytokines. Sequentially, chemotaxis, migration and activation of neutrophiles are induced, foreign substances and pathogenic bacteria are phagocytosed at the sites of inflammation, and chemical mediators are released to induce inflammatory responses. Subsequent to neutrophiles, chemotaxis and recruitment of macrophages at the local sites occur, and activated macrophages, like neutrophiles, phagocytose foreign substances, pathogenic bacteria, disintegrated tissues and so on to produce various cytokines. Then, pathogenic bacteria, foreign substances and damaged tissues are removed and the tissues are reconstructed, whereby the inflammation comes to an end. The above-mentioned process occurs in normal inflammatory responses. In allergy and autoimmune diseases such as rheumatoid arthritis and systemic lupus erythematosus, however, abnormal immune responses prolong inflammation and cause strong systemic symptoms.

Many cytokines are involved in various processes of inflammatory responses. For example, IL-1, TNF-$\alpha$ and IL-8 are responsible for the chemotaxis, adhesion to vascular endothelial cells, and migration into vascular walls, of leukocytes, which are seen during migration of leukocytes into the sites of inflammation, wherein IL-1, TNF-$\alpha$ and IL-8 activate neutrophiles to cause release of lysosomal enzymes and production of active oxygen and prostaglandin, thus inducing inflammation. When IL-1, TNF-$\alpha$ and IL-6 migrate into the circulatory system, they act on liver to induce production of acute phase inflammatory protein (e.g., CRP and SAA), and act on bone marrow to increase neutrophiles and platelets. In inflammations of connective tissues, such as rheumatoid arthritis (RA), IL-1 and TNF-$\alpha$ are said to activate fibroblasts and osteoclastic cells and induce production of prostaglandin and collagenase [Mebio, 11 (2), 18–23, (1994)].

As stated in the foregoing, IL-1 and TNF-$\alpha$ play a central role in various aspects of inflammatory responses.

Meanwhile, IL-8 is produced not only by peripheral blood monocytes and tissue macrophages, but also by large granular lymphocytes (LGL) known as natural killer cells, T lymphocytes and various tissues and cells such as fibroblasts, vascular endothelial cells and epidermal keratinocytes. Examples of production stimulators include mitogen lectins such as LPS, PHA, PSK (Coriolus versicolor-derived protein-bound polysaccharide, Krestin) and cytokines such as IL-1 and TNF-$\alpha$.

Although most of these cells barely produce IL-8 constantly, upon stimulation with the above-mentioned IL-8 production stimulators, they produce more than 100 times greater amounts of IL-8 within 24 hours as compared to the production without stimulation. For example, when human peripheral blood monocytes are stimulated with PSK, IL-8 mRNA is induced within an hour, and production amount of IL-8 mRNA reaches its peak in 3 hours, and gradually decreases with time. Along with the induction of IL-8 mRNA, IL-8 protein having neutrophile chemotaxisis ability is detected in the medium at 3 hours after the stimulation and increases with time. IL-8 mRNA is induced in the same manner in time as in the stimulation of IL-1 and TNF-$\alpha$. IL-8 is noticeably stable to protease produced by activated macrophage and the like.

The in vitro biological activities of IL-8 include chemotactic promotion, induction of degranulation, respiratory burst induction, lysosomal enzyme release induction, induction of adhesion to unstimulated or stimulated vascular endothelial cells, promotion of extravascular migration, reinforcement of expression of adhesion factors, leukotriene $B_4$-HETH release induction and the like with regard to neutrophiles; chemotactic promotion with regard to T cells; suppressive effect on IgE production by IL-4 with regard to B cells; and chemotactic promotion and histamine·leukotriene release induction with regard to basophils. IL-8 also has in vivo activities of induction of migration of neutrophiles and lymphocytes, induction of neutrophilia, reinforcement of vascular permeability, and neutrophile-dependent arthrosynovial destruction [Rinsho Men-eki, 25 (8), 1013–1020 (1993)].

As mentioned earlier, IL-8 has various effects on neutrophiles. It has been gradually clarified that IL-8 also acts on T lymphocytes, basophils, monocytes, keratinocytes and melanoma cells, besides neutrophiles. The biological activities and target cells thereof are found to be diverse like other cytokines.

It has been known that IL-8 realizes, in vivo, migration of neutrophiles and lymphocytes at the sites of subcutaneous injections, and increases homing of T lymphocytes to local lymph nodes. It has been also known that an intravenous or intraperitoneal injection of IL-8 markedly increases neutrophile counts in peripheral blood, and administration in large amounts thereof causes destruction of alveoli. In addition, an injection of IL-8 into rabbit intra-articular joint space is known to lead to arthrosynovial destruction with migration of large amounts of neutrophiles. These results suggest strong inflammation induction by IL-8 in vivo.

In view of the fact that IL-8 has various actions besides chemotactic stimulation of neutrophile, that IL-8 was detected in synovial fluid in patients with gout or rheumatic arthritis, that IL-8 was detected from skin pieces of patients with dermatitis such as psoriasis, that IL-8-like chemotactic factor is produced by peripheral blood monocytes in asthma, and that IL-8 was detected in peripheral blood of patients with sepsis which is considered to be one of the causes of adult respiratory distress syndrome (ARDS), it is evident that IL-8 is involved in various diseases such as inflammation.

Therefore, a substance capable of suppressing cytokines responsible for inflammations, such as IL-1, IL-6, IL-8 and TNF-$\alpha$, is extremely useful as a new type of medicine for noninfectious or infectious diseases accompanied by neutrophile migration, which are represented by rheumatic diseases (e.g., rheumatoid arthritis); arthritis due to gout; systemic lupus erythematosus; dermatopathy (e.g., psoriasis, pustulosis and atopic dermatitis); respiratory diseases (e.g., bronchial asthma, bronchitis, ARDS and diffused interstitial pneumonia); inflammatory bowel diseases (e.g., ulcerative colitis and Crohn's disease); acute or chronic hepatitis inclusive of fulminant hepatitis; acute or chronic glomerulonephritis; nephropyelitis; uveitis caused by Behoet disease and vogt-Koyanagi Harada disease; Mediterranean fever (polyserositis); ischemic diseases (e.g., myocardial infarction); and systemic circulatory failure and multi-organ failure caused by sepsis. In particular, such substance is expected to be effective as an anti-inflammatory agent based on new action mechanisms.

With such background of the art, compounds having inhibitory activity on inflammatory cytokines, such as IL-8, have been recently reported. For example, Japanese Patent Application under PCT laid-open under Kohyo No. 7-503017 discloses an imidazole derivative such as 4-(4-fluorophenyl)-2-(4-methylthiophenyl)-5-(4-pyridyl) imidazol as a cytokine inhibitor; Japanese Patent Application under PCT laid-open under Kohyo No. 7-503018 discloses pyridyl-substituted imidazole derivatives such as 1-(4-pyridyl)-2-(4-fluorophenyl)-4-phenylimidazol as cytokine inhibitors; and Japanese Patent Unexamined Publication No. 3-34959 discloses naphthalenemethaneamino derivatives having cytokine inhibitory activity. However, these publications do not suggest the compound of the present invention.

In addition, compounds having inhibitory activity on protease involved in inflammatory diseases have been reported. For example, Japanese Patent Unexamined Publication No. 4-330094 discloses t-butyl-oxycarbonyl-trimethylsilyl-Ala-Pro-NH-CH[(CH$_2$)$_3$N$_3$]-B-pinandiole as a serine protease inhibitor of thrombin which induces pre-inflammatory changes of IL-1 and the like. Japanese Patent Examined Publication No. 7-53705 discloses phenylalanine derivatives such as N-(trans-4-amino-methylcyclohexylcarbonyl)-L-phenylalanine 4-acetylanilide. However, this publication relates to a compound characteristically having amino at one end of phenylalanine and 4-aminomethyl-6-membered ring-carbonyl group at the other end, which relates to a protease inhibitor, and does not relate to an inflammatory cytokine production suppressor, such as the compound of the present invention.

An object of the present invention is to provide a compound usable as a novel selective anti-inflammatory agent which suppresses production and release of inflammatory cytokines such as IL-8, IL-1, TNF-α, IL-6, and the like.

In addition, an object of the present invention is to provide a pharmaceutical agent comprising said compound.

DISCLOSURE OF THE INVENTION

The present inventors have conducted intensive studies with the aim of achieving the above-mentioned objects and completed the present invention.

Accordingly, the present invention provides the following.

(1) An amide compound of the formula (I):

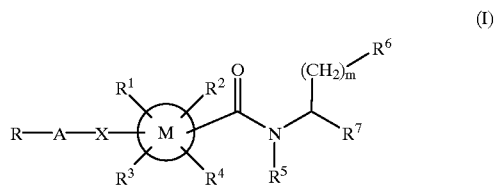

wherein;
R is an optionally substituted non-aromatic heterocyclic group containing nitrogen, a hydroxy, $R_a$, an alkoxy substituted by $R_a$, an alkylthio substituted by $R_a$, or an alkylamino substituted by $R_a$,
  wherein $R_a$ is amino, guanidino, amidino, carbamoyl, ureido, thioureido, hydrazino, hydrazinocarbonyl or imino, these groups being optionally substituted by a substituent selected from the group consisting of lower alkyl, halogenated lower alkyl, cycloalkyl, aralkyl, aryl and amino-protecting group;
A is an optionally substituted, linear or branched alkylene which optionally has one or more double bond(s) or triple bond(s) in the chain, or a single bond;
X is an oxygen atom, a sulfur atom, a cycloalkylene, a divalent aromatic heterocyclic group having one or more hetero atom(s) selected from the group consisting of a nitrogen atom, sulfur atom and oxygen atom, —SO—, —SO$_2$—, —C=C—, —C≡C—, —CO—, —COO—, —OOC—, —CS—, —COS—, —O—CO—O—, —NH—CO—NH—, —NH—CS—NH—, —NH—C(=NH)—NH—, —NR$^8$—, —NR$^8$CO—, —CONR$^8$—, —NR$^8$SO$_2$—, —SO$_2$NR$^8$—, —NR$^8$—NR$^8$—, or —CR$^9$R$^{10}$—
  wherein R$^8$ is hydrogen atom, alkyl, cycloalkyl, aryl, aralkyl or amino-protecting group, and R$^9$ and R$^{10}$ are the same or different and each is hydrogen atom, alkyl, cycloalkyl, aryl or aralkyl;
M is an arylene, a cycloalkylene, or a divalent heterocyclic group which has one or more hetero atom(s) selected from the group consisting of a nitrogen atom, sulfur atom and oxygen atom, and which optionally forms a fused ring;
R$^1$, R$^2$, R$^3$ and R$^4$ are the same or different and each is a hydrogen atom, a hydroxy, a halogen atom, an alkoxy, a mercapto, an alkylthio, a nitro, a cyano, a carboxy, an alkoxycarbonyl, an aryloxycarbonyl, an acyl, an alkyl optionally substituted by a substituent selected from the group consisting of hydroxy, lower alkoxy and halogen atom, an amino optionally substituted by a substituent selected from the group consisting of alkyl, aryl, aralkyl and amino-protecting group, or —O—CO—R$^{11}$
  wherein R$^{11}$ is optionally substituted alkoxy, optionally substituted aryl, optionally substituted cycloalkyl, optionally substituted aryloxy, optionally substituted aralkyloxy, optionally substituted alkylthio, optionally substituted arylthio, or alkyl optionally substituted by a substituent selected from the group consisting of alkoxycarbonyl, acyloxy, aryl, aryloxy, aryloxycarbonyl, aralkyloxy, aralkyloxycarbonyl, alkylthio, arylthio, acyl, lower alkoxy, carboxy, halogen atom and amino optionally substituted by lower alkyl or acyl;
R$^5$ is a hydrogen atom, an alkyl optionally substituted by halogen atom, an optionally substituted aralkyl, or an amino-protecting group;
m is 0 or an integer of 1–6;

$R^6$ is an optionally substituted aryl, an optionally substituted cycloalkyl, an optionally substituted lower alkyl, an optionally substituted lower alkoxy, an optionally substituted lower alkylthio, an amino optionally substituted by a substituent selected from the group consisting of lower alkyl, aryl, aralkyl and amino-protecting group, or an optionally substituted heterocyclic group having one ore more hetero atoms selected from the group consisting of a nitrogen atom, sulfur atom and oxygen atom; and $R^7$ is a hydrogen atom, an optionally substituted alkyl, an optionally substituted aryl, an optionally substituted aromatic heterocyclic group having one ore more hetero atoms selected from the group consisting of a nitrogen atom, sulfur atom and oxygen atom, or $—CO(Y)_pR^{12}$ wherein Y is oxygen atom, sulfur atom, $—NR^{13}—$ or $—NR^{13}—SO_2—$ wherein $R^{13}$ is hydrogen atom, alkyl, aralkyl, hydroxy, alkoxy, aryl or amino-protecting group, p is 0 or 1, and $R^{12}$ is hydrogen atom, optionally substituted alkenyl, optionally substituted alkynyl, optionally substituted cycloalkyl, optionally substituted aryl, optionally substituted aralkyl, adamantyl, cycloalkylideneamino, optionally substituted heterocyclic group having one or more hetero atom(s) selected from the group consisting of nitrogen atom, sulfur atom and oxygen atom, or alkyl optionally substituted by a substituent selected from the group consisting of hydroxy, alkoxy, alkoxyalkoxy, alkoxycarbonyl, acyloxy, carboxy, heterocyclic group having one or more hetero atom(s) selected from the group consisting of nitrogen atom, sulfur atom and oxygen atom, and amino optionally substituted by a substituent selected from the group consisting of alkyl, aryl, aralkyl and amino-protecting group;

and a pharmaceutically acceptable acid addition salt thereof.

(2) The amide compound of (1) above, wherein, in the formula (I), at least one symbol selected from the group consisting of R, A, X, M, $R^1$, $R^2$, $R^3$, $R^4$, $R^5$, m, $R^6$ and $R^7$ satisfies the following definitions, and a pharmaceutically acceptable acid addition salt thereof:

R is a non-aromatic heterocyclic group containing nitrogen, which is optionally substituted by lower alkyl or amino-protecting group, $R_{a1}$, an alkoxy substituted by $R_{a1}$, an alkylthio substituted by $R_{a1}$, or an alkylamino substituted by $R_{a1}$, wherein $R_{a1}$ is amino, guanidino, amidino, carbamoyl, ureido, thioureido, hydrazino, hydrazinocarbonyl or imino, these groups being optionally substituted by a substituent selected from the group consisting of lower alkyl, aralkyl and amino-protecting group;

A is a linear or branched alkylene which optionally has one or more double bond(s) or triple bond(s) in the chain, or a single bond;

X is an oxygen atom, a sulfur atom, a cycloalkylene, a divalent aromatic heterocyclic group having one or more hetero atom(s) selected from the group consisting of a nitrogen atom, sulfur atom and oxygen atom, $—SO—$, $—SO_2—$, $—C=C—$, $—C\equiv C—$, $—CO—$, $—COO—$, $—OOC—$, $—CS—$, $—COS—$, $—O—CO—O—$, $—NH—CO—NH—$, $—NH—CS—NH—$, $—NH—C(=NH)—NH—$, $—NR^{8'}—$, $—NR^{8'}CO—$, $—CONR^{8'}—$, $—NR^{8'}SO_2—$, $—SO_2NR^{8'}—$, $—NR^{8'}—COO—$, $—OOC—NR^{8'}—$, or $—CR^{9'}R^{10'}—$ wherein $R^{8'}$ is hydrogen atom, lower alkyl, aralkyl or amino-protecting group, and $R^{9'}$ and $R^{10'}$ are the same or different and each is hydrogen atom, lower alkyl or aralkyl;

M is an arylene, a cycloalkylene or a divalent heterocyclic group which has one or more hetero atom(s) selected from the group consisting of a nitrogen atom, sulfur atom and oxygen atom, and which optionally forms a fused ring;

$R^1$, $R^2$, $R^3$ and $R^4$ are the same or different and each is a hydrogen atom, a hydroxy, a halogen atom, a lower alkoxy, a mercapto, a lower alkylthio, a nitro, a cyano, a carboxy, a lower alkoxycarbonyl, an aryloxycarbonyl, an acyl, a lower alkyl optionally substituted by a substituent selected from the group consisting of hydroxy, lower alkoxy and halogen atom, an amino optionally substituted by a substituent selected from the group consisting of lower alkyl, aralkyl and amino-protecting group, or $—O—CO—R^{11'}$ wherein $R^{11'}$ is lower alkoxy, optionally substituted cycloalkyl, lower alkyl optionally substituted by a substituent selected from the group consisting of lower alkoxy-carbonyl, acyloxy, aralkyloxy, aralkyloxycarbonyl, acyl, lower alkoxy, carboxy and amino optionally substituted by lower alkyl, or aryl optionally substituted by a substituent selected from the group consisting of lower alkyl, carboxy and benzyloxycarbonyl;

$R^5$ is a hydrogen atom, an alkyl optionally substituted by halogen atom, an optionally substituted aralkyl, or an amino-protecting group;

m is 0 or an integer of 1–6;

$R^6$ is an aryl, a cycloalkyl, or a heterocyclic group having one or more hetero atom(s) selected from the group consisting of a nitrogen atom, sulfur atom and oxygen atom wherein said aryl, cycloalkyl and heterocyclic group having one or more hetero atom(s) selected from the group consisting of nitrogen atom, sulfur atom and oxygen atom are optionally substituted by a substituent selected from the group consisting of lower alkyl, halogen atom, hydroxy, lower alkoxy, amino, carboxy and lower alkoxycarbonyl; and $R^7$ is a hydrogen atom, a lower alkyl optionally substituted by a substituent selected from the group consisting of hydroxy, lower alkoxy, mercapto, lower alkylthio, carboxy, lower alkoxycarbonyl and amino, an aromatic heterocyclic group which has one or more hetero atom(s) selected from the group consisting of a nitrogen atom, sulfur atom and oxygen atom, and which is optionally substituted by lower alkyl, or $—CO(Y')_pR^{12'}$ wherein Y' is oxygen atom, sulfur atom, $—NR^{13'}—$ or $—NR^{13'}—SO_2—$ wherein $R^{13'}$ is hydrogen atom, lower alkyl, aralkyl, hydroxy, lower alkoxy or amino-protecting group, p is 0 or 1, and $R^{12'}$ is hydrogen atom, aralkyl, adamantyl, cycloalkylideneamino, cycloalkyl optionally substituted by lower alkyl, alkyl optionally substituted by a substituent selected from the group consisting of hydroxy, lower alkoxy, lower alkoxy lower alkoxy, lower alkoxycarbonyl, acyloxy, carboxy, heterocyclic group having one or more hetero atom(s) selected from the group consisting of, nitrogen atom, sulfur atom and oxygen atom, and amino optionally substituted by a substituent selected from the group consisting of lower alkyl, aralkyl and amino-protecting group, aryl optionally substituted by a substituent selected from the group consisting of lower alkyl, halogen atom, amino, carboxy, hydroxy and lower alkoxy, or heterocyclic group which is optionally substituted by a substituent selected from the group consisting of lower alkyl, halogen atom, amino, carboxy, hydroxy and lower alkoxy, and which has one or more hetero atom(s) selected from the group consisting of nitrogen atom, sulfur atom and oxygen atom.

(3) The amide compound of (1) above, wherein, in the formula (I), at least one symbol selected from the group consisting of R, A, X, M, $R^1$, $R^2$, $R^3$, $R^4$, $R^5$, m, $R^6$ and $R^7$ satisfies the following definitions, and a pharmaceutically acceptable acid addition salt thereof:

R is a non-aromatic heterocyclic group containing nitrogen, which is optionally substituted by lower alkyl or amino-protecting group, $R_{a2}$, or an alkoxy substituted by $R_{a2}$,
    wherein $R_{a2}$ is amino, guanidino, amidino or carbamoyl, these groups being optionally substituted by lower alkyl or amino-protecting group;

A is a linear alkylene or a single bond;

X is an oxygen atom, a sulfur atom, a divalent aromatic heterocyclic group having one or more hetero atom(s) selected from the group consisting of a nitrogen atom, sulfur atom and oxygen atom, —COO—, —OOC—, $NR^{8\prime\prime}$—, —$NR^{8\prime\prime}$—CO—, —$CONR^{8\prime\prime}$—, —$NR^{8\prime\prime}SO_2$—, —$SO_2NR^{8\prime\prime}$—, or —$CR^{9\prime\prime}R^{10\prime\prime}$—
    wherein $R^{8\prime\prime}$ is hydrogen atom, lower alkyl or amino-protecting group, and $R^{9\prime\prime}$ and $R^{10\prime\prime}$ are the same or different and each is hydrogen atom or lower alkyl;

M is an arylene or a divalent heterocyclic group which has one or more hetero atom(s) selected from the group consisting of a nitrogen atom, sulfur atom and oxygen atom, and which optionally forms a fused ring;

$R^1$, $R^2$, $R^3$ and $R^4$ are the same or different and each is a hydrogen atom, a hydroxy, a halogen atom, lower alkoxy, a lower alkyl optionally substituted by a substituent selected from the group consisting of hydroxy, lower alkoxy and halogen atom, or —O—CO—$R^{11\prime\prime}$
    wherein $R^{11\prime\prime}$ is lower alkoxy, cycloalkyl, aryl optionally substituted by lower alkyl, or lower alkyl optionally substituted by a substituent selected from the group consisting of acyloxy, aralkyloxycarbonyl and amino optionally substituted by lower alkyl;

$R^5$ is a hydrogen atom, a lower alkyl, or an amino-protecting group;

m is 1;

$R^6$ is an aryl or a cycloalkyl
    wherein said aryl and cycloalkyl are optionally substituted by halogen atom or hydroxy; and $R^7$ is a hydrogen atom, a lower alkyl optionally substituted by hydroxy or lower alkoxy, an aromatic heterocyclic group which has one or more hetero atom(s) selected from the group consisting of a nitrogen atom, sulfur atom and oxygen atom, and which is optionally substituted by lower alkyl, or —CO(Y")$_p$$R^{12\prime\prime}$
    wherein Y" is oxygen atom, sulfur atom or —$NR^{13\prime\prime}$—
    wherein
        $R^{13\prime\prime}$ is hydrogen atom, lower alkyl, hydroxy or amino-protecting group,
        p is 0 or 1, and $R^{12\prime\prime}$ is hydrogen atom, aralkyl, adamantyl, cycloalkylideneamino, cycloalkyl optionally substituted by lower alkyl, aryl optionally substituted by halogen atom, alkyl optionally substituted by a substituent selected from the group consisting of hydroxy, lower alkoxy, lower alkoxy lower alkoxy, lower alkoxycarbonyl, acyloxy, carboxy, heterocyclic group having one or more hetero atom(s) selected from the group consisting of nitrogen atom, sulfur atom and oxygen atom, and amino optionally substituted by a substituent selected from the group consisting of lower alkyl, aralkyl and amino-protecting group, or heterocyclic group which is optionally substituted by lower alkyl, and which has one or more hetero atom(s) selected from the group consisting of nitrogen atom, sulfur atom and oxygen atom.

(4) The amide compound of (1) above, wherein, in the formula (I), at least one symbol selected from the group consisting of R, A, X, M, $R^1$, $R^2$, $R^3$, $R^4$, $R^5$, m, $R^6$ and $R^7$ satisfies the following definitions, and a pharmaceutically acceptable acid addition salt thereof:

R is a piperazinyl optionally substituted by lower alkyl, a piperidyl optionally substituted by lower alkyl, an amino, or a lower alkoxy substituted by amino
    wherein amino is optionally substituted by lower alkyl;

A is a linear alkylene;

X is an oxygen atom, a sulfur atom, —NH— or —$CH_2$—;

M is an arylene;

$R^1$, $R^2$, $R^3$ and $R^4$ are the same or different and each is a hydrogen atom, a hydroxy, a halogen atom, or —O—CO—$R^{11\prime\prime\prime\prime}$
    wherein $R^{11\prime\prime\prime\prime}$ is lower alkyl optionally substituted by a substituent selected from the group consisting of amino, acyloxy and benzyloxycarbonyl, or phenyl optionally substituted by lower alkyl;

$R^5$ is a hydrogen atom;

m is 1;

$R^6$ is a phenyl; and $R^7$ is —COO—$R^{12\prime\prime\prime}$
    wherein $R^{12\prime\prime\prime}$ is hydrogen atom, aralkyl, adamantyl, cyclohexylideneamino, cyclohexyl optionally substituted by lower alkyl, piperidyl optionally substituted by lower alkyl, or alkyl optionally substituted by a substituent selected from the group consisting of hydroxy, lower alkoxy, lower alkoxy lower alkoxy, lower alkoxycarbonyl, acyloxy, piperazinyl and amino optionally substituted by lower alkyl.

(5) The amide compound of (4) above, wherein M is phenylene, and a pharmaceutically acceptable acid addition salt thereof.

(6) The amide compound of (4) above, wherein $R^7$ is —COO—$R^{12\prime\prime\prime\prime}$ wherein $R^{12\prime\prime\prime\prime}$ is lower alkyl, or cyclohexyl which is optionally substituted by lower alkyl, and a pharmaceutically acceptable acid addition salt thereof.

(7) The amide compound of (4) above, wherein X is oxygen atom or —$CH_2$—, and a pharmaceutically acceptable acid addition salt thereof.

(8) The amide compound of (4) above, wherein $R^6$ is phenyl and m is 1, and a pharmaceutically acceptable acid addition salt thereof.

(9) The amide compound of (4) above, wherein R is amino optionally substituted by lower alkyl, piperazinyl optionally substituted by lower alkyl, or piperidyl optionally substituted by lower alkyl, and a pharmaceutically acceptable acid addition salt thereof.

(10) The amide compound of (4) above, wherein $R^1$, $R^2$ $R^3$ and $R^4$ are the same or different and each is hydrogen atom, hydroxy, halogen atom, or —O—CO—$R^{11\prime\prime\prime\prime}$ wherein $R^{11\prime\prime\prime\prime}$ is lower alkyl or phenyl, and a pharmaceutically acceptable acid addition salt thereof.

9

(11) A carboxylic acid compound of the formula (I-a)

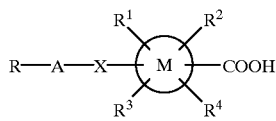

(I-a)

wherein;
R is an optionally substituted non-aromatic heterocyclic group containing nitrogen, a hydroxy, $R_a$, an alkoxy substituted by $R_a$, an alkylthio substituted by $R_a$, or an alkylamino substituted by $R_a$,
  wherein $R_a$ is amino, guanidino, amidino, carbamoyl, ureido, thioureido, hydrazino, hydrazinocarbonyl or imino, these groups being optionally substituted by a substituent selected from the group consisting of lower alkyl, halogenated lower alkyl, cycloalkyl, aralkyl, aryl and amino-protecting group;
A is an optionally substituted, linear or branched alkylene which optionally has one or more double bond(s) or triple bond(s) in the chain, or a single bond;
X is an oxygen atom, a sulfur atom, a cycloalkylene, a divalent aromatic heterocyclic group having one ore more hetero atoms selected from the group consisting of a nitrogen atom, sulfur atom and oxygen atom, —SO—, —SO$_2$—, —C=C—, —C≡C—, —CO—, —COO—, —OOC—, —CS—, —COS—, —O—CO—O—, —NH—CO—NH—, —NH—CS—NH—, —NH—C(=NH)—NH—, —NR$^8$—, —NR$^8$CO—, —CONR$^8$—, —NR$^8$SO$_2$—, —SO$_2$NR$^8$—, —NR$^8$—COO—, —OOC—NR$^8$—, or —CR$^9$R$^{10}$—
  wherein $R^8$ is hydrogen atom, alkyl, cycloalkyl, aryl, aralkyl or amino-protecting group, and $R^9$ and $R^{10}$ are the same or different and each is hydrogen atom, alkyl, cycloalkyl, aryl or aralkyl;
M is an arylene, a cycloalkylene or a divalent heterocyclic group which has one ore more hetero atoms selected from the group consisting of a nitrogen atom, sulfur atom and oxygen atom, and which optionally forms a fused ring; and
$R^1$, $R^2$, $R^3$ and $R^4$ are the same or different and each is a hydrogen atom, a hydroxy, a halogen atom, an alkoxy, a mercapto, an alkylthio, a nitro, a cyano, a carboxy, an alkoxycarbonyl, an aryloxycarbonyl, an acyl, an alkyl optionally substituted by a substituent selected from the group consisting of hydroxy, lower alkoxy and halogen atom, an amino optionally substituted by a substituent selected from the group consisting of alkyl, aryl, aralkyl and amino-protecting group, or —O—CO—R$^{11}$
  wherein $R^{11}$ is optionally substituted alkoxy, optionally substituted aryl, optionally substituted cycloalkyl, optionally substituted aryloxy, optionally substituted aralkyloxy, optionally substituted alkylthio, optionally substituted arylthio, or alkyl optionally substituted by a substituent selected from the group consisting of alkoxycarbonyl, acyloxy, aryl, aryloxy, aryloxycarbonyl, aralkyloxy, aralkyloxycarbonyl, alkylthio, arylthio, acyl, lower alkoxy, carboxy, halogen atom and amino optionally substituted by lower alkyl or acyl.

(12) The carboxylic acid compound of (11) above, wherein, in the formula (I-a), at least one of R, A, X, M, $R^1$, $R^2$, $R^3$ and $R^4$ satisfies the following definitions:
R is a piperazinyl optionally substituted by lower alkyl, a piperidyl optionally substituted by lower alkyl, an amino or a lower alkoxy substituted by amino

10 wherein amino is optionally substituted by lower alkyl;
A is a linear alkylene;
X is an oxygen atom, a sulfur atom, —NH— or CH$_2$—;
M is an arylene; and
$R^1$, $R^2$, $R^3$ and $R^4$ are the same or different and each is a hydrogen atom, a hydroxy, a halogen atom, or —O—CO—R$^{11'''}$
  wherein $R^{11'''}$ is a lower alkyl optionally substituted by a substituent selected from the group consisting of amino, acyloxy and benzyloxycarbonyl, or phenyl optionally substituted by lower alkyl.

(13) An amide compound of the formula (I-b)

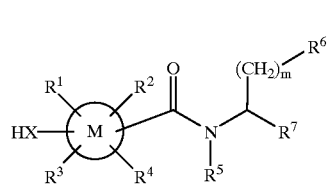

(I-b)

X is an oxygen atom, a sulfur atom, a cycloalkylene, a divalent aromatic heterocyclic group having one or more hetero atom(s) selected from the group consisting of a nitrogen atom, sulfur atom and oxygen atom, —SO—, —SO$_2$—, —C=C—, —C≡C—, —CO—, —COO—, —OOC—, —CS—, —COS—, —O—CO—O—, —NH—CO—NH—, —NH—CS—NH—, —NH—C(=NH)—NH—, —NR$^8$—, —NR$^8$CO—, —CONR$^8$—, —NR$^8$SO$_2$—, —SO$_2$NR$^8$—, —NR$^8$—COO—, —OOC—NR$^8$— or —CR$^9$R$^{10}$—
  wherein $R^8$ is hydrogen atom, alkyl, cycloalkyl, aryl, aralkyl or amino-protecting group, and $R^9$ and $R^{10}$ are the same or different and each is hydrogen atom, alkyl, cycloalkyl, aryl or aralkyl;
M is an arylene, cycloalkylene, or a divalent heterocyclic group which has one or more hetero atom(s) selected from the group consisting of a nitrogen atom, sulfur atom and oxygen atom, and which optionally forms a fused ring;
$R^1$, $R^2$, $R^3$ and $R^4$ are the same or different and each is a hydrogen atom, a hydroxy, a halogen atom, an alkoxy, a mercapto, an alkylthio, a nitro, a cyano, a carboxy, an alkoxycarbonyl, an aryloxycarbonyl, an acyl, an alkyl optionally substituted by a substituent selected from the group consisting of hydroxy, lower alkoxy and halogen atom, an amino optionally substituted by a substituent selected from the group consisting of alkyl, aryl, aralkyl and amino-protecting group, or —O—R$^{11}$
  wherein $R^{11}$ is optionally substituted alkoxy, optionally substituted aryl, optionally substituted cycloalkyl, optionally substituted aryloxy, optionally substituted aralkyloxy, optionally substituted alkylthio, optionally substituted arylthio, or alkyl optionally substituted by a substituent selected from the group consisting of alkoxycarbonyl, acyloxy, aryl, aryloxy, aryloxycarbonyl, aralkyloxy, aralkyloxycarbonyl, alkylthio, arylthio, acyl, lower alkoxy, carboxy, halogen atom and amino optionally substituted by lower alkyl or acyl;
$R^5$ is a hydrogen atom, an alkyl optionally substituted by halogen atom, optionally substituted aralkyl, or an amino-protecting group;
m is 0 or an integer of 1–6;
$R^6$ is an optionally substituted aryl, an optionally substituted cycloalkyl, an optionally substituted lower alkyl, an optionally substituted lower alkoxy, an optionally substituted lower alkylthio, an amino optionally substituted by a substituent selected from the group consisting of lower alkyl, aryl, aralkyl and amino-protecting group, or an optionally substituted heterocyclic group having one or more hetero atom(s) selected from the group consisting of a nitrogen atom, sulfur atom and oxygen atom; and $R^7$ is a hydrogen atom, an optionally substituted alkyl, an optionally substituted aryl, an optionally substituted aromatic heterocyclic group having one or more hetero atom(s) selected from the group consisting of a nitrogen atom, sulfur atom and oxygen atom, or —CO(Y)$_p$R$^{12}$ wherein Y is oxygen atom, sulfur atom, —NR$^{13}$— or —NR$^{13}$—SO$_2$— wherein $R^{13}$ is hydrogen atom, alkyl, aralkyl, hydroxy, alkoxy, aryl or amino-protecting group, p is 0 or 1, and $R^{12}$ is hydrogen atom, optionally substituted alkenyl, optionally substituted alkynyl, optionally substituted cycloalkyl, optionally substituted aryl, optionally substituted aralkyl, adamantyl, cycloalkylideneamino, alkyl optionally substituted by a substituent selected from the group consisting of hydroxy, alkoxy, alkoxyalkoxy, alkoxycarbonyl, acyloxy, carboxy, heterocyclic group having one or more hetero atom(s) selected from the group consisting of a nitrogen atom, sulfur atom and oxygen atom, and amino optionally substituted by a substituent selected from the group consisting of alkyl, aryl, aralkyl and amino-protecting group, or optionally substituted heterocyclic group having one or more hetero atom(s) selected from the group consisting of a nitrogen atom, sulfur atom and oxygen atom.

(14) The amide compound of (13) above, wherein, in the formula (I-b), at least one symbol selected from the group consisting of X, M, $R^1$, $R^2$, $R^3$, $R^4$, $R^5$, m, $R^6$ and $R^7$ satisfies the following definitions:

X is an oxygen atom, a sulfur atom or —NH—;

M is an arylene;

$R^1$, $R^2$, $R^3$ and $R^4$ are the same or different and each is a hydrogen atom, a hydroxy, a halogen atom, or —O—CO—R$^{11''''}$ wherein $R^{11''''}$ is lower alkyl optionally substituted by a substituent selected from the group consisting of amino, acyloxy and benzyloxycarbonyl, or a phenyl optionally substituted by lower alkyl;

$R^5$ is a hydrogen atom;

m is 1;

$R^6$ is a phenyl; and $R^7$ is —COO—R$^{12'''}$ wherein $R^{12'''}$ is hydrogen atom, aralkyl, adamantyl, cyclohexyl-ideneamino, piperidyl optionally substituted by lower alkyl, cyclohexyl optionally substituted by lower alkyl, or alkyl optionally substituted by a substituent selected from the group consisting of hydroxy, lower alkoxy, lower alkoxy lower alkoxy, lower alkoxycarbonyl, acyloxy, piperazinyl, and amino optionally substituted by lower alkyl.

(15) A pharmaceutical composition comprising a pharmaceutically acceptable carrier, and the amide compound of any one of (1) to (10) above or a pharmaceutically acceptable acid addition salt thereof.

(16) An inflammatory cytokine production suppressor comprising the amide compound of any one of (1) to (10) above or a pharmaceutically acceptable acid addition salt thereof as an active ingredient.

(17) An agent for the treatment or prophylaxis of an inflammatory diseases, comprising the amide compound of any one of (1) to (10) above or a pharmaceutically acceptable acid addition salt thereof as an active ingredient.

In the present specification, each substituent means as follows.

"Alkoxy" is linear or branched alkoxy having 1 to 6 carbon atoms, which is exemplified by methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy, with preference given to linear or branched alkoxy having 1 to 4 carbon atoms, such as methoxy, ethoxy, propoxy, isopropoxy, butoxy, isobutoxy, sec-butoxy and tert-butoxy.

"Lower alkoxy" is linear or branched alkoxy having 1 to 4 carbon atoms, which is exemplified by methoxy, ethoxy, propoxy, isopropoxy, butoxy, isobutoxy, sec-butoxy and tert-butoxy, with preference given to methoxy and ethoxy.

"Alkylthio" is linear or branched alkylthio having 1 to 6 carbon atoms, which is exemplified by methylthio, ethylthio, propylthio, isopropylthio, butylthio, isobutylthio, sec-butylthio, tert-butylthio, pentylthio, isopentylthio, neopentylthio, tert-pentylthio, hexylthio, isohexylthio and neohexylthio.

"Lower alkylthio" is linear or branched alkylthio having 1 to 4 carbon atoms, which is exemplified by methylthio, ethylthio, propylthio, isopropylthio, butylthio, isobutylthio, sec-butylthio and tert-butylthio.

"Alkylamino" is linear or branched, monoalkylamino or dialkylamino which has 1 to 6 carbon atoms, which is exemplified by methylamino, dimethylamino, ethylamino, diethylamino, methylethylamino, propylamino, isopropylamino, butylamino, isobutylamino, sec-butylamino, tert-butylamino, pentylamino, isopentylamino, neopentylamino, tert-pentylamino, hexylamino, isohexylamino and neohexylamino, with preference given to linear alkylamino, such as methylamino, dimethylamino, ethylamino, diethylamino, propylamino, butylamino, pentylamino and hexylamino. Particularly preferred is linear alkylamino having 1 to 4 carbon atoms, which is exemplified by methylamino, dimethylamino, ethylamino, diethylamino, propylamino and butylamino.

"Non-aromatic heterocyclic group containing nitrogen" is 3- to 7-membered non-aromatic heterocyclic group which has at least one nitrogen atom and optionally a sulfur atom or oxygen atom, and which is optionally fused with benzene ring. Specific examples thereof include aziridinyl, thiazetidinyl, azetidinyl, pyrrolidinyl, pyrrolinyl, imidazolidinyl, imidazolinyl, pyrazolidinyl, pyrazolinyl, morpholinyl, morpholino, oxazinyl, thiazinyl, piperazinyl, piperidyl, piperidino, dioxazepinyl, thiazepinyl, diazepinyl, perhydrodiazepinyl, azepinyl, perhydroazepinyl, indolinyl and isoindolinyl. Preferred are aziridinyl, azetidinyl, pyrrolidinyl, pyrazolidinyl, morpholinyl, morpholino, piperazinyl, piperidyl, piperidino and perhydroazepinyl, and particularly preferred are pyrrolidinyl, morpholino, piperazinyl, piperidyl and piperidino.

"Alkyl" is linear or branched alkyl having 1 to 6 carbon atoms, which is exemplified by methyl, ethyl, propyl, isopropyl, butyl, isobutyl, sec-butyl, tert-butyl, pentyl, isopentyl, neopentyl, tert-pentyl, hexyl, isohexyl and neohexyl.

"Lower alkyl" is linear or branched alkyl having 1 to 4 carbon atoms, which is exemplified by methyl, ethyl, propyl, isopropyl, butyl, isobutyl, sec-butyl and tert-butyl.

"Halogen atom" is specifically a fluorine atom, chlorine atom, bromine atom or iodine atom.

"Halogenated lower alkyl" is that wherein the above-mentioned lower alkyl is substituted by a halogen atom, and is exemplified by fluoromethyl, chloromethyl, bromomethyl, difluoromethyl, dichloromethyl, trifluoromethyl, trichloromethyl, difluoroethyl, dichloroethyl, pentatrifluoroethyl, trichloroethyl and fluoropropyl, with preference given to fluoromethyl, chloromethyl, difluoromethyl, dichloromethyl and trifluoromethyl.

"Cycloalkyl" is that having 3 to 7 carbon atoms, which is exemplified by cyclopropyl, cyclobutyl, cyclopentyl, cyclohexyl and cycloheptyl, with preference given to cycloalkyl having 5 or 6 carbon atoms, such as cyclopentyl and cyclohexyl.

"Aralkyl" is that wherein alkyl is substituted by aryl and is exemplified by benzyl, benzhydryl, trityl, phenethyl, 3-phenylpropyl, 2-phenylpropyl, 4-phenylbutyl and naphthylmethyl, with preference given to benzyl and phenethyl.

"Aralkyloxy" is that having the above-mentioned aralkyl, which is exemplified by benzyloxy, benzhydryloxy, trityloxy, phenethyloxy, 3-phenylpropyloxy, 2-phenylpropyloxy, 4-phenylbutyloxy and naphthylmethoxy, with preference given to benzyloxy and phenethyloxy.

"Aralkyloxycarbonyl" is that having the above-mentioned aralkyl, which is exemplified by benzyloxycarbonyl, benzhydryloxycarbonyl, trityloxycarbonyl, phenethyloxycarbonyl, 3-phenylpropyloxycarbonyl, 2-phenylpropyloxycarbonyl, 4-phenylbutyloxycarbonyl and naphthylmethoxy-carbonyl, with preference given to benzyloxycarbonyl and phenethyloxy-carbonyl.

"Aryl" is phenyl, naphthyl, anthryl, phenanthryl or biphenyl, with preference given to phenyl and naphthyl.

"Aryloxy" is that having the above-mentioned aryl, which is exemplified by phenoxy and naphthyloxy.

"Aryloxycarbonyl" is that having the above-mentioned aryl, which is exemplified by phenoxycarbonyl and naphthyloxycarbonyl.

"Arylthio" is that having the above-mentioned aryl, which is exemplified by phenylthio and naphthylthio.

"Amino-protecting group" is a protecting group conventionally used, which is subject to no particular limitation as long as it protects amino from various reactions. Specific examples include acyl such as formyl, acetyl, propionyl, butyryl, oxalyl, succinyl, pivaloyl, 2-chloroacetyl, 2-bromoacetyl, 2-iodoacetyl, 2,2-dichloroacetyl, 2,2,2-trichloroacetyl, 2,2,2-trifluoroacetyl, phenylacetyl, phenoxyacetyl, benzoyl, 4-chlorobenzoyl, 4-methoxybenzoyl, 4-nitrobenzoyl, naphthyl-carbonyl, adamantylcarbonyl and phthaloyl; alkoxycarbonyl such as methoxycarbonyl, ethoxycarbonyl, propoxycarbonyl, isopropoxycarbonyl, tert-butoxycarbonyl, pentyloxycarbonyl, isopentyloxycarbonyl, cyclohexyloxycarbonyl, 2-chloroethoxycarbonyl, 2-iodoethoxycarbonyl, 2,2,2-trichloroethoxycarbonyl, 2,2,2-trichloro-tert-butoxycarbonyl, benzhydryloxycarbonyl, bis-(4-methoxyphenyl)methoxycarbonyl, phenacyloxycarbonyl, 2-trimethylsilylethoxycarbonyl, 2-triphenylsilylethoxycarbonyl and fluorenyl-9-methoxycarbonyl; alkenyloxycarbonyl such as vinyloxycarbonyl, 2-propenyloxycarbonyl, 2-chloro-2-propenyloxycarbonyl, 3-methoxycarbonyl-2-propenyloxycarbonyl, 2-methyl-2-propenyloxycarbonyl, 2-butenyloxycarbonyl and cinnamyloxycarbonyl; aralkyloxycarbonyl such as benzyloxycarbonyl, 4-bromobenzyloxycarbonyl, 2-chlorobenzyloxycarbonyl, 3-chlorobenzyloxycarbonyl, 3,5-dimethoxybenzyloxycarbonyl, 4-methoxybenzyloxycarbonyl, 2-nitrobenzyloxycarbonyl, 4-nitrobenzyloxycarbonyl, 2-nitro-4,5-dimethoxybenzyloxycarbonyl, 3,4,5-trimethoxybenzyloxycarbonyl and phenethyloxycarbonyl; lower alkylsilyl such as trimethyl-silyl and tert-butyldimethylsilyl; alkylenebis (dialkylsilyl) such as ethylenebis(dimethylsilyl), propylenebis(dimethylsilyl) and ethylene-bis(diethylsilyl); alkylthiocarbonyl such as methylthiocarbonyl, ethylthiocarbonyl, butylthiocarbonyl and tert-butylthiocarbonyl; aralkylthiocarbonyl such as benzylthiocarbonyl; phosphoryl such as dicyclohexylphosphoryl, diphenylphosphoryl, dibenzylphosphoryl, di-(4-nitrobenzyl)phosphoryl and phenoxyphenylphosphoryl; and phosphinyl such as diethylphosphinyl, diphenylphosphinyl.

"Linear or branched alkylene optionally having one or more double bond(s) or triple bond(s) in the chain" is linear or branched alkylene having 1 to 10 carbon atoms, which may have one ore more double bonds or triple bonds in the chain, and is exemplified by methylene, ethylene, trimethylene, tetramethylene, pentamethylene, hexamethylene, heptamethylene, octamethylene, nonamethylene, decamethylene, dimethylmethylene, diethylmethylene, propylene, methylethylene, ethylethylene, propylethylene, isopropylethylene, methylpentaethylene, ethylhexamethylene, dimethylethylene, methyltriethylene, dimethyltrimethylene, vinylene, propenylene, butenylene, butadienylene, pentenylene, pentadienylene, hexenylene, hexadienylene, hexatrienylene, heptenylene, heptadienylene, heptatrienylene, octenylene, octadienylene, octatrienylene, octatetraenylene, propynylene, butynylene, pentynylene and methylpropynylene, with preference given to linear alkylene, such as methylene, ethylene, trimethylene, tetramethylene, pentamethylene, hexamethylene, heptamethylene, octamethylene, nonamethylene, decamethylene, vinylene, propenylene, butenylene, butadienylene, pentenylene, pentadienylene, hexenylene, hexadienylene, hexatrienylene, heptenylene, heptadienylene, heptatrienylene, octenylene, octadienylene, octatrienylene, octatetraenylene, propynylene, butynylene and pentynylene. Particularly preferred is linear alkylene having 1 to 8 carbon atoms, such as methylene, ethylene, trimethylene, tetramethylene, pentamethylene, hexamethylene, heptamethylene and octamethylene.

"Divalent aromatic heterocyclic group having one or more hetero atom(s) selected from the group consisting of a nitrogen atom, sulfur atom and oxygen atom" is 5- or 6-membered divalent aromatic heterocyclic group having one or more hetero atom(s) selected from the group consisting of a nitrogen atom, sulfur atom and oxygen atom, which is exemplified by divalent groups of tetrazole ring, oxadiazole ring, thiadiazole ring, triazole ring, oxazole ring, isoxazole ring, thiazole ring, isothiazole ring, imidazole ring, pyrazole ring, pyrrole ring, furan ring, thiophene ring, tetrazine ring, triazine ring, pyrazine ring, pyridazine ring, pyrimidine ring and pyridine ring. Preferred is 5-membered divalent aromatic heterocyclic group, which is exemplified by divalent groups of tetrazole ring, oxadiazole ring, thiadiazole ring, triazole ring, oxazole ring, isoxazole ring, thiazole ring, isothiazole ring, imidazole ring, pyrazole ring, pyrrole ring, furan ring and thiophene ring. Particularly preferred are divalent groups of oxadiazole ring, thiadiazole ring and triazole ring.

"Cycloalkylene" is that having 3 to 7 carbon atoms, namely, divalent cycloalkyl, which is specifically exemplified by cyclopropylene, cyclobutylene, cyclopentylene, cyclohexylene and cycloheptylene. Preferred is cycloalkylene having 5 or 6 carbon atoms, which is exemplified by cyclopentylene and cyclohexylene.

"Arylene" is exemplified by phenylene, naphthylene, anthrylene, phenanthrylene and biphenylene, with preference given to phenylene, naphthylene and biphenylene.

"Divalent heterocyclic group which has one or more hetero atom(s) selected from the group consisting of a nitrogen atom, sulfur atom and oxygen atom, and which optionally forms a fused ring" is specifically exemplified by divalent heterocyclic groups of dioxolane ring, dithiol ring, pyrrolidine ring, morpholine ring, oxazine ring, piperazine ring, piperidine ring, pyrroline ring, imidazolidine ring, imidazoline ring, pyrazolidine ring, pyrazoline ring, thiatriazole ring, tetrazole ring, oxadiazole ring, thiadiazole ring, triazole ring, isoxazole ring, oxazole ring, thiazole ring, imidazole ring, pyrazole ring, pyrrole ring, furan ring, thiophene ring, tetrazine ring, triazine ring, pyrazine ring, pyridazine ring, pyrimidine ring, pyridine ring, furoisoxazole ring, imidazothiazole ring, thienoisothiazole ring, thienothiazole ring, imidazopyrazole ring, cyclopentapyrazole ring, pyrrolopyrrole ring, thienothiophene ring, thiadiazolopyrimidine ring, thiazolothiazine ring, thiazolopyrimidine ring, thiazolopyridine ring, oxazolopyrimidine ring, oxazolopyridine ring, benzoxazole ring, benzisothiazole ring, benzothiazole ring, imidazopyrazine ring, purine ring, pyrazolopyrimidine ring, imidazopyridine ring, benzimidazole ring, indazole ring, benzoxathiole ring, benzodioxole ring, benzodithiol ring, indolizine ring, indoline ring, isoindoline ring, furopyrimidine ring, furopyridine ring, benzofuran ring, isobenzofuran ring, thienopyrimidine ring, thienopyridine ring, benzothiophene ring, cyclopentaoxazine ring, cyclopentafuran ring, benzoxazine ring, benzothiazine ring, quinazoline ring, naphthyridine ring, quinoline ring, isoquinoline ring, benzopyran ring, pyridopyridazine ring and pyridopyrimidine ring. Preferred are divalent heterocyclic groups of piperazine ring, piperidine ring, pyridine ring, benzoxazole ring, benzisothiazole ring, benzothiazole ring and benzimidazole ring.

"Alkoxycarbonyl" is linear or branched alkoxycarbonyl having 2 to 7 carbon atoms, which is exemplified by methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, isohexyloxycarbonyl and neohexyloxycarbonyl, with preference given to linear or branched alkoxycarbonyl having 2 to 5 carbon atoms, such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl.

"Lower alkoxycarbonyl" is linear or branched alkoxycarbonyl having 2 to 5 carbon atoms, which is exemplified by methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl, with preference given to methoxycarbonyl and ethoxycarbonyl.

"Acyl" specifically means, for example, formyl, acetyl, propionyl, butyryl, isobutyryl, valeryl, isovaleryl, pivaloyl, caproyl, isocaproyl, acryloyl, propioloyl, methacryloyl, crotonoyl, isocrotonoyl, benzoyl, naphthoyl, toluoyl, hydroatropoyl, atropoyl, cinnamoyl, furoyl, glyceroyl, tropoyl, benziloyl, salicyloyl, anisoyl, vanilloyl, veratroyl, piperonyloyl, protocatechuoyl or galloyl, with preference given to formyl, acetyl, propionyl, butyryl, isobutyryl, valeryl, isovaleryl, pivaloyl, benzoyl and naphthoyl.

"Acyloxy" is that having the above-mentioned acyl, which is exemplified by formyloxy, acetyloxy, propionyloxy, butyryloxy, isobutyryloxy, valeryloxy, isovaleryloxy, pivaloyloxy, caproyloxy, isocaproyloxy, acryloyloxy, propioloyloxy, methacryloyloxy, crotonoyloxy, isocrotonoyloxy, benzoyloxy, naphthoyloxy, toluoyloxy, hydroatropoyloxy, atropoyloxy, cinnamoyloxy, furoyloxy, glyceroyloxy, tropoyloxy, benziloyloxy, salicyloyloxy, anisoyloxy, vanilloyloxy, veratroyloxy, piperonyloyloxy, protocatechuoyloxy and galloyloxy, with preference given to formyloxy, acetyloxy, propionyloxy, butyryloxy, isobutyryloxy, valeryloxy, isovaleryloxy, pivaloyloxy, benzoyloxy and naphthoyloxy.

"Heterocyclic group having one or more hetero atom(s) selected from the group consisting of a nitrogen atom, sulfur atom and oxygen atom" at $R^6$ is 3- to 7-membered heterocyclic group having one or more hetero atom(s) selected from the group consisting of a nitrogen atom, sulfur atom and oxygen atom, which is exemplified by aziridinyl, oxiranyl, azetyl, azetidinyl, oxetanyl, thiatriazolyl, tetrazolyl, dithiazolyl, oxadiazolyl, thiadiazolyl, triazolyl, oxazolyl, isooxazolyl, thiazolyl, isothiazolyl, imidazolyl, pyrazolyl, dioxolanyl, pyrrolyl, pyrrolidinyl, furanyl, thienyl, tetrazinyl, dithiadiazinyl, thiadiazinyl, triazinyl, morpholinyl, morpholino, oxazinyl, thiazinyl, piperazinyl, pyrazinyl, pyridazinyl, pyrimidinyl, piperidyl, piperidino, pyridyl, pyranyl, thiopyranyl, dioxazepinyl, diazepinyl and azepinyl. Preferred is 5- or 6-membered heterocyclic group, which is exemplified by thiatriazolyl, tetrazolyl, dithiazolyl, oxadiazolyl, thiadiazolyl, triazolyl, oxazolyl, isooxazolyl, thiazolyl, isothiazolyl, imidazolyl, pyrazolyl, dioxolanyl, pyrrolyl, pyrrolidinyl, furanyl, thienyl, tetrazinyl, dithiadiazinyl, thiadiazinyl, triazinyl, morpholinyl, morpholino, oxazinyl, thiazinyl, piperazinyl, pyrazinyl, pyridazinyl, pyrimidinyl, piperidyl, piperidino, pyridyl, pyranyl and thiopyranyl. Particularly preferred are pyrrolyl, furanyl, thienyl, piperazinyl, piperidyl, piperidino and pyridyl.

"Aromatic heterocyclic group having one or more hetero atom(s) selected from the group consisting of a nitrogen atom, sulfur atom and oxygen" is 5- or 6-membered aromatic heterocyclic group having one or more hetero atom(s) selected from the group consisting of a nitrogen atom, sulfur atom and oxygen atom, which is exemplified by tetrazolyl, oxadiazolyl, thiadiazolyl, triazolyl, oxazolyl, isooxazolyl, thiazolyl, isothiazolyl, imidazolyl, pyrazolyl, pyrrolyl, furanyl, thienyl, tetrazinyl, triazinyl, pyrazinyl, pyridazinyl, pyrimidinyl and pyridyl. Preferred is 5-membered aromatic heterocyclic group, which is exemplified by tetrazolyl, oxadiazolyl, thiadiazolyl, triazolyl, oxazolyl, isooxazolyl, thiazolyl, isothiazolyl, imidazolyl, pyrazolyl, pyrrolyl, furanyl and thienyl. Particularly preferred are oxadiazolyl, thiadiazolyl and triazolyl.

"Alkoxyalkoxy" is that wherein linear or branched alkoxy having 1 to 6 carbon atoms has been substituted by linear or branched alkoxy having 1 to 6 carbon atoms, and is exemplified by methoxymethoxy, ethoxymethoxy, propoxymethoxy, isopropoxymethoxy, butoxymethoxy, isobutoxymethoxy, sec-butoxymethoxy, tert-butoxymethoxy, pentyloxymethoxy, isopentyloxymethoxy, neopentyloxymethoxy, tert-pentyloxymethoxy, hexyloxymethoxy, isohexyloxymethoxy, neohexyloxymethoxy, tert-hexyl-oxymmthoxy, methoxyethoxy, ethoxyethoxy, propoxyethoxy, isopropoxyethoxy, butoxyethoxy, isobutoxyethoxy, sec-butoxyethoxy, tert-butoxy-ethoxy, pentyloxyethoxy, isopentyloxyethoxy, neopentyloxyethoxy, tert-pentyloxyethoxy, hexyloxyethoxy, isohexyloxyethoxy, neohexyloxyethoxy, tert-hexyloxyethoxy, methoxypropoxy, ethoxypropoxy, propoxypropoxy, isopropoxypropoxy, butoxypropoxy, isobutoxypropoxy, sec-butoxypropoxy, tert-butoxypropoxy, pentyloxypropoxy, isopentyloxypropoxy, neopentyloxypropoxy, tert-pentyloxypropoxy, hexyloxypropoxy, isohexyloxypropoxy, neohexyloxypropoxy, tert-hexyloxypropoxy, methoxybutoxy, ethoxybutoxy, propoxybutoxy, isopropoxybutoxy, butoxybutoxy, isobutoxybutoxy, sec-butoxybutoxy, tert-butoxybutoxy, pentyloxybutoxy, isopentyloxybutoxy, neopentyloxybutoxy, tert-pentyloxybutoxy, hexyloxybutoxy, isohexyloxy-butoxy, neohexyloxybutoxy, tert-hexyloxybutoxy, methoxypentyloxy, ethoxypentyloxy, propoxypentyloxy, isopropoxypentyloxy, butoxypentyloxy, isobutoxypentyloxy, sec-butoxypentyloxy, tert-butoxypentyloxy, pentyloxypentyloxy, isopentyloxypentyloxy, neopentyloxypentyloxy, tert-pentyloxypentyloxy, hexyloxypentyloxy, isohexyloxypentyloxy, neo-hexyloxypentyloxy, tert-hexyloxypentyloxy, methoxyhexyloxy, ethoxy-hexyloxy, propoxyhexyloxy, isopropoxyhexyloxy, butoxyhexyloxy, iso-butoxyhexyloxy, sec-butoxyhexyloxy, tert-butoxyhexyloxy, pentyloxy-hexyloxy, isopentyloxyhexyloxy, neopentyloxyhexyloxy, tert-pentyloxy-hexyloxy, hexyloxyhexyloxy, isohexyloxyhexyloxy, neohexyloxyhexyloxy and tert-hexyloxyhexyloxy. Preferred is that wherein linear or branched alkoxy having 1 to 4 carbon atoms has been substituted by linear or branched alkoxy having 1 to 4 carbon atoms, and is exemplified by methoxymethoxy, ethoxymethoxy, propoxymethoxy, isopropoxymethoxy, butoxymethoxy, isobutoxymethoxy, sec-butoxymethoxy, tert-butoxymethoxy, methoxyethoxy, ethoxyethoxy, propoxyethoxy, isopropoxyethoxy, butoxy-ethoxy, isobutoxyethoxy, sec-butoxyethoxy, tert-butoxyethoxy, methoxy-propoxy, ethoxypropoxy, propoxypropoxy, isopropoxypropoxy, butoxy-propoxy, isobutoxypropoxy, sec-butoxypropoxy, tert-butoxypropoxy, methoxybutoxy, ethoxybutoxy, propoxybutoxy, isopropoxybutoxy, butoxybutoxy, isobutoxybutoxy, sec-butoxybutoxy and tert-butoxybutoxy.

"Lower alkoxy lower alkoxy" is that wherein linear or branched alkoxy having 1 to 4 carbon atoms has been substituted by linear or branched alkoxy having 1 to 4 carbon atoms, and is exemplified by methoxymethoxy, ethoxymethoxy, propoxymethoxy, isopropoxymethoxy, butoxymethoxy, isobutoxymethoxy, sec-butoxymethoxy, tert-butoxymethoxy, methoxyethoxy, ethoxyethoxy, propoxyethoxy, isopropoxyethoxy, butoxyethoxy, isobutoxyethoxy, sec-butoxyethoxy, tert-butoxyethoxy, methoxypropoxy, ethoxypropoxy, propoxypropoxy, isopropoxypropoxy, butoxypropoxy, isobutoxypropoxy, sec-butoxypropoxy, tert-butoxypropoxy, methoxybutoxy, ethoxybutoxy, propoxybutoxy, isopropoxybutoxy, butoxybutoxy, isobutoxybutoxy, sec-butoxybutoxy and tert-butoxybutoxy, with preference given to methoxymethoxy, ethoxymethoxy, methoxyethoxy and ethoxyethoxy.

"Heterocyclic group having one or more hetero atom(s) selected from the group consisting of a nitrogen atom, sulfur atom and oxygen" at $R^{12}$ means 3- to 7-membered heterocyclic group having one or more hetero atom(s) selected from the group consisting of a nitrogen atom, sulfur atom and oxygen, and is exemplified by aziridinyl, oxiranyl, azetyl, azetidinyl, oxetanyl, thiatriazolyl, tetrazolyl, dithiazolyl, oxadiazolyl, thiadiazolyl, triazolyl, oxazolyl, isooxazolyl, thiazolyl, isothiazolyl, imidazolyl, pyrazolyl, dioxolanyl, pyrrolyl, pyrrolidinyl, furanyl, thienyl, tetrazinyl, dithiadiazinyl, thiadiazinyl, triazinyl, morpholinyl, morpholino, oxazinyl, thiazinyl, piperazinyl, pyrazinyl, pyridazinyl, pyrimidinyl, piperidyl, piperidino, pyridyl, pyranyl, thiopyranyl, dioxazepinyl, diazepinyl and azepinyl. Preferred is 5- or 6-membered heterocyclic group, such as thiatriazolyl, tetrazolyl, dithiazolyl, oxadiazolyl, thiadiazolyl, triazolyl, oxazolyl, isooxazolyl, thiazolyl, isothiazolyl, imidazolyl, pyrazolyl, dioxolanyl, pyrrolyl, pyrrolidinyl, furanyl, thienyl, tetrazinyl, dithiadiazinyl, thiadiazinyl, triazinyl, morpholinyl, morpholino, oxazinyl, thiazinyl, piperazinyl, pyrazinyl, pyridazinyl, pyrimidinyl, piperidyl, piperidino, pyridyl, pyranyl and thiopyranyl. Particularly preferred are pyrrolyl, piperazinyl, piperidyl, piperidino and pyridyl.

"Alkenyl" is linear or branched alkenyl having 2 to 6 carbon atoms, which is exemplified by allyl, vinyl, propenyl, isopropenyl, 1-methyl-2-propenyl, 2-methyl-2-propenyl, 1-methyl-1-butenyl, crotyl, 1-methyl-3-butenyl, 3-methyl-2-butenyl, 1-pentenyl, 1-methyl-2-pentenyl, 4-pentenyl, 1-hexenyl, 3-hexenyl and 4-hexenyl.

"Alkynyl" is linear or branched alkynyl having 2 to 6 carbon atoms, which is exemplified by propargyl, 2-butynyl, 1-methyl-2-butynyl, 2-pentynyl, 1-methyl-3-pentynyl, 1-methyl-4-pentynyl, 1-hexynyl and 5-hexynyl.

"Cycloalkylideneamino" specifically means cyclopropylideneamino, cyclobutylideneamino, cyclopentylideneamino, cyclohexylideneamino and cycloheptylideneamino, with preference given to cyclopentylideneamino and cyclohexylideneamino.

"Alkoxy" of the substituted alkoxy at R is linear or branched alkoxy having 1 to 6 carbon atoms, which is exemplified by methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy, with preference given to linear alkoxy, such as methoxy, ethoxy, propoxy, butoxy, pentyloxy and hexyloxy. Particularly preferred is linear alkoxy having 1 to 4 carbon atoms, which is exemplified by methoxy, ethoxy, propoxy and butoxy.

"Alkylthio" of the substituted alkylthio at R is linear or branched alkylthio having 1 to 6 carbon atoms, which is exemplified by methylthio, ethylthio, propylthio, isopropylthio, butylthio, isobutylthio, sec-butylthio, tert-butylthio, pentylthio, isopentylthio, neopentylthio, tert-pentylthio, hexylthio, isohexylthio and neohexylthio, with preference given to linear alkylthio such as methylthio, ethylthio, propylthio, butylthio, pentylthio and hexylthio. Particularly preferred is linear alkylthio having 1 to 4 carbon atoms, which is exemplified by methylthio, ethylthio, propylthio and butylthio.

"Optionally substituted" of "optionally substituted non-aromatic heterocyclic group containing nitrogen" means that the group may be substituted by 1 to 3 substituent(s) and said substituents may be the same or different. The position of the substituent(s) is optional and is not particularly limited. Specific examples of the substituents include the above-mentioned lower alkyl, the above-mentioned halogenated lower alkyl, the above-mentioned cycloalkyl, the above-mentioned aralkyl, the above-mentioned aryl, and the above-mentioned amino-protecting group. Preferred are lower alkyl and amino-protecting group.

"Optionally substituted" of "optionally substituted linear or branched alkylene which may have one or more double bond(s) or triple bond(s) in the chain" means that the group may be substituted by one or more substituent(s). Examples of the substituents include the above-mentioned halogen atom, hydroxy, amino which may be substituted by a substituent selected from the group consisting of the above-mentioned lower alkyl, the above-mentioned halogenated lower alkyl, the above-mentioned cycloalkyl, the above-mentioned aralkyl, the above-mentioned aryl and the above-mentioned amino protecting group, the above-mentioned lower alkoxy, the above-mentioned aralkyl and the above-mentioned cycloalkyl.

"Optionally substituted" of "optionally substituted alkoxy" and "optionally substituted alkylthio" at $R^{11}$ means that the group may be substituted by one or more substituent (s), and said substituents may be the same or different. The position of the substituent(s) is optional and is not particularly limited. Specific examples of the substituents include the above-mentioned halogen atom, the above-mentioned lower alkoxy, the above-mentioned alkylthio, amino which may be substituted by the above-mentioned lower alkyl or the above-mentioned acyl, carboxy, the above-mentioned alkoxycarbonyl, the above-mentioned acyl, the above-mentioned acyloxy, the above-mentioned aryl, the above-mentioned aryloxy, the above-mentioned arylthio, the above-mentioned aryloxycarbonyl, the above-mentioned aralkyloxy, and the above-mentioned aralkyloxycarbonyl. Preferred are amino, lower alkoxy, halogen atom, carboxy, alkoxycarbonyl and aralkyloxycarbonyl.

"Optionally substituted" of "optionally substituted aryl", "optionally substituted cycloalkyl", "optionally substituted aryloxy", "optionally substituted aralkyloxy" and "optionally substituted arylthio" at $R^{11}$ means that they may have 1 to 3 substituent(s) on the ring wherein said substituents may be the same or different. The position of the substituent(s) is optional and is not particularly limited. Specific examples of the substituents include the above-mentioned lower alkyl, the above-mentioned halogen atom, the above-mentioned lower alkoxy, the above-mentioned alkylthio, amino which may be substituted by the above-mentioned lower alkyl or the above-mentioned acyl, carboxy, the above-mentioned alkoxycarbonyl, the above-mentioned acyl, the above-mentioned acyloxy, the above-mentioned aryl, the above-mentioned aryloxy, the above-mentioned arylthio, the above-mentioned aryloxycarbonyl, the above-mentioned aralkyloxy and the above-mentioned aralkyloxycarbonyl. Preferred are lower alkyl, amino, lower alkoxy, halogen atom, carboxy, alkoxycarbonyl and aralkyloxycarbonyl. Particularly preferred is lower alkyl.

"Optionally substituted" of "optionally substituted aralkyl" at $R^5$ means that it may have 1 to 3 substituent(s) on aryl wherein said substituents may be the same or different. The position of the substituent(s) is optional and is not particularly limited. Specific examples of the substituents include the above-mentioned lower alkyl, the above-mentioned lower alkoxy, the above-mentioned acyl, amino which may be substituted by the above-mentioned lower alkyl or the above-mentioned acyl, the above-mentioned alkoxycarbonyl, the above-mentioned aryloxycarbonyl, the above-mentioned aryloxy, the above-mentioned alkylthio, the above-mentioned arylthio, the above-mentioned aryl, and the above-mentioned halogen atom. Preferred are lower alkyl, lower alkoxy and halogen atom. Particularly preferred is lower alkyl. "Optionally substituted" of "optionally substituted lower alkyl", "optionally substituted lower alkoxy" and "optionally substituted lower alkylthio" at $R^6$ means that the group may be substituted by one or more substituent(s) and said substituents may be the same or different. The position of the substituent(s) is optional and is not particularly limited. Specific examples of the substituents include the above-mentioned halogen atom, hydroxy, the above-mentioned alkoxy, the above-mentioned aryloxy, amino which may be substituted by the above-mentioned lower alkyl or the above-mentioned acyl, mercapto, the above-mentioned alkylthio, the above-mentioned arylthio, carboxy, the above-mentioned alkoxycarbonyl, the above-mentioned aryloxycarbonyl, carbamoyl, the above-mentioned halogenated lower alkyl, sulfamoyl, cyano, nitro, alkylsulfonyl such as methylsulfonyl, ethylsulfonyl, isopropylsulfonyl, alkylsulfinyl such as methylsulfinyl, ethylsulfinyl and isopropylsulfinyl, and arylsulfonyl such as phenylsulfonyl. Preferred are halogen atom, hydroxy, alkoxy, amino, carboxy and alkoxycarbonyl.

"Optionally substituted" of "optionally substituted aryl", "optionally substituted cycloalkyl" and "optionally substituted heterocyclic group having one or more hetero atom(s) selected from the group consisting of a nitrogen atom, sulfur atom and oxygen atom" at $R^6$ means that the group may be substituted by one or more substituent(s) and said substituents may be the same or different. The position of the substituent(s) is optional and is not particularly limited. Specific examples of the substituents include the above-mentioned lower alkyl, the above-mentioned halogen atom, hydroxy, the above-mentioned alkoxy, the above-mentioned aryloxy, amino which may be substituted by the above-mentioned lower alkyl or the above-mentioned acyl, mercapto, the above-mentioned alkylthio, the above-mentioned arylthio, carboxy, the above-mentioned alkoxycarbonyl, the above-mentioned aryloxycarbonyl, carbamoyl, the above-mentioned halogenated lower alkyl, sulfamoyl, cyano, nitro, alkylsulfonyl such as methylsulfonyl, ethylsulfonyl and isopropylsulfonyl, alkylsulfinyl such as methylsulfinyl, ethylsulfinyl and isopropylsulfinyl, and arylsulfonyl such as phenylsulfonyl. Preferred are lower alkyl, halogen atom, hydroxy, alkoxy, amino, carboxy and alkoxycarbonyl.

"Optionally substituted" of "optionally substituted alkyl" at $R^7$ means that the group may be substituted by one or more substituent(s) and said substituent(s) may be the same or different. The position of the substituent(s) is optional and is not particularly limited. Specific examples of the substituents include hydroxy, the above-mentioned lower alkoxy, mercapto, the above-mentioned lower alkylthio, carboxy, the above-mentioned lower alkoxycarbonyl, halogen atom, and amino which may be substituted by the above-mentioned lower alkyl or the above-mentioned acyl. Preferred are hydroxy, halogen atom and lower alkoxy.

"Optionally substituted" of "optionally substituted aryl" and "optionally substituted aromatic heterocyclic group having one or more hetero atom(s) selected from the group consisting of a nitrogen atom, sulfur atom and oxygen atom" at $R^7$ means that they may have 1 to 3 substituent(s) on the ring wherein said substituents may be the same or different. The position of the substituent(s) is optional and is not particularly limited. Specific examples of the substituents include the above-mentioned lower alkyl, hydroxy, the above-mentioned lower alkoxy, mercapto, the above-mentioned lower alkylthio, carboxy, the above-mentioned lower alkoxycarbonyl, halogen atom, and amino which may be substituted by the above-mentioned lower alkyl or the above-mentioned acyl. Preferred are hydroxy, lower alkyl, halogen atom and lower alkoxy.

"Optionally substituted" of "optionally substituted alkenyl" and "optionally substituted alkynyl" at $R^{12}$ means that the group may be substituted by one or more substituent(s) and said substituent(s) may be the same or different. The position of the substituent(s) is optional and is not particularly limited. Specific examples of the substituents include hydroxy, the above-mentioned alkoxy, carboxy, the above-mentioned alkoxycarbonyl, the above-mentioned acyloxy, and amino which may be substituted by the above-mentioned alkyl, the above-mentioned aryl, the above-mentioned aralkyl or the above-mentioned amino-protecting group. Preferred are hydroxy, alkoxy, carboxy, alkoxycarbonyl and acyloxy.

"Optionally substituted" of "optionally substituted cycloalkyl", "optionally substituted aryl" and "optionally substituted heterocyclic group having one or more hetero atom(s) selected from the group consisting of a nitrogen atom, sulfur atom and oxygen atom" at $R^{12}$ means that they may have 1 to 3 substituent(s) on the ring wherein said substituents may be the same or different. The position of the substituent(s) is optional and is not particularly limited. Specific examples of the substituents include hydroxy, the above-mentioned lower alkoxy, mercapto, the above-mentioned lower alkylthio, carboxy, the above-mentioned lower alkoxycarbonyl, the above-mentioned lower alkyl, amino which may be substituted by the above-mentioned lower alkyl, the above-mentioned halogen atom, carbamoyl, cyano, the above-mentioned acyl, nitro, sulfamoyl, alkoxythiocarbonyl, thioalkanoyl, alkylsulfonyl such as methylsulfonyl and ethylsulfonyl, azomethine which may be substituted by the above-mentioned lower alkyl, the above-mentioned aryl or the above-mentioned aralkyl, alkoxyamino such as methoxyamino and isopropoxyamino, hydrazino which may be substituted by the above-mentioned lower alkyl, the above-mentioned aryl or the above-mentioned aralkyl, aminooxy which may be substituted by the above-mentioned lower alkyl, the above-mentioned aryl or the above-mentioned aralkyl, and alkylsulfinyl such as methylsulfinyl. Preferred are hydroxy, lower alkyl, halogen atom, lower alkoxy, amino and carboxy.

"Optionally substituted" of "optionally substituted aralkyl" at $R^{12}$ means that it may have 1 to 3 substituent(s) on aryl wherein said substituents may be the same or different. The position of the substituent(s) is optional and is not particularly limited. Specific examples of the substituents include the above-mentioned lower alkyl, the above-mentioned lower alkoxy, the above-mentioned acyl, amino which may be substituted by the above-mentioned lower alkyl or the above-mentioned acyl, the above-mentioned alkoxycarbonyl, the above-mentioned aryloxycarbonyl, the above-mentioned aryloxy, the above-mentioned alkylthio, the above-mentioned arylthio, the above-mentioned aryl, and the above-mentioned halogen atom. Preferred are lower alkyl, lower alkoxy and halogen atom.

The compounds of the present invention which is shown by the formula (I) can be synthesized by, for example, the following method, to which the synthesis method of the compounds of the present invention is not limited.

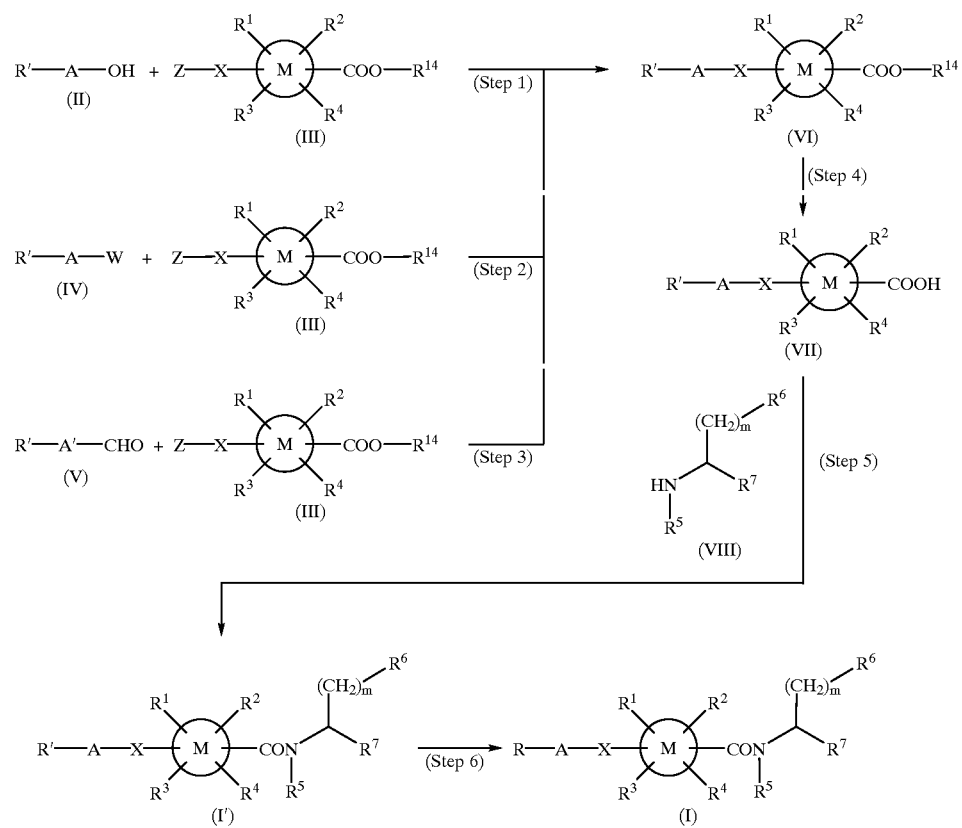

wherein
R' is R protected by hydroxy-protecting group or amino-protecting group, which is more specifically protected $R_a$, protected alkoxy substituted by $R_a$, protected alkylthio substituted by $R_a$, protected alkylamino substituted by $R_a$, protected and optionally substituted non-aromatic heterocyclic group containing nitrogen, or protected hydroxy,
  wherein when R is dimethylamino, N-methylpiperazinyl or N-methylpiperidyl, R' means R itself, since R does not need to be protected,
  wherein $R_a$ is amino, guanidino, amidino, carbamoyl, ureido, thioureido, hydrazino, hydrazinocarbonyl or imino, these groups being optionally substituted by a substituent selected from the group consisting of lower alkyl, halogenated lower alkyl, cycloalkyl, aralkyl, aryl and amino-protecting group;

$R^{14}$ is carboxy-protecting group such as methyl, ethyl, tert-butyl, allyl, phenyl, benzyl, trichloroethyl, p-nitrobenzyl, trimethyl-silyl, tert-butyldimethylsilyl, methoxymethyl and 2-trimethyl-silylethyl;

W is halogen atom;

A' is A without one end methylene;

Z is hydrogen atom or substituent which activates X such as triphenylphosphonium, triphenylphosphonate and arylsulfonyl; and A, X, M, m, R, $R^1$, $R^2$, $R^3$, $R^4$, $R^5$, $R^6$ and $R^7$ are as defined above.

(Step 1)

The compound (VI) can be synthesized by reacting compound (II) and compound (III) in the presence of a combined condensing agent of triphenylphosphine, trimethylphosphine, triethylphosphine, triphenyl phosphite, trimethyl phosphite, triethyl phosphite, and the like, and diisopropyl azodicarboxylate, diethyl azodicarboxylate, dicyclohexyl azodicarboxylate, and the like, in an organic solvent such as ether, tetrahydrofuran, dioxane, dichloromethane, chloroform, benzene, toluene and dimethylformamide, or a mixed solvent thereof, under ice-cooling to under heating.

This method is particularly preferable when X is oxygen atom or sulfur atom.

The compound (VI) can be also synthesized by the following method.

(Step 2)

The compound (VI) can be synthesized by reacting compound (IV) and compound (III) in the presence of a base such as sodium hydride, potassium hydride, lithium hydride, potassium carbonate, sodium carbonate, potassium tert-butoxide, lithium diisopropylamide, methyllithium, n-butyllithium, sec-butyllithium and tert-butyllithium, in an organic solvent such as dimethylformamide, methylene chloride, tetrahydrofuran, ether, benzene and toluene, or a mixed solvent thereof, at a temperature of from −78° C. to under heating.

This method is particularly preferable when X is sulfur atom or oxygen atom.

When X is —SO— or —SO$_2$—, the corresponding sulfide obtained in the above Step 1 or Step 2 is oxidized with an oxidizing agent such as hydrogen peroxide, peracetic acid, metaperiodate, metachloroperbenzoic acid, acyl nitrate and dinitrogen tetraoxide, to synthesize compound (VI).

The compound (VI) wherein X is particularly —NR$^8$— or —CR$^9$R$^{10}$— can be also synthesized by the following method.

(Step 3)

The compound (VI) can be synthesized by condensing compound (V) and compound (III) in the presence of a suitable base (e.g., lithium diisopropylamide, lithium bis(trimethylsilyl)amide, potassium bis(trimethylsilyl)amide, n-butyllithium, potassium tert-butoxide, sodium hydroxide, potassium hydroxide, sodium hydride and potassium hydride) as necessary, in water or an organic solvent such as methanol, ethanol, dimethylformamide, ether, dioxane, tetrahydrofuran, ethyl acetate, diisopropyl ether, dimethoxyethane, toluene, hexane and dimethyl sulfoxide, or a mixed solvent thereof, and subjecting the obtained compound to catalytic reduction using hydrogen gas in the presence of a metallic catalyst such as platinum black, platinum oxide, palladium black, palladium oxide, palladium hydroxide, palladium carbon and Raney nickel, or treating the compound with a reducing agent such as sodium borohydride, sodium cyanoborohydride, trimethylsilane, triethylsilane, alkali metal-ammonia, alkali metal-ethylamine, sodium amalgam and potassium amalgam.

The compound (I) can be synthesized by subjecting compound (VI) obtained in the above Step 1, 2 or 3 to the following Steps 4–6.

(Step 4)

The compound (VII) can be synthesized by reacting compound (VI) in the presence of a hydroxide or carbonate of alkali metal such as sodium, potassium and lithium, or a base such as 1,5-diazabicyclo[4.3.0]non-5-ene and 1,8-diazabicyclo[5.4.0]undec-7-ene, or an acid such as hydrochloric acid, hydrobromic acid, sulfuric acid, hydrogen chloride, hydrogen bromide, hydrogen fluoride, acetic acid and trifluoroacetic acid, in water or an organic solvent such as methanol, ethanol, dichloromethane, chloroform, tetrahydrofuran, toluene and xylene or a mixed solvent thereof, under ice-cooling to under heating, or by subjecting compound (VI) to catalytic reduction using hydrogen gas in an organic solvent such as methanol, ethanol, dimethylformamide, ether, dioxane, tetrahydrofuran and acetic acid or a mixed solvent thereof, in the presence of a metallic catalyst such as platinum black, platinum oxide, palladium black, palladium oxide, palladium carbon and Raney nickel, or by reacting compound (VI) in the presence of quaternary ammonium fluoride such as tetraethylammonium fluoride and tetra-n-butylammonium fluoride, in an organic solvent such as tetrahydrofuran, dimethylformamide and dimethyl sulfoxide or a mixed solvent thereof, under ice-cooling to under heating.

(Step 5)

The compound (I') can be synthesized by reacting compound (VII) and compound (VIII) using a condensing agent such as 1-ethyl-3-(3-dimethylaminopropyl)carbodiimide hydrochloride (WSC.HCl), dicyclohexylcarbodiimide (DCC), diphenylphosphoryl azide (DPPA) and carbonyldiimidazole (CDI), in the presence of an activating agent such as 1-hydroxybenzotriazole (HOBT), hydroxysuccinimide (HOSu) and N-hydroxy-5-norbornene-2,3-dicarboximide (HONB) as necessary, in an organic solvent such as dimethylformamide, dichloromethane, chloroform, acetonitrile, tetrahydrofuran, dimethyl sulfoxide, carbon tetrachloride and toluene or a mixed solvent thereof, under ice-cooling to under heating. When compound (VIII) is, for example, hydrochloride, this reaction can be carried out in the presence of a base such as triethylamine, N-methylmorpholine and 4-dimethylaminopyridine. When R$^7$ is a group having hydroxy, such as —CONHOH and —CH$_2$OH, compound (VIII) wherein said hydroxy is protected in advance is used.

(Step 6)

This step aims at eliminating the hydroxy-protecting group or amino-protecting group at R', and can be carried out according to a suitable known method. For example, when the amino-protecting group at R' is Boc (tert-butoxycarbonyl group), compound (I') is reacted in the presence of an acid such as hydrochloric acid, hydrobromic acid, trifluoroacetic acid, p-toluenesulfonic acid, methanesulfonic acid, hydrogen chloride-dioxane, hydrogen chloride-ether and hydrogen chloride-ethyl acetate, in water or an organic solvent such as dioxane, ether, dichloromethane, tetrahydrofuran, methanol, ethanol, chloroform, benzene, toluene and ethyl acetate or a mixed solvent thereof or without solvent, to give compound (I). When the amino protecting group is, for example, benzyloxycarbonyl group, compound (I) can be synthesized by catalytic hydrogenation using hydrogen gas in water or an organic solvent such as methanol, ethanol, dimethylformamide, ether, dioxane, tetrahydrofuran and acetic acid or a mixed solvent thereof, in the presence of a metallic catalyst such as palladium carbon, platinum oxide and Raney nickel. When R' is hydroxy protected by hydroxy-protecting group, compound (I) can be synthesized by a conventional method such as catalytic hydrogenation. When $R^7$ is protected at hydroxy, the hydroxy-protecting group is eliminated by a conventional method such as catalytic hydrogenation, and thereafter or simultaneously therewith, the above Step is carried out.

The compound (I) wherein $R^7$ is carboxyl group can be synthesized by, for example, subjecting compound (I') wherein $R^7$ is tert-butoxy-carbonyl group or benzyloxycarbonyl group to the above-mentioned reaction.

(Step 8)

The compound (VI) can be synthesized using compound (XI) and compound (XII) according to the method of the above-mentioned Step 7.

When X is a divalent aromatic heterocyclic group having one or more hetero atoms selected from nitrogen atom, sulfur atom and oxygen atom, such as divalent oxadiazole ring, compound (VI) can be also synthesized by the following method.

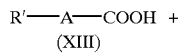

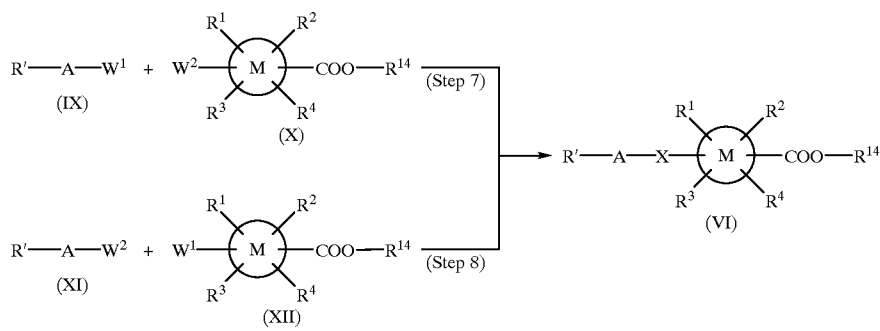

wherein
$W^1$ is —$COW^3$, —$SO_2W^3$ or —O—$COW^3$
   wherein $W^3$ is hydroxy or halogen atom;
$W^2$ is hydroxy, mercapto or —$NR^8H$
   wherein $R^8$ is as defined above; and
A, X, M, $R^1$, $R^1$, $R^2$, $R^3$, $R^4$ and $R^{14}$ are as defined above.

The compound (VI) wherein X is —COO—, —$CONR^8$—, —$SO_2NR^8$—, —COS—, —OOC—$NR^8$— or —O—CO—O— can be also synthesized by the following method.

(Step 7)

The compound (VI) can be synthesized by reacting compound (IX) and compound (X) using a condensing agent such as WSC.HCl, DCC, DPPA and CDI, in the presence of an activating agent such as HOBT, HOSu and HONB as necessary, in an organic solvent such as dimethylformamide, dichloromethane, chloroform, acetonitrile, tetrahydrofuran, dimethyl sulfoxide, carbon tetrachloride and toluene or a mixed solvent thereof, under ice-cooling to under heating (this reaction can be carried out in the presence of a base such as triethylamine, N-methylmorpholine, pyridine, 4-dimethylaminopyridine and N-methylpiperidine), or in the presence of a hydroxide or carbonate of alkali metal such as sodium, potassium and lithium, or a base such as triethylamine, pyridine, N-methylmorpholine, N-methylpiperidine and 4-dimethylaminopyridine, in water or an organic solvent such as dimethylformamide, dichloromethane, chloroform, tetrahydrofuran, dimethyl sulfoxide, benzene and toluene or a mixed solvent thereof, under ice-cooling to under heating.

The compound (VI) wherein X is —OOC—, —$NR^8CO$—, —$NR^8SO_2$— or —$NR^8$—COO— can be also synthesized by the following method.

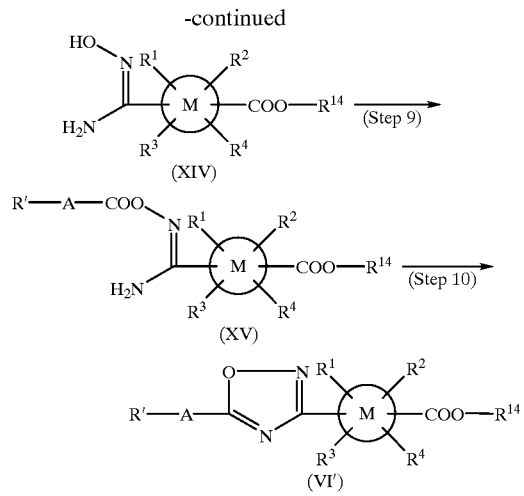

wherein A, M, R', $R^1$, $R^2$, $R^3$, $R^4$ and $R^{14}$ are as defined above.

(Step 9)

The compound (XV) can be synthesized by reacting compound (XIII) and compound (XIV) using a condensing agent such as WSC.HCl, DCC, DPPA and CDI, in the presence of an activating agent such as HOBT, HOSu and HONB as necessary, in an organic solvent such as dimethylformamide, dichloromethane, chloroform, acetonitrile, tetrahydrofuran, dimethyl sulfoxide, carbon tetrachloride and toluene or a mixed solvent thereof, under ice-cooling to under heating. This reaction can be carried out in the presence of a base such as trimethylamine, N-methylmorpholine, pyridine, 4-dimethylaminopyridine and N-methylpiperidine.

(Step 10)

The compound (VI') can be synthesized by heating compound (XV) in an organic solvent such as toluene, dioxane, tetrahydrofuran, benzene and xylene, or a mixed solvent thereof.

The compound (I) can be synthesized by treating compound (VI) and compound (VI') obtained in the above Steps 7, 8 and 10 by the same method as in the above Steps 4–6.

When at least one of $R^1$, $R^2$, $R^3$ and $R^4$ of compound (I) is a halogen atom, compound (I) can be also synthesized by the following method.

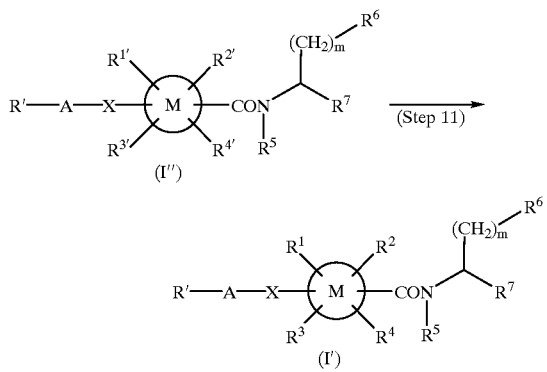

wherein $R^{1\prime}$, $R^{2\prime}$, $R^{3\prime}$ and $R^{4\prime}$ are the same or different and each is hydrogen atom, hydroxy, alkoxy, mercapto, alkylthio, nitro, cyano, carboxy, alkoxycarbonyl, aryloxycarbonyl, acyl, alkyl which may be substituted by a substituent selected from hydroxy, lower alkoxy and halogen atom, amino which may be substituted by a substituent selected from alkyl, aryl, aralkyl and amino-protecting group, or —CO—$R^{11}$ wherein $R^{11}$ is as defined above, provided that at least one of them is hydrogen atom; and A, X, M, m, R', $R^1$, $R^2$, $R^3$, $R^4$, $R^5$, $R^6$ and $R^7$ are as defined above.

(Step 11)

The compound (I') can be synthesized by reacting compound (III) in the presence of a halogenating agent such as tert-butyl hypochlorite, tert-butyl hypobromite, tert-butyl hypoiodite, sulfuryl chloride, sulfuryl bromide, thionyl chloride, thionyl bromide, fluorine, chlorine, bromine, iodine, hydrogen fluoride, silver difluoride and xenon difluoride, in an organic solvent such as dichloromethane, chloroform, acetonitrile, toluene, benzene, ether, tetrahydrofuran, dioxane, methanol, ethanol, carbon tetrachloride and ethyl acetate, or a mixed solvent thereof, or without solvent, under ice-cooling to under heating. When the protective group is removed by this step, a re-protection is applied. In the case of Boc, for example, the compound is protected with di-tert-butyl dicarbonate and the like in the presence of a suitable base such as triethylamine and pyridine.

The compound (I) can be synthesized by treating the obtained compound (I') by the same method as in the above Step 6.

The above Step 11 may be carried out after synthesizing compound (VI) corresponding to compound (III). The subsequent same treatment as in the above Steps 4–6 gives compound (I).

The compound (I) wherein at least one of $R^1$, $R^2$, $R^3$ and $R^4$ is —O—CO—$R^{11}$ can be also synthesized by the following method.

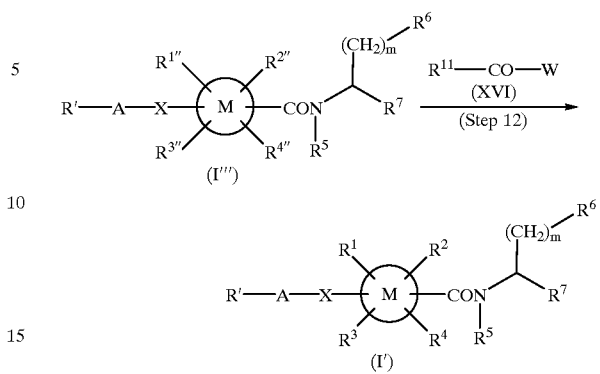

wherein $R^{1\prime\prime}$, $R^{2\prime\prime}$, $R^{3\prime\prime}$ and $R^{4\prime\prime}$ are the same or different and each is hydrogen atom, hydroxy, halogen atom, alkoxy, mercapto, alkylthio, nitro, cyano, carboxy, alkoxycarbonyl, aryloxycarbonyl, acyl, alkyl which may be substituted by a substituent selected from hydroxy, lower alkoxy and halogen atom, or amino which may be substituted by a substituent selected from alkyl, aryl, aralkyl and amino-protecting group, wherein at least one of them is hydroxy; and A, X, M, m, W, R', $R^1$, $R^2$, $R^3$, $R^4$, $R^5$, $R^6$, $R^7$ and $R^{11}$ are as defined above.

(Step 12)

The compound (I') can be synthesized by reacting compound (I''') with compound (XVI) in an organic solvent such as dichloromethane, chloroform, ether, tetrahydrofuran, dioxane, benzene, toluene, dimethylformamide, ethyl acetate and acetonitrile or a mixed solvent thereof, in the presence of a base such as pyridine, triethylamine, N-methylmorpholine, N-methylpiperidine and 4-dimethylaminopyridine.

The compound (I) can be synthesized by reacting the obtained compound (I') by the same method as in the above Step 6.

The compound of the formula (I) of the present invention can be also synthesized by the following synthetic method.

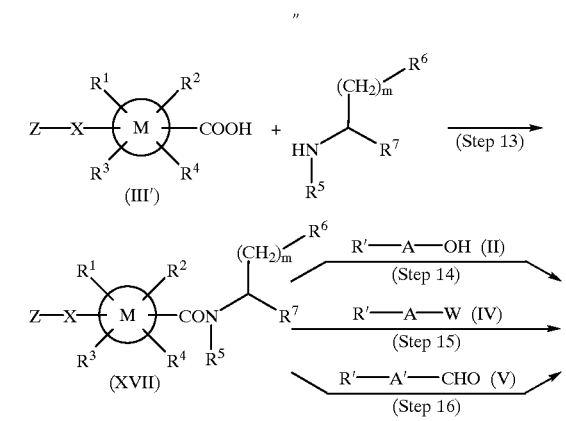

-continued

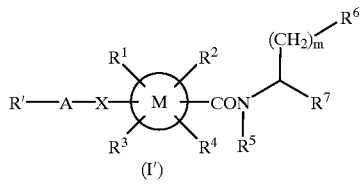

(I')

wherein A, A', X, M, m, W, Z, R', $R^1$, $R^2$, $R^3$, $R^4$, $R^5$, $R^6$ and $R^7$ are as defined above.

(Step 13)

The compound (XVII) can be synthesized by subjecting compound (III') and compound (VIII) to the same reaction as in the above Step 5.

(Step 14)

The compound (I') can be synthesized by subjecting compound (II) and compound (XVII) to the same reaction as in the above Step 1.

The compound (I') can be also synthesized by the following method.

(Step 15)

The compound (I') can be synthesized by subjecting compound (IV) and compound (XVII) to the same reaction as in the above Step 2.

The compound (I') wherein X is —$NR^8$— or —$CR^9R^{10}$— can be also synthesized by the following method.

(Step 16)

The compound (I') can be synthesized by subjecting compound (V) and compound (XVII) to the same reaction as in the above Step 3.

The compound (I) can be synthesized by subjecting compound (I') obtained in the above Steps 14–16 to the same reaction as in the above Step 6.

The compound (I') wherein X is —COO—, —$CONR^8$—, —$SO_2NR^8$—, —COS—, —OOC—$NR^8$— or —O—CO—O— can be also synthesized by the following method.

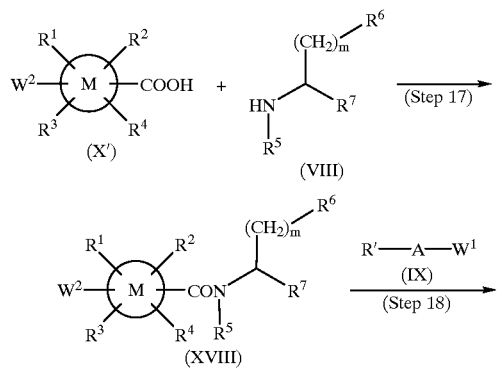

wherein A, X, M, m, $W^1$, $W^2$, R', $R^1$, $R^2$, $R^3$, $R^4$, $R^5$, $R^6$ and $R^7$ are as defined above.

(Step 17)

The compound (XVIII) can be synthesized by subjecting compound (X') and compound (VIII) to the same reaction as in the above Step 5.

(Step 18)

The compound (I') can be synthesized by subjecting compound (IX) and compound (XVIII) to the same reaction as in the above Step 7.

The compound (I') wherein X is —OOC—, —$NR^8CO$—, —$NR^8SO_2$— or —$NR^8$—COO— can be also synthesized by the following method.

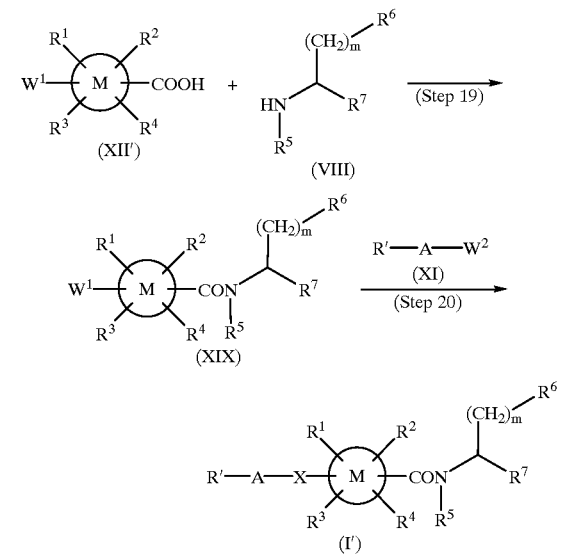

wherein A, X, M, m, $W^1$, $W^2$, R', $R^1$, $R^2$, $R^3$, $R^4$, $R^5$, $R^6$ and $R^7$ are as defined above.

(Step 19)

The compound (XIX) can be synthesized by subjecting compound (XII') and compound (VIII) to the same reaction as in the above Step 5.

(Step 20)

The compound (I') can be synthesized by subjecting compound (XI) and compound (XIX) to the same reaction as in the above Step 8.

The compound (I) can be synthesized by subjecting compound (I') obtained in the above Step 18 and Step 20 to the same reaction as in the above Step 6.

When X is —$CR^9R^{10}$—, —CO—, —C=C— or —CS—, the following step can be used for synthesis.

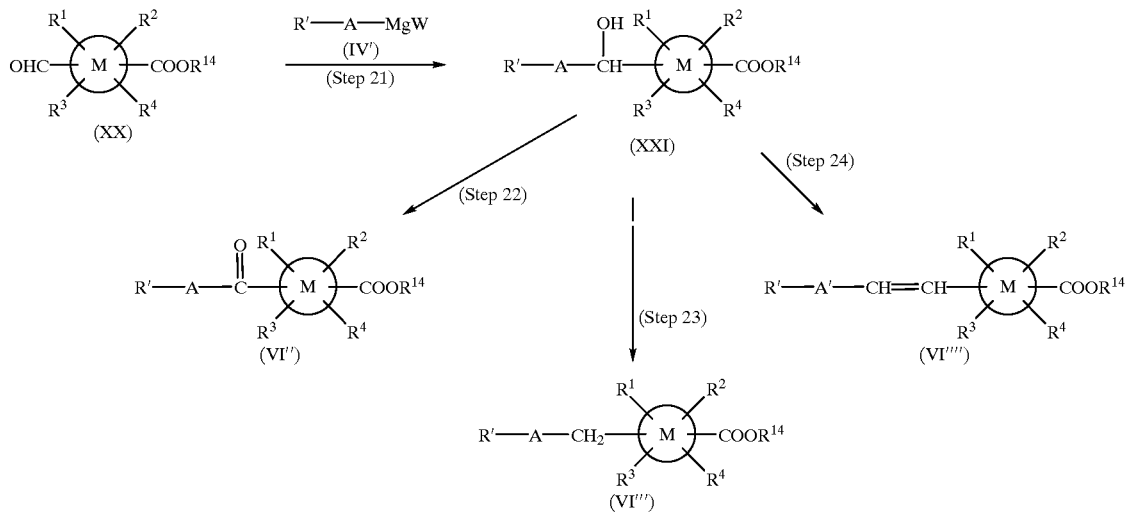

wherein A, A', M, X, m, $W^1$, $W^2$, R', $R^1$, $R^2$, $R^3$, $R^4$, $R^5$, $R^6$, $R^7$ and $R^{14}$ are as defined above.

(Step 21)

The compound (XXI) can be synthesized by reacting the corresponding Grignard reagent (IV') obtained from compound (IV) by a conventional method, with compound (XX) in an organic solvent such as ether, tetrahydrofuran and dioxane or a mixed solvent thereof, at a temperature of from −78° C. to under heating.

(Step 22)

The compound (VI") can be synthesized by reacting compound (XXI) in the presence of an oxidizing agent such as chromic anhydride, pyridinium chlorochromate, manganese dioxide, sodium hypochlorite and ruthenium tetraoxide, in an organic solvent such as ether, tetrahydrofuran and dioxane or a mixed solvent thereof, under ice-cooling to under heating.

The compound (VI") wherein X is —CS— can be synthesized by reacting compound (VI") obtained by the above method, in the presence of hydrogen sulfide, phosphorus pentasulfide, 2,4-bis(4-methoxyphenyl)-1,3-dithia-2,4-diphosphetane-2,4-disulfide (Lawsson's reagent) and the like, in an organic solvent such as benzene, toluene, methanol and ethanol or a mixed solvent thereof, under ice-cooling to under heating.

(Step 23)

The compound (VI''') can be synthesized by reacting compound (XXI) in the presence of a reducing agent such as triethylsilane, lithium alminium hydride-alminium chloride, sodium borohydride-trifluoroborane, sodium cyanoborohydride-methyl iodide and triphenylphosphonium, in an organic solvent such as ether, tetrahydrofuran and dioxane, or a mixed solvent thereof, at a temperature of from −78° C. to under heating.

(Step 24)

The compound (VI"") can be synthesized by reacting compound (XXI) in the presence of sulfuric acid, phosphoric acid, potassium hydrogensulfate, oxalic acid, p-toluenesulfonic acid, boron trifluoride-etherate, thionyl chloride-pyridine, phosphorus oxychloride-pyridine, methanesulfonyl chloride-pyridine, p-toluenesulfonyl chloride-pyridine, and the like, in an organic solvent such as ether, tetrahydrofuran and dioxane, or a mixed solvent thereof, under ice-cooling to under heating.

The compound (I) can be synthesized by treating compound (VI"), (VI''') or (VI"") obtained in the above Steps 22–24 by the same method as in the above Steps 4–6.

The compound of the formula (I) can be converted to a pharmaceutically acceptable acid addition salt by a conventional method by treating same with an inorganic acid (e.g., hydrochloric acid, sulfuric acid, phosphoric acid, hydrobromic acid and nitric acid) or organic acid (e.g., oxalic acid, maleic acid, humaric acid, malic acid, tartaric acid, succinic acid, citric acid, acetic acid, lactic acid, methanesulfonic acid, p-toluenesulfonic acid, benzoic acid, valeric acid, malonic acid, nicotinic acid and propionic acid).

The compound thus obtained can be separated and purified by a known method for separation and purification, such as concentration, concentration under reduced pressure, solvent extraction, precipitation, recrystallization and chromatography.

The compound of the present invention includes one or more stereoisomers due to an asymmetric carbon, and such isomers and mixtures thereof are also encompassed in the present invention. In addition, hydrates and solvates with pharmaceutically acceptable organic solvents, as well as prodrugs of the compound of the present invention are also encompassed in the present invention.

The compound of the present invention shows superior effects of suppressing production of inflammatory cytokines in mammals such as human, rabbit, dog and cat, and is useful for the prophylaxis and treatment of noninfectious or infectious diseases accompanied by neutrophile infiltration, which are represented by rheumatic diseases (e.g., rheumatoid arthritis); arthritis due to gout; systemic lupus erythematosus; dermatopathy (e.g., psoriasis, pustulosis and atopic dermatitis); respiratory diseases (e.g., bronchial asthma, bronchitis, ARDS and diffused interstitial pneumonia); inflammatory enteric diseases (e.g., ulcerative colitis and Crohn's disease); acute or chronic hepatitis inclusive of fulminant hepatitis; acute or chronic glomerulonephritis; nephropyelitis; uveitis caused by Behcet disease and vogt-Koyanagi Harada disease; Mediterranean fever (polyserositis); ischemic diseases (e.g., myocardial infarction); and systemic circulatory failure and multi-organ failure caused by sepsis.

The suppressive effect of the compound of the present invention on inflammatory cytokines such as IL-6 and GM-CSF has been also acknowledged.

When the compound of the formula (I) of the present invention or a pharmaceutically acceptable salt thereof is used as a pharmaceutical preparation comprising same as an active ingredient, it is generally admixed with a pharmaceutically acceptable carrier, excipient, diluent, extender, disintegrator, stabilizer, preservative, buffer, emulsifying agent, aromatic, coloring, sweetener, thickener, flavor, solubilizer and other additives such as water, vegetable oil, alcohols (e.g., ethanol and benzyl alcohol), polyethylene glycol, glycerol triacetate, gelatin, lactose and carbohydrate (e.g., starch), magnesium stearate, talc, lanolin, white petrolatum known Per se to give a pharmaceutical composition in the form of tablet, pill, powder, granule, suppository, injection, eye drop, liquid, capsule, troche, aerosol, elixir, suspension, emulsion, syrup and the like, which is administered orally or parenterally.

While the dose varies depending on the kind and severity of diseases, compound to be administered, administration route, age, sex, body weight etc. of the patients, and so on, when it is orally administered to an adult patient, for example, the daily dose is generally 0.01–1,000 mg, preferably about 0.1–100 mg, and when it is intravenously administered to an adult patient, for example, the daily dose is generally 0.01–1,000 mg, preferably about 0.05–50 mg, which is administered in one or several doses.

The present invention is described in more detail by illustrative Preparative Examples and Examples, to which the present invention is not limited.

Hereunder follow Preparative Examples of the intermediate compounds shown in Table 1.

TABLE 1

| Preparative Example | |
| --- | --- |
| 1 | [structure: Me, OH, HO, COOH, Cl benzene] |
| 2 | [structure: HO-N, H₂N, OH, COOMe benzene] |
| 3 | [structure: Boc-N piperidine, Et, COOH] |
| 4 | [structure: H₂N-CH(CH₂Ph)-CONH-Ph · HCl] |
| 5 | [structure: H₂N-CH(CH₂Ph)-CONHO-Ph · HCl] |

TABLE 1-continued

| Preparative Example | |
| --- | --- |
| 6 | [structure: H₂N-CH(CH₂Ph)- oxadiazole-Me · HCl] |
| 7 | [structure: H₂N-CH(CH₂Ph)-CH₂-O-CH₂-Ph] |

PREPARATIVE EXAMPLE 1

5-Chloro-2,4-dihydroxy-3-methylbenzoic acid

To a solution of 2,4-dihydroxy-3-methylbenzoic acid methyl ester (9.9 g) in ethyl acetate (100 ml) was added tert-butyl hypochlorite (12.3 ml) under ice-cooling. After stirring for 2 hours, hexane (200 ml) was added, and the mixture was cooled with ice to allow precipitation of crystals. The crystals were collected by filtration, and dissolved in a mixed solvent of methanol (20 ml) and tetrahydrofuran (THF, 20 ml). A 1M lithium hydroxide solution (40 ml) was added to the solution, and the mixture was refluxed under heating for 18 hours. The reaction mixture was concentrated, and a 10% aqueous citric acid solution was added to the residue, which was followed by extraction with ethyl acetate. The organic layer was washed with water and saturated brine, and dried over anhydrous sodium sulfate. The organic layer was concentrated under reduced pressure to give the title compound (4.14 g, yield 37%).

PREPARATIVE EXAMPLE 2

Methyl 2-hydroxybenzoate-4-carboxamide oxime

To a solution of 2-hydroxy-4-cyanobenzoic acid methyl ester (2.00 g) in methanol (30 ml) were added water (6 ml), hydroxylamine hydrochloride (1.57 g) and sodium hydrogencarbonate (1.9 g), and the mixture was stirred with heating at 70° C. for 3 hours. The reaction mixture was concentrated, diluted with a 10% aqueous citric acid solution, and filtered. The filtrate was concentrated under reduced pressure, and the residue was purified by silica gel column chromatography (developing solvent: hexane/ethyl acetate=3/2 v/v) to give the title compound (823 mg, yield 35%).

PREPARATIVE EXAMPLE 3

1-tert-Butoxycarbonyl-4-ethylisonipecotic acid (1) 1-tert-Butoxycarbonyl-4-ethylisonipecotic acid ethyl ester To a solution of 1-tert-butoxycarbonylisonipecotic acid ethyl ester (576 mg) in THF (15 ml) was added a solution of lithium diisopropyl-amide (290 mg) in THF (10 ml) in a stream of argon gas at −78° C., and the reaction mixture was stirred at the same temperature for 1 hour. Ethyl iodide (0.36 ml) was added to the above solution at −78° C., and the mixture was stirred for 18 hours. Water was added to the reaction mixture and the mixture was extracted with ethyl acetate. The organic layer was washed successively with 1N hydrochloric acid, water and saturated brine, and dried over anhydrous magnesium sulfate. The organic layer was concentrated under reduced pressure to give the title compound (585 mg, yield 92%).

(2) 1-tert-Butoxycarbonyl-4-ethylisonipecotic acid

To a solution of 1-tert-butoxycarbonyl-4-ethylisonipecotic acid ethyl ester (570 mg) in ethanol (10 ml) was added a 1M lithium hydroxide solution (8 ml), and the mixture was refluxed under heating for 20 hours. Then, the reaction mixture was concentrated, and water was added to the residue. The aqueous layer was washed with ether, acidified with 1N hydrochloric acid, and extracted with ether. The organic layer was dried over anhydrous magnesium sulfate, and concentrated under reduced pressure to give the title compound (233 mg, yield 45%).

PREPARATIVE EXAMPLE 4

L-Phenylalanylaminobenzene hydrochloride

To a solution of N-tert-butoxycarbonyl-L-phenylalanine hydrochloride (2.65 g) and aniline (1.02 g) in dimethylformamide (DMF, 50 ml) were added 1-ethyl-3-(3-dimethylaminopropyl)carbodiimide hydrochloride (WSC.HCl) and hydroxybenzotriazole (HOBT, 1.5 g) at room temperature, and the mixture was stirred for 6 hours. Water was added to the reaction mixture and the mixture was extracted with ethyl acetate. The organic layer was washed successively with a 10% aqueous citric acid solution, water, a saturated aqueous sodium hydrogencarbonate solution, water and saturated brine, and dried over anhydrous magnesium sulfate. The solvent was distilled away under reduced pressure to give N-tert-butoxycarbonyl-L-phenylalanylamino-benzene. To a solution of the obtained compound in dichloromethane (20 ml) was added trifluoroacetic acid (10 ml) at room temperature, and the mixture was stirred for 1 hour. Toluene (10 ml) was added to the reaction mixture, and the mixture was concentrated under reduced pressure. A 1M hydrogen chloride-ether solution (10 ml) was added to the residue, and crystallization gave the title compound (1.45 g, yield 52%).

PREPARATIVE EXAMPLE 5

L-Phenylalanyl-O-benzylhydroxyamide hydrochloride

The title compound (2.48 g, yield 92% ) was obtained in the same manner as in Preparative Example 4 above, using N-tert-butoxycarbonyl-L-phenylalanine (2.65 g) and O-benzylhydroxylamine hydrochloride (1.60 g).

PREPARATIVE EXAMPLE 6

1-(3-Methyl-1,2,4-oxadiazol-5-yl)-2-phenylethylamine hydrochloride

To a solution of acetamide oxime [2.67 g, J. Saunders et al., J. Med. Chem., 33, 1128 (1990)] in THF (125 ml) was added 60% sodium hydride (1.44 g) in oil, and the mixture was refluxed under heating for 1 hour. Then, the reaction mixture was allowed to cool, and a solution of N-tert-butoxycarbonyl-L-phenylalanine methyl ester (8.38 g) in THF (40 ml) was added at room temperature. The mixture was refluxed under heating for 20 minutes. The mixture was allowed to cool, and water (10 ml) was added, which was followed by concentration under reduced pressure. A 10% aqueous citric acid solution was added to the residue, and the mixture was extracted with ethyl acetate. The organic layer was washed with saturated brine, dried over anhydrous sodium sulfate, and concentrated under reduced pressure. The residue was purified by silica gel column chromatography (developing solvent: hexane/ethyl acetate=3/1 v/v) to give 4.43 g of N-tert-butoxycarbonyl-1-(3-methyl-1,2,4-oxadiazol-5-yl)-2-phenylethylamine. This compound was added to a 4N hydrogen chloride-dioxane solution (50 ml), and the mixture was stirred at room temperature for 2 hours. Toluene was added to the reaction mixture, and the mixture was concentrated under reduced pressure. Ether was added to the residue for crystallization to give the title compound (3.25 g, yield 47%).

PREPARATIVE EXAMPLE 7

O-Benzyl-L-phenylalaninol

To a solution of L-phenylalaninol (11.78 g) in THF (200 ml) was gradually added 60% sodium hydride (3.43 g) in oil at room temperature. Twenty minutes later, the reaction mixture was refluxed under heating for 1 hour. Then, the mixture was allowed to cool, followed by gradual addition of benzyl bromide (9.27 ml) under ice-cooling, and stirred at room temperature for 16 hours. The reaction mixture was added to saturated brine, and extracted with ether. The organic layer was extracted with 10% hydrochloric acid. The aqueous layer was made alkaline with an aqueous sodium hydroxide solution, and extracted with ether. The organic layer was washed with saturated brine, dried over anhydrous magnesium sulfate, and concentrated under reduced pressure to give the title compound (14.5 g, yield 77%).

EXAMPLE 1

N-[3,5-Dichloro-2-hydroxy-4-(4-methylaminobutoxy) benzoyl]-L-phenyl-alanine methyl ester hydrochloride Step 1) 3,5-Dichloro-2-hydroxy-4-(4-tert-butoxycarbonylmethyl-aminobutoxy)benzoic acid methyl ester (VI)

To a solution of 4-tert-butoxycarbonylmethylamino-1-butanol (3 g) and known 3,5-dichloro-2,4-dihydroxybenzoic acid methyl ester (3.85 g) in THF (80 ml) were added triphenylphosphine (4.26 g) and diisopropyl azodicarboxylate (3.2 ml) under ice-cooling, and the mixture was stirred for 16 hours. The reaction mixture was concentrated under reduced pressure, and the residue was purified by silica gel column chromatography (developing solvent: hexane/ethyl acetate=4/1 v/v) to give the title compound (5.2 g, yield 83%).

Step 4) 3,5-Dichloro-2-hydroxy-4-(4-tert-butoxycarbonylmethylamino-butoxy)benzoic acid (VII)

The compound (3.46 g) obtained in the above Step 1) was dissolved in a mixed solvent of methanol (12 ml)-THF (12 ml), and a 1M lithium hydroxide solution (24 ml) was added to the mixture, which was followed by stirring with heating at 60° C. for 2 hours. After cooling with ice, the mixture was concentrated under reduced pressure. A 10% aqueous citric acid solution (50 ml) was added to the residue to acidify same, and the mixture was extracted with ether (50 ml). The organic layer was dried over anhydrous magnesium sulfate, and the solvent was distilled away under reduced pressure to give the title compound (3.22 g, yield 96%).

Step 5) N-[3,5-Dichloro-2-hydroxy-4-(4-tert-butoxycarbonylmethylamino-butoxy)benzoyl]-L-phenylalanine methyl ester (I')

To a solution of the compound (3 g) obtained in the above Step 4), L-phenylalanine methyl ester hydrochloride (1.59 g), WSC.HCl (1.41 g) and HOBT (1 g) in DMF (10 ml) was added dropwise triethylamine (1 ml) at room temperature, and the mixture was stirred for 14 hours. Water (60 ml) was added to the reaction mixture, and the mixture was extracted with ethyl acetate. The organic layer was washed successively with a 10% aqueous citric acid solution, water, a saturated aqueous sodium hydrogencarbonate solution, water and saturated brine, and dried over anhydrous sodium sulfate. Then, the solvent was distilled away under reduced pressure. The residue was purified by silica gel column chromatography (developing solvent: hexane/ethyl acetate= 3/1 v/v) to give the title compound (2.72 g, yield 65%).

Step 6) N-[3,5-Dichloro-2-hydroxy-4-(4-methylaminobutoxy)benzoyl]-L-phenylalanine methyl ester hydrochloride (I)

To a solution of the compound (5 g) obtained in the above Step 5) in dioxane (10 ml) was added a 4N hydrogen chloride-dioxane solution (40 ml), and the mixture was stirred at room temperature for 1.5 hours. The reaction mixture was diluted with toluene, and concentrated under reduced pressure. Ether (50 ml) was added to the residue for crystallization to give the title compound (4.2 g, yield 95%, see Table 2).

EXAMPLE 1'

N-[3,5-Dichloro-2-hydroxy-4-(4-methylaminobutoxy) benzoyl]-L-phenyl-alanine methyl ester hydrochloride Step 13) N-(3,5-Dichloro-2,4-dihydroxybenzoyl)-L-phenylalanine methyl ester (XVII)

To a solution of 3,5-dichloro-2,4-dihydroxybenzoic acid (17 g), L-phenylalanine methyl ester hydrochloride (19.8 g), WSC.HCl (17.6 g) and HOBT (12.4 g) in DMF (70 ml) was added dropwise triethylamine (12.8 ml) at room temperature, and the mixture was stirred for 16 hours. Then, the mixture was post-treated in the same manner as in the above Example 1, Step 5) to give the title compound (18.32 g, yield 57%).

Step 14) N-[3,5-Dichloro-2-hydroxy-4-(4-tert-butoxycarbonylmethyl-aminobutoxy)benzoyl]-L-phenylalanine methyl ester (I')

To a solution of the compound (11.0 g) obtained in the above Step 13) and 4-tert-butoxycarbonylmethylamino-1-butanol (5.29 g) in THF (100 ml) were added triphenylphosphine (7.51 g) and diisopropyl azodicarboxylate (5.6 ml) under ice-cooling, and the mixture was stirred for 16 hours. The reaction mixture was concentrated under reduced pressure, and the residue was purified by silica gel column chromatography (developing solvent: hexane/ethyl acetate= 3/1 v/v) to give the title compound (3.10 g, yield 21%).

Step 6) N-[3,5-Dichloro-2-hydroxy-4-(4-methylaminobutoxy)benzoyl]-L-phenylalanine methyl ester hydrochloride (I)

To a solution of the compound (10 g) obtained in the above Step 14) in dioxane (25 ml) was added dropwise a 4N hydrogen chloride-dioxane solution (88 ml) at room temperature. After 1.5 hours, toluene was added. The solvent was distilled away under reduced pressure, and ether (120 ml) was added to the residue for crystallization to give the title compound (8.4 g, yield 95%).

EXAMPLE 2

N-{3,5-Dichloro-2-hydroxy-4-[2-(4-methylpiperazin-1-yl)ethoxy]-benzoyl}-L-phenylalanine ethyl ester dihydrochloride Step 1) 3,5-Dichloro-2-hydroxy-4-[2-(4-methylpiperazin-1-yl)-ethoxy]benzoic acid methyl ester (VI)

To a solution of 2-(4-methylpiperazin-1-yl)ethanol (14.42 g) and 3,5-dichloro-2,4-dihydroxybenzoic acid methyl ester (52.15 g) in chloroform (400 ml) were added triphenylphosphine (28.85 g) and azodicarboxylic acid diisopropyl (21.7 ml) at room temperature, and the mixture was stirred for 16 hours. 1N Hydrochloric acid (300 ml) was added to the reaction mixture for extraction to give a crude product of the title compound. Step 4) 3,5-Dichloro-2-hydroxy-4-[2-(4-methylpiperazin-1-yl)ethoxy]-benzoic acid (VII)

To the extract of the crude product obtained in the above Step 1) was added a 4M aqueous sodium hydroxide solution (125 ml), and the mixture was stirred under heating at 80° C. for 2 hours. Acetic acid (12.3 g) was further added to the mixture. The mixture was stirred under ice-cooling, and applied to crystallization to give the title compound (27.880 g, yield 79%).

Step 5) N-{3,5-Dichloro-2-hydroxy-4-[2-(4-methylpiperazin-1-yl)ethoxy]-benzoyl}-L-phenylalanine ethyl ester dihydrochloride (I'=I)

To a solution of the compound (958 mg) obtained in the above Step 4), L-phenylalanine ethyl ester hydrochloride (923 mg) and HOBT (445 mg) in acetonitrile (15 ml) was added WSC.HCl (632 mg) at room temperature, and the mixture was stirred for 25 hours. The reaction mixture was concentrated under reduced pressure, and chloroform was added to the residue. The mixture was washed successively with a saturated aqueous sodium hydrogencarbonate solution, water and saturated brine, dried over anhydrous sodium sulfate, and concentrated under reduced pressure. The residue was purified by silica gel column chromatography (developing solvent: chloroform/methanol=10/1 v/v) to give a compound (1.386 g). Then, a 4N hydrogen chloride-ethyl acetate solution was added to a solution of the compound (1.003 g) in acetone (10 ml) for crystallization to give the title compound (1.073 g, yield 93%, see Table 2).

EXAMPLES 3–87

The compounds of Examples 3–87 were prepared in the same manner as in Example 1, Example 1' and Example 2 from the corresponding compounds (see Tables 3–45).

EXAMPLE 88

N-[2-Hydroxy-4-(4-methylaminobutyl)benzoyl]-L-phenylalanine methyl ester hydrochloride Step 3) 4-[4-(tert-Butoxycarbonylmethylamino)butyl]-2-hydroxybenzoic acid methyl ester (VI)

(1) 4-[4-(tert-Butoxycarbonylmethylamino)-1-butenyl]-2-hydroxybenzoic acid methyl ester To a solution of [(3-hydroxy-4-methoxycarbonyl)benzyl] triphenyl-phosphonium bromide (2.537 g), obtained by a known method, in THF (25 ml) was added dropwise a 2M lithium diisopropylamide-THF solution (5.5 ml) in a stream of argon at 0° C., and the mixture was stirred for 30 minutes. Then, a solution of 4-(tert-butoxycarbonylmethylamino) butylaldehyde (1.123 g), prepared by a known method, in THF (10 ml) was gradually added dropwise at 0° C., and the mixture was stirred at room temperature for 4 hours. A saturated aqueous ammonium chloride solution (1 ml) was gradually added, and the mixture was concentrated under reduced pressure, which was followed by extraction with toluene. The extract was washed with a 10% aqueous citric acid solution and saturated brine, dried over anhydrous sodium sulfate, and concentrated under reduced pressure. The residue was purified by silica gel column chromatography (developing solvent: hexane/ethyl acetate=4/1 v/v) to give the title compound (0.850 g, yield 51%).

(2) 4-[4-(tert-Butoxycarbonylmethylamino)butyl]-2-hydroxybenzoic acid methyl ester A solution of the compound (0.845 g) obtained in (1) above in methanol (20 ml) was vigorously stirred in the presence of 10% palladium-carbon (0.106 g) in a stream of hydrogen. After filtering through Celite, the mixture was concentrated under reduced pressure, and the residue was purified by silica gel column chromatography (developing solvent: hexane/ethyl acetate=4/1 v/v) to give the title compound (0.810 g, yield 95%).

Step 4) 4-[5-(tert-Butoxycarbonylmethylamino)butyl]-2-hydroxybenzoic acid (VII)

The compound (0.806 g) obtained in the above Step 3) was subjected to the same reaction as in the above Example 1, Step 4) to give the title compound (0.760 g, yield 98%).

Step 5) N-[2-Hydroxy-4-(4-tert-butoxycarbonylmethylaminobutyl)benzoyl]-L-phenylalanine methyl ester (I')

The compound (0.753 g) obtained in the above Step 4) and L-phenylalanine methyl ester hydrochloride (0.552 g) was subjected to the same reaction as in the above Example 1, Step 5) to give the title compound (0.714 g, yield 63%).

Step 6) N-[2-Hydroxy-4-(4-methylaminobutyl)benzoyl]-L-phenylalanine methyl ester hydrochloride (I)

The compound (0.128 g) obtained in the above Step 5) was subjected to the same reaction as in the above Example 1, Step 6) to give the title compound (0.087 g, yield 78%, see Table 46).

EXAMPLES 89, 90

The compounds of Examples 89 and 90 were prepared in the same manner as in Example 88 from the corresponding compounds (see Tables 46–47).

EXAMPLE 91

N-[3,5-Dichloro-2-hydroxy-4-(5-methylaminopentyl)benzoyl]-L-phenyl-alanine methyl ester hydrochloride Step 11) 4-[5-(tert-Butoxycarbonylmethylamino)pentyl]-3,5-dichloro-2-hydroxybenzoic acid methyl ester (VI)

To a solution of 4-[5-(tert-butoxycarbonylmethylamino)pentyl]-2-hydroxybenzoic acid methyl ester (3.95 g), obtained in the same manner as in the above Example 88, Step 3), in acetonitrile (35 ml) was added sulfuryl chloride (9 ml) at room temperature, and the mixture was refluxed under heating at 60° C. for 1 hour. Toluene was added to the reaction mixture and the mixture was concentrated under reduced pressure. Dichloromethane (85 ml) was added to the residue. Then, triethylamine (7.85 ml) and di-tert-butyl dicarbonate (4.9 g) were added, and the mixture was stirred at room temperature for 1 hour. Water (50 ml) was added to the reaction mixture for washing, and the mixture was dried over anhydrous sodium sulfate, and concentrated under reduced pressure. The residue was purified by silica gel column chromatography (developing solvent:hexane/ethyl acetate=4/1 v/v) to give the title compound (2.319 g, yield 50%).

Step 4) 4-[5-(tert-Butoxycarbonylmethylamino)pentyl]-3,5-dichloro-2-hydroxybenzoic acid (VII)

The compound (2.319 g) obtained in the above Step 11) was subjected to the same reaction as in the above Example 1, Step 4) to give the title compound (1.994 g, yield 89%).

Step 5) N-[4-(5-tert-Butoxycarbonylmethylaminopentyl)-3,5-dichloro-2-hydroxybenzoyl]-L-phenylalanine methyl ester (I')

The compound (2.874 g) obtained in the above Step 4) and L-phenylalanine methyl ester hydrochloride (1.522 g) was subjected to the same reaction as in the above Example 1, Step 5) to give the title compound (3.441 g, yield 86%).

Step 6) N-[3,5-Dichloro-2-hydroxy-4-(5-methylaminopentyl)benzoyl]-L-phenylalanine methyl ester hydrochloride (I)

The compound (3.426 g) obtained in the above Step 5) was subjected to the same reaction as in the above Example 1, Step 6) to give the title compound (2.525 g, yield 83%, see Table 48).

EXAMPLES 92–104

The compounds of Examples 92–104 were prepared in the same manner as in Example 91 from the corresponding compounds (see Tables 48–54).

EXAMPLE 105

N-[2-Benzoyloxy-3,5-dichloro-4-(4-methylaminobutoxy)benzoyl]-L-phenylalanine methyl ester hydrochloride Step 12) N-[2-Benzoyloxy-3,5-dichloro-4-(4-tert-butoxycarbonylmethyl-aminobutoxy)benzoyl]-L-phenylalanine methyl ester (I')

To a solution of the compound (212 mg), obtained in the above Example 1, Step 5), in dichloromethane (3 ml) were added pyridine (60 μl) and benzoyl chloride (80 μl) at room temperature, and the mixture was stirred for 30 minutes. Water (5 ml) was added to the reaction mixture and the mixture was extracted with ethyl acetate. The organic layer was washed successively with a 10% aqueous citric acid solution, a saturated aqueous sodium hydrogencarbonate solution, water and saturated brine, and dried over anhydrous magnesium sulfate. Then, the solvent was distilled away under reduced pressure. The residue was purified by silica gel column chromatography (developing solvent: hexane/ethyl acetate—3/1 v/v) to give the title compound (224 mg, yield 95%).

Step 6) N-[2-Benzoyloxy-3,5-dichloro-4-(4-methylaminobutoxy)benzoyl]-L-phenylalanine methyl ester hydrochloride (I)

The compound (224 mg) obtained in the above Step 12) was subjected to the same reaction as in the above Example 1, Step 6) to give the title compound (159 mg, yield 83%, see Table 55).

EXAMPLES 106–125

The compounds of Examples 106–125 were prepared in the same manner as in Example 105 from the corresponding compounds (see Tables 55–65).

EXAMPLE 126

N-[3,5-Dichloro-2-hydroxy-4-(4-methylaminobutoxy)benzoyl]-L-phenylalanine hydrochloride Step 6) N-[3,5-Dichloro-2-hydroxy-4-(4-methylaminobutoxy)benzoyl]-L-phenylalanine hydrochloride (I)

To a solution of N-[3,5-dichloro-2-hydroxy-4-(4-tert-butoxy-carbonylmethylaminobutoxy)benzoyl]-L-phenylalanine tert-butyl ester (490 mg), obtained in the same manner as in the above Example 1, Step 5), in dichloromethane (8 ml) was added trifluoroacetic acid (4 ml) at room temperature, and the mixture was stirred for 14 hours. Toluene was added to the reaction mixture and the mixture was concentrated under reduced pressure. A 1M hydrogen chloride-ether solution (5 ml) was added to the residue for crystallization to give the title compound (250 mg, yield 67%, see Table 66).

EXAMPLES 127–135

The compounds of Examples 127–135 were prepared in the same manner as in Example 126 from the corresponding compounds (see Tables 66–70).

EXAMPLE 136

N-[3,5-Dichloro-2-hydroxy-4-(4-methylaminobutylamino)benzoyl]-L-phenylalanine methyl ester dihydrochloride Step 16) N-[2-Hydroxy-4-(4-tert-butoxycarbonylmethylaminobutylamino)-benzoyl]-L-phenylalanine methyl ester (I')

A solution of N-[(4-amino-2-hydroxy)benzoyl]-L-phenylalanine methyl ester (1.11 g) obtained in the same manner as in the above Example 1', Step 13) and 4-(tert-butoxycarbonylmethylamino)-1-butylaldehyde (711 mg) in methanol (20 ml) was stirred at room temperature in a stream of argon for 4 hours. 10% Palladium-carbon (200 mg) was added to the reaction mixture, and the mixture was subjected to catalytic hydrogenation using hydrogen gas under atmospheric pressure. Four hours later, the reaction mixture was filtered, and the filtrate was concentrated under reduced pressure. The residue was purified by silica gel column chromatography (developing solvent: hexane/ethyl acetate=3/2 v/v) to give the title compound (900 mg, yield 51%).

Step 11) N-[3,5-Dichloro-2-hydroxy-4-(4-tert-butoxycarbonylmethyl-aminobutylamino)benzoyl]-L-phenylalanine methyl ester (I')

To a solution of the compound (900 mg) obtained in the above Step 16) in dichloromethane (20 ml) was added dropwise tert-butyl hypochlorite (0.46 ml) under ice-cooling, and the mixture was stirred under ice-cooling for 50 minutes. The reaction mixture was washed with water and saturated brine, and dried over anhydrous sodium sulfate. The solvent was distilled away under reduced pressure, and the residue was purified by silica gel column chromatography (developing solvent: hexane/ethyl acetate=3/1 v/v) to give the title compound (830 mg, yield 82%).

Step 6) N-[3,5-Dichloro-2-hydroxy-4-(4-methylaminobutylamino)benzoyl]-L-phenylalanine methyl ester dihydrochloride (I)

To a solution of the compound (280 mg) obtained in the above Step 11) in chloroform (5 ml) was added trifluoroacetic acid (2.5 ml) at room temperature, and the mixture was stirred for 20 minutes. Toluene was added to the reaction mixture and the mixture was concentrated under reduced pressure. A 1M hydrogen chloride-ether solution was added to the residue for crystallization to give the title compound (218 mg, yield 82%, see Table 71).

EXAMPLE 137

The compound of Example 137 was prepared in the same manner as in Example 136 from the corresponding compound (see Table 71). EXAMPLE 138

N-[3,5-Dichloro-2-hydroxy-4-(4-aminobutoxy)benzoyl]-L-phenyl-alanylaminobenzene hydrochloride 3,5-Dichloro-2-hydroxy-4-(4-tert-butoxycarbonylaminobutoxy)-benzoic acid (347 mg) obtained in the same manner as in the above Example 1, Step 4) and L-phenylalanylaminobenzene hydrochloride (268 mg) were subjected to the same reaction as in the above Example 1, Step 5) and Step 6) to give the title compound (284 mg, yield 58%, see Table 72).

EXAMPLES 139–142

The compounds of Examples 139–142 were prepared in the same manner as in Example 138 from the corresponding compounds (see Tables 72–74).

EXAMPLE 143

N-[3,5-Dichloro-2-hydroxy-4-(4-methylaminobutoxy)benzoyl]-L-phenylalanylhydroxyamide
Step 5) N-[3,5-Dichloro-2-hydroxy-4-(4-benzyloxycarbonylmethylamino-butoxy)benzoyl]-L-phenylalanyl-0-benzylhydroxyamide (I')

3,5-Dichloro-2-hydroxy-4-(4-benzyloxycarbonylaminobutoxy)benzoic acid (237 mg) obtained in the same manner as in the above Example 1, Step 4) and L-phenylalanyl-O-benzylhydroxyamide hydrochloride (203 mg) were subjected to the same reaction as in the above Example 1, Step 5) to give the title compound (325 mg, yield 59%).
Step 6) N-[3,5-Dichloro-2-hydroxy-4-(4-methylaminobutoxy)benzoyl]-L-phenylalanylhydroxyamide (I)

To a solution of the compound (210 mg) obtained in the above Step 5) in methanol (5 ml) was added palladium hydroxide (42 mg), and the mixture was subjected to catalytic hydrogenation using hydrogen gas under atmospheric pressure. Twelve hours later, the reaction mixture was filtered, and the filtrate was concentrated under reduced pressure. Methanol-ether was added to the residue for crystallization to give the title compound (188 mg, yield 62%, see Table 74).

EXAMPLE 144

N-[4-(4-Aminobutoxy)-3,5-dichloro-2-hydroxybenzoyl]-1-(3-methyl-1,2,4-oxadiazol-5-yl)-2-phenylethylamine hydrochloride 3,5-Dichloro-2-hydroxy-4-(4-tert-butoxycarbonylaminobutoxy)-benzoic acid (394 mg) obtained in the same manner as in the above Example 1, Step 4) and 1-(3-methyl-1,2,4-oxadiazol-5-yl)-2-phenylethylamine hydrochloride (240 mg) were subjected to the same reaction as in the above Example 1, Step 5) and Step 6) to give the title compound (299 mg, yield 58%, see Table 75).

EXAMPLE 145

N-[4-(4-Aminobutoxy)-3,5-dichloro-2-hydroxybenzoyl]-L-phenyl-alaninol hydrochloride 3,5-Dichloro-2-hydroxy-4-(4-tert-butoxycarbonylaminobutoxy)-benzoic acid (394 mg) obtained in the same manner as in the above Example 1, Step 4) and O-benzyl-L-phenylalaninol (242 mg) were subjected to the same reaction as in the above Example 1, Step 5), Example 99, Step 6) and Example 1, Step 6) to give the title compound (190 mg, yield 42%, see Table 75).

EXAMPLE 146

(2S)-3-Phenyl-2-[5-(4-aminobutoxy)-3-hydroxy-2-naphthoylamino]-propionic acid methyl ester hydrochloride
Step 13) (2S)-3-Phenyl-2-(3,5-dihydroxy-2-naphthoylamino)propionic acid methyl ester (XVII)

A solution of 3,5-dihydroxy-2-naphthoic acid (4.08 g), L-phenylalanine methyl ester hydrochloride (4.74 g), WSC.HCl (4.22 g), HOBT (2.97 g) and N-methylmorpholine (2.41 ml) in DMF (200 ml) was stirred at room temperature for 16 hours. Water was added to the reaction mixture, and the mixture was extracted with ethyl acetate. The organic layer was washed successively with a 10% aqueous citric acid solution, water, a saturated aqueous sodium hydrogencarbonate solution, water and saturated brine, dried over anhydrous sodium sulfate, and concentrated under reduced pressure. The residue was purified by silica gel column chromatography (developing solvent: hexane/ethyl acetate=1/1 v/v) to give the title compound (4.42 g, yield 61%).
Step 14) (2S)-3-Phenyl-2-[5-(4-tert-butoxycarbonylaminobutoxy)-3-hydroxy-2-naphthoylamino]propionic acid methyl ester (I')

To a solution of the compound (1.83 g) obtained in the above Step 13), triphenylphosphine (1.31 g) and 4-tert-butoxycarbonylaminobutyl alcohol (473 mg) in THF (25 ml) was added dropwise diisopropyl azodicarboxylate (0.98 ml) at room temperature. After stirring at room temperature for 16 hours, the reaction mixture was concentrated under reduced pressure, and the residue was purified by silica gel column chromatography (developing solvent: hexane/ethyl acetate=2/1 v/v) to give the title compound (375 mg, yield 30%).

Step 6) (2S)-3-Phenyl-2-[5-(4-aminobutoxy)-3-hydroxy-2-naphthoylamino]-propionic acid methyl ester hydrochloride (I)

To a solution of the compound (375 mg) obtained in the above Step 14) in THF (5 ml) was added a 4N hydrogen chloride-dioxane solution (5 ml), and the mixture was stirred at room temperature for 3 hours. The mixture was concentrated under reduced pressure. Ether was added to the residue for crystallization to give-the title compound (187 mg, yield 57%, see Table 76).

EXAMPLE 147

N-[4-[4-(4-Methylaminobutoxy)phenyl]benzoyl]-L-phenylalanine ethyl ester hydrochloride Step 13) 4-(4-Hydroxyphenyl)benzoyl-L-phenylalanine ethyl ester (XVII)

To a solution of 4-(4-hydroxyphenyl)benzoic acid (3.0 g) and L-phenylalanine ethyl ester hydrochloride (3.38 g) in DMF (30 ml) were added WSC.HCl (2.7 g), HOBT (1.89 g) and triethylamine (2 ml), and the mixture was stirred at room temperature for 14 hours. Water was added to the reaction mixture and the mixture was extracted with ethyl acetate. The organic layer was washed successively with a 10% aqueous citric acid solution, water, a saturated aqueous sodium hydrogen-carbonate solution, water and saturated brine, dried over anhydrous sodium sulfate, and concentrated under reduced pressure to give a crude product of the title compound.

Step 15) N-[4-[4-(4-tert-Butoxycarbonylmethylaminobutoxy)phenyl]-benzoyl]-L-phenylalanine ethyl ester (I')

To a solution of the crude product obtained in the above Step 13) in DMF (30 ml) were added 4-(tert-butoxycarbonylmethylamino)butyl bromide (4.46 g) and potassium carbonate (4.65 g), and the mixture was stirred at room temperature for 14 hours. Ethyl acetate was added to the reaction mixture. The mixture was washed successively with water, a 10% aqueous citric acid solution and saturated brine, and dried over anhydrous sodium sulfate. The organic layer was concentrated under reduced pressure, and the residue was purified by silica gel column chromatography (developing solvent: hexane/ethyl acetate=3/1 v/v) to give the title compound (967 mg, yield 10%).

Step 6) N-[4-[4-(4-Methylaminobutoxy)phenyl]benzoyl]-L-phenylalanine ethyl ester hydrochloride (I)

To a solution of the compound (140 mg) obtained in the above Step 14) in THF (2 ml) was added a 4N hydrogen chloride-dioxane solution (2 ml). The mixture was stirred at room temperature for 4 hours, and concentrated under reduced pressure. Ether was added to the residue for crystallization to give the title compound (71 mg, yield 58%, see Table 76).

EXAMPLE 148

(2S)-3-Phenyl-2-[4-[5-(4-methylaminobutyl)-1,2,4-oxadiazol-3-yl]-2-hydroxybenzoylamino]propionic acid ethyl ester hydrochloride Step 9) Methyl 2-hydroxybenzoate-4-carboxamide O-(4-tert-butoxycarbonyl-methylaminovaleryl) oxime (XV)

A solution of 4-tert-butoxycarbonylmethylaminovaleric acid (255 mg), methyl 2-hydroxybenzoate-4-carboxamide oxime (210 mg), WSC.HCl (211 mg) and 4-dimethylaminopyridine (DMAP, 135 mg) in dichloromethane (5 ml) was stirred at room temperature for 16 hours. Water was added to the reaction mixture and the mixture was extracted with ethyl acetate. The organic layer was washed successively with a 10% aqueous citric acid solution, water, a saturated aqueous sodium hydrogencarbonate solution, water and saturated brine, dried over anhydrous sodium sulfate, and concentrated under reduced pressure. The residue was purified by silica gel column chromatography (developing solvent: hexane/ethyl acetate= 1/1 v/v) to give the title compound (229 mg, yield 54%).

Step 10) 2-Hydroxy-4-[5-(4-tert-butoxycarbonylmethylaminobutyl)-1,2,4-oxadiazol-3-yl] benzoic acid methyl ester (VI')

A solution of the compound (224 mg) obtained in the above Step 9) in toluene (20 ml) was refluxed under heating for 16 hours. The reaction mixture was allowed to cool, and concentrated under reduced pressure. The residue was purified by silica gel column chromatography (developing solvent: hexane/ethyl acetate=3/1 v/v) to give the title compound (148 mg, yield 69%).

Step 4) 2-Hydroxy-4-[5-(4-tert-butoxycarbonylmethylaminobutyl)-1,2,4-oxadiazol-3-yl] benzoic acid (VII)

To a solution of the compound (146 mg) obtained in the above Step 10) in ethanol (10 ml) was added a 1M lithium hydroxide solution (5 ml), and the mixture was refluxed under heating for 2 hours. The reaction mixture was concentrated under reduced pressure, and a 10% aqueous citric acid solution was added to the residue, which was followed by extraction with ethyl acetate. The organic layer was washed with water, and dried over anhydrous sodium sulfate. The organic layer was concentrated under reduced pressure to give the title compound (140 mg, yield 99%).

Step 5) (2S)-3-Phenyl-2-[4-[5-(4-tert-butoxycarbonylmethylaminobutyl)-1,2,4-oxadiazol-3-yl]-2-hydroxybenzoylamino]propionic acid ethyl ester (I')

A solution of the compound (140 mg) obtained in the above Step 4), L-phenylalanine ethyl ester hydrochloride (92 mg), WSC.HCl (77 mg), HOBT (54 mg) and triethylamine (0.056 ml) in DMF (1.5 ml) was stirred at room temperature for 15 hours. Water was added to the reaction mixture and the mixture was extracted with ethyl acetate. The organic layer was washed successively with a 10% aqueous citric acid solution, water, a saturated aqueous sodium hydrogencarbonate solution, water and saturated brine, dried over anhydrous sodium sulfate, and concentrated under reduced pressure. The residue was purified by silica gel column chromatography (developing solvent: hexane/ethyl acetate=2/1 v/v) to give the title compound (174 mg, yield 85%).

Step 6) (2S)-3-Phenyl-2-[4-[5-(4-methylaminobutyl)-1,2,4-oxadiazol-3-yl]-2-hydroxybenzoylamino]propionic acid ethyl ester hydrochloride (I)

To a solution of the compound (172 mg) obtained in the above Step 5) in THF (2 ml) was added a 4N hydrogen chloride-dioxane solution (2 ml), and the mixture was stirred at room temperature for 3 hours. The reaction mixture was concentrated under reduced pressure, and ether was added to the residue for crystallization to give the title compound (133 mg, yield 87%, see Table 77).

EXAMPLES 149–151

The compounds of Examples 149–151 were prepared in the same manner as in Example 148 from the corresponding compounds (see Tables 77–78).

EXAMPLE 152

(2S)-2-[2-(3-Methylaminopropylsulfanyl)benzoxazole-5-carbonyl-amino]-3-phenylpropionic acid ethyl ester hydrochloride Step 2) 2-(3-tert-Butoxycarbonylmethylaminopropylsulfanyl)-5-ethoxycarbonylbenzoxazole (VI)

To a solution of 5-ethoxycarbonyl-2-mercaptobenzoxazole (670 mg) in DMF was added 60% sodium hydride (126 mg) in oil under ice-cooling, and the mixture was stirred for 30 minutes. A solution of 3-tert-butoxycarbonylmethylaminopropyl chloride (623 mg) in DMF was added to the reaction mixture, and the mixture was stirred with heating at 60° C. for 18 hours. Ethyl acetate was added to the reaction mixture, and the organic layer was washed with water and dried over anhydrous sodium sulfate. The organic layer was concentrated under reduced pressure, and the residue was purified by silica gel column chromatography (developing solvent: hexane/ethyl acetate=4/1 v/v) to give the title compound (594 mg, yield 50%).

Step 4) 2-(3-tert-Butoxycarbonylmethylaminopropylsulfanyl)-5-carboxybenzoxazole (VII)

To a mixed solution of the compound (562 mg) obtained in the above Step 2) in ethanol (2 ml)-THF (2 ml) was added a 1M lithium hydroxide solution, and the mixture was stirred with heating at 60° C. for 1 hour. The reaction mixture was concentrated under reduced pressure, and ethyl acetate and a 10% aqueous citric acid solution were added. The organic layer was dried over anhydrous sodium sulfate, and concentrated under reduced pressure to give the title compound (465 mg, yield 98%).

Step 5) (2S)-2-[2-(3-tert-Butoxycarbonylmethylaminopropylsulfanyl)-benzoxazole-5-carbonylamino]-3-phenylpropionic acid ethyl ester (I')

A solution of the compound (465 mg) obtained in the above Step 4), L-phenylalanine ethyl ester hydrochloride (302 mg), WSC.HCl (250 mg), HOBT (176 mg) and triethylamine (0.18 ml) in DMF was stirred at room temperature for 14 hours. Water was added to the reaction mixture and the mixture was extracted with ethyl acetate. The organic layer was washed successively with a 10% aqueous citric acid solution, water, a saturated aqueous sodium hydrogencarbonate solution, water and saturated brine, dried over anhydrous sodium sulfate, and concentrated under reduced pressure. The residue was purified by silica gel column chromatography (developing solvent: hexane/ethyl acetate=4/1 v/v) to give the title compound (240 mg, yield 40%).

Step 6) (2S)-2-[2-(3-Methylaminopropylsulfanyl) benzoxazole-5-carbonyl-amino]-3-phenylpropionic acid ethyl ester hydrochloride (I)

To a solution of the compound (231 mg) obtained in the above Step 5) in THF (5 ml) was added a 4N hydrogen chloride-dioxane solution (5 ml), and the mixture was stirred at room temperature for 4 hours. The reaction mixture was concentrated under reduced pressure, and ether was added for crystallization to give the title compound (136 mg, yield 67%, see Table 79).

EXAMPLES 153–154

The compounds of Examples 153–154 were prepared in the same manner as in Example 152 from the corresponding compounds (see Tables 79–80).

EXAMPLE 155

N-[3,5-Dichloro-2-hydroxy-4-(3-piperazinylpropionyloxy)benzoyl]-L-phenylalanine ethyl ester dihydrochloride Step 18) N-[3,5-Dichloro-2-hydroxy-4-[3-(4-tert-butoxycarbonyl-piperazinyl)propionyloxy]benzoyl]-L-phenylalanine ethyl ester (I')

To a solution of N-(3,5-dichloro-2,4-dihydroxybenzoyl)-L-phenyl-alanine ethyl ester (398 mg) obtained in the same manner as in the above Example 1', Step 13), 3-(4-tert-butoxycarbonylpiperazinyl)propionic acid (258 mg) and 4-dimethylaminopyridine (147 mg) in DMF (4 ml) was added WSC.HCl (230 mg) under ice-cooling, and the mixture was stirred at room temperature for 2 hours. Ethyl acetate (40 ml) was added to the reaction mixture, and the mixture was washed successively with water, a saturated aqueous sodium hydrogencarbonate solution, water and saturated brine. The reaction mixture was dried over anhydrous sodium sulfate, and the solvent was distilled away under reduced pressure. The residue was purified by silica gel column chromatography (developing solvent: ethyl acetate/hexane=1/1 v/v) to give the title compound (258 mg, yield 40%).

Step 6) N-[3,5-Dichloro-2-hydroxy-4-(3-piperazinylpropionyloxy)benzoyl]-L-phenylalanine ethyl ester dihydrochloride (I)

To a solution of the compound (258 mg) obtained in the above Step 18) in dichloromethane (2 ml) was added trifluoroacetic acid (2 ml), and the mixture was stirred at room temperature for 10 minutes. The solvent was distilled away under reduced pressure, and 1M hydrogen chloride-ether (3 ml) was added for crystallization to give the title compound (173 mg, yield 70%, see Table 81).

EXAMPLES 156–158

The compounds of Examples 156–158 were prepared in the same manner as in Example 155 from the corresponding compounds (see Tables 81–82).

The structures and physical properties of the compounds of the above Examples are shown in the following Tables 2–82.

In the Tables, Me, Et, Ph, Bn and Ac mean methyl, ethyl, phenyl, benzyl and acetyl, respectively.

TABLE 2

| Ex. No. | Compound | $^1$H-NMR δ (ppm), 300 MHz | IR (cm$^{-1}$) | FAB-MS | Elemental analysis (%) |
|---|---|---|---|---|---|
| 1 | 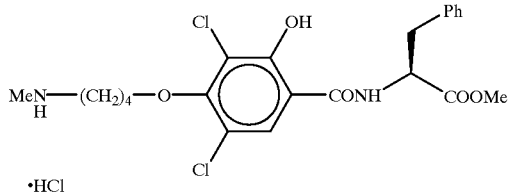 | DMSO-d$_6$<br>1.82(4H, bs)<br>2.56(3H, t, J=5.4Hz)<br>2.96(2H, bs)<br>3.04–3.28(2H, m)<br>3.66(3H, s)<br>4.05(2H, bs)<br>4.72–4.82(1H, m)<br>8.17(1H, s)<br>8.48(2H, bs)<br>9.44(1H, bs)<br>13.35(1H, s) | KBr<br>3422<br>2953<br>1742<br>1637<br>1458<br>1219 | 469<br>(free base, MH$^+$) | C$_{22}$H$_{26}$Cl$_2$N$_2$O$_5$·HCl<br>Calculated<br>C, 52.24<br>H, 5.38<br>N, 5.53<br>Found<br>C, 52.05<br>H, 5.37<br>N, 5.51 |
| 2 | 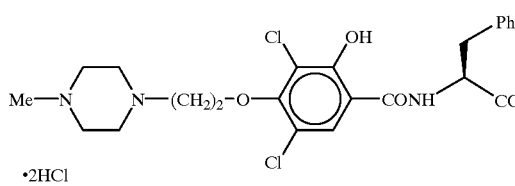 | DMSO-d$_6$<br>1.14(3H, t, J=6.0Hz)<br>2.81(3H, s)<br>3.0–3.60(10H, m)<br>4.11(2H, q, J=6.0Hz)<br>4.34(2H, brs)<br>4.68–4.78(1H, m)<br>7.19–7.29(5H, m)<br>8.22(1H, s)<br>9.46(1H, d, J=7.0Hz)<br>13.40(1H, brs) | KBr<br>3406<br>2957<br>2372<br>1736<br>1642<br>1458 | 524<br>(free base, MH$^+$) | C$_{25}$H$_{31}$Cl$_2$N$_2$O$_5$·2HCl<br>Calculated<br>C, 50.27<br>H, 5.57<br>N, 7.03<br>Found<br>C, 50.19<br>H, 5.74<br>N, 6.93 |

TABLE 3

| Ex. No. | Compound | $^1$H-NMR δ (ppm), 300 MHz | IR (cm$^{-1}$) | FAB-MS | Elemental analysis (%) |
|---|---|---|---|---|---|
| 3 | 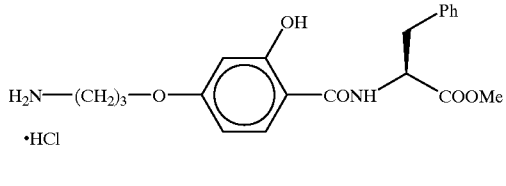 | DMSO-d$_6$<br>1.86–2.04(2H, m)<br>2.82–2.92(2H, m)<br>3.02–3.18(2H, m)<br>3.64(3H, s)<br>4.06–4.17(2H, m)<br>4.72–4.84(1H, m)<br>6.42–6.52(2H, m)<br>7.16–7.34(5H, m)<br>7.65(1H, d, J=8.5Hz)<br>7.96(3H, brs)<br>8.21(1H, d, J=7.4Hz)<br>10.24(1H, s) | KBr<br>3383<br>1739<br>1632<br>1607<br>1534<br>1498 | 372<br>(free base, MH$^+$) | |
| 4 | 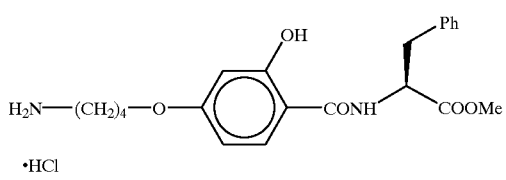 | DMSO-d$_6$<br>1.46–1.73(4H, m)<br>2.63–2.86(2H, m)<br>3.00–3.18(2H, m)<br>3.64(3H, s)<br>3.92–4.11(2H, m)<br>4.78–4.89(1H, m)<br>6.43–6.53(2H, m)<br>7.10–7.34(5H, m)<br>7.75(1H, d, J=8.5Hz)<br>7.82–8.04(3H, brs)<br>8.22(1H, d, J=7.0Hz)<br>10.24(1H, s) | KBr<br>3378<br>1630<br>1604<br>1534<br>1498 | 386<br>(free base, MH$^+$) | |

TABLE 4

| Ex. No. | Compound | $^1$H-NMR δ (ppm), 300 MHz | IR (cm$^{-1}$) | FAB-MS | Elemental analysis (%) |
|---|---|---|---|---|---|
| 5 | H$_2$N—(CH$_2$)$_5$—O—[2-OH, CONH-CH(CH$_2$Ph)-COOMe benzene]·HCl | DMSO-d$_6$<br>1.18–1.42(2H, m)<br>1.43–1.54(4H, m)<br>2.62–2.78(2H, m)<br>3.02–3.21(2H, m)<br>3.67(3H, s)<br>3.91–4.08(2H, m)<br>4.82–4.94(1H, m)<br>6.42–6.52(2H, m)<br>7.20–7.36(3H, m)<br>7.78(1H, d, J=8.4Hz)<br>7.80–7.94(3H, brs)<br>8.24(1H, d, J=7.3Hz)<br>10.25(1H, s) | KBR<br>1630<br>1604<br>1534<br>1498<br>1201 | 400 (free base, MH$^+$) | |
| 6 | H$_2$N—(CH$_2$)$_6$—O—[2-OH, CONH-CH(CH$_2$Ph)-COOMe benzene]·HCl | DMSO-d$_6$<br>1.14–1.34(4H, m)<br>1.40–1.61(4H, m)<br>2.66–2.80(2H, m)<br>3.01–3.16(2H, m)<br>3.92–4.04(2H, m)<br>4.80–4.90(1H, m)<br>6.44(1H, d, J=2.2Hz)<br>6.48(1H, dd, J=8.4, 2.2Hz)<br>7.10–7.32(5H, m)<br>7.77(1H, d, J=8.4Hz)<br>7.85(3H, brs)<br>8.24(1H, d, J=7.4Hz)<br>10.22(1H, brs) | KBr<br>3378<br>1630<br>1605<br>1534<br>1498<br>1181 | 414 (free base, MH$^+$) | |

TABLE 5

| Ex. No. | Compound | $^1$H-NMR δ (ppm), 300 MHz | IR (cm$^{-1}$) | FAB-MS | Elemental analysis(%) |
|---|---|---|---|---|---|
| 7 | MeNH—(CH$_2$)$_4$—O—[Cl, OH, CONH-CH(CH$_2$Ph)-COOMe benzene]·HCl | DMSO-d$_6$<br>1.71–1.88(4H, m)<br>2.48–2.57(3H, m)<br>2.90–3.01(2H, m)<br>3.10–3.25(2H, m)<br>3.66(3H, s)<br>4.16(2H, t, J=6Hz)<br>4.69–4.76(1H, m)<br>6.78(1H, d, J=9Hz)<br>7.16–7.32(5H, m)<br>7.94(1H, d, J=9Hz)<br>8.70(2H, brs)<br>9.26(1H, d, J=9Hz)<br>13.35(1H, s) | Neat<br>2954<br>1728<br>1642<br>1589<br>1548<br>1497 | 435 (free base, MH$^+$) | |
| 8 | MeNH—(CH$_2$)$_4$—O—[Cl, OH, CONH-CH(CH$_2$Ph)-COOEt benzene]·HCl | DMSO-d$_6$<br>1.14(3H, t, J=6Hz)<br>1.72–1.88(4H, m)<br>2.49–2.55(3H, m)<br>2.90–3.02(2H, m)<br>3.10–3.24(2H, m)<br>4.11(2H, q, J=6Hz)<br>4.17(2H, t, J=6Hz)<br>4.65–4.73(1H, m)<br>6.79(1H, d, J=9Hz)<br>7.17–7.32(5H, m)<br>7.95(1H, d, J=9Hz)<br>8.09(2H, brs)<br>9.23(1H, d, J=6Hz)<br>13.37(1H, s) | Neat<br>2958<br>1773<br>1641<br>1588<br>1547<br>1497 | 449 (free base, MH$^+$) | |

TABLE 6

| Ex. No. | Compound | ¹H-NMR δ (ppm), 300 MHz | IR (cm⁻¹) | FAB-MS | Elemental analysis(%) |
|---|---|---|---|---|---|
| 9 | 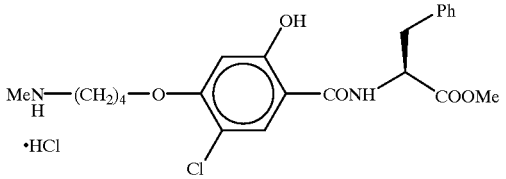 | DMSO-$d_6$<br>1.70–1.86(4H, m)<br>2.53(3H, s)<br>2.92–3.02(2H, m)<br>3.05–3.23(2H, m)<br>3.65(3H, s)<br>4.07–4.17(2H, m)<br>4.68–4.78(1H, m)<br>6.65(1H, s)<br>8.60(2H, brs)<br>8.99(1H, d, J=7.0Hz)<br>12.49(1H, brs) | | 435<br>(free base, MH⁺) | |
| 10 | 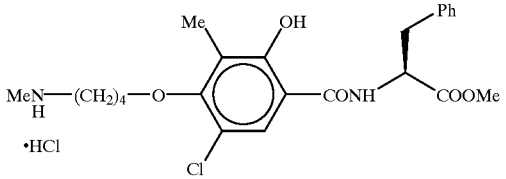 | DMSO-$d_6$<br>1.78–1.84(4H, m)<br>2.09(3H, s)<br>2.53(3H, bs)<br>2.95(2H, bs)<br>3.08–3.24(2H, m)<br>3.66(3H, s)<br>3.88–3.94(2H, m)<br>4.68–4.82(1H, m)<br>7.18–7.32(5H, m)<br>8.03(1H, s)<br>8.78(2H, bs)<br>9.29(1H, d, J=7.7Hz)<br>12.92(1H, s) | KBr<br>2950<br>2783<br>1745<br>1637<br>1544<br>1465<br>1369<br>1264 | 449<br>(free base, MH⁺) | |

TABLE 7

| Ex. No. | Compound | ¹H-NMR δ (ppm), 300 MHz | IR (cm⁻¹) | FAB-MS | Elemental analysis (%) |
|---|---|---|---|---|---|
| 11 | 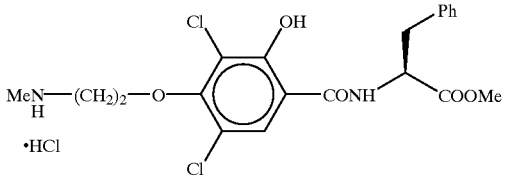 | DMSO-$d_6$<br>2.65–2.69(3H, m)<br>3.09–3.22(2H, m)<br>3.36–3.42(2H, m)<br>3.64–3.67(3H, m)<br>3.66(3H, s)<br>4.28(2H, t, J=6.0Hz)<br>4.74–4.81(1H, m)<br>7.19–7.29(5H, m)<br>8.23(1H, s)<br>8.95–9.03(2H, m)<br>9.53(1H, d, J=6.0Hz)<br>13.38(1H, s) | KBr<br>3422<br>2952<br>2730<br>1744<br>1942<br>1585<br>1458<br>1353<br>1221 | 441<br>free base, MH⁺) | $C_{20}H_{22}Cl_2N_2O_6 \cdot HCl$<br>Calculated<br>C, 50.28<br>H, 4.85<br>N, 5.86<br>Found<br>C, 50.19<br>H, 4.69<br>N, 5.74 |
| 12 | 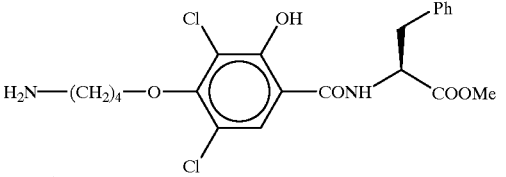 | DMSO-$d_6$<br>1.65–1.95(4H, m)<br>2.77–2.94(2H, m)<br>3.15(1H, dd, J=14.0, 9.Hz)<br>3.24(1H, dd, J=14.0, 6.0Hz)<br>3.66(3H, s)<br>4.00–4.14(2H, m)<br>4.65–4.90(1H, m)<br>7.15–7.40(5H, m)<br>7.87(3H, brs)<br>8.19(1H, s)<br>9.45(1H, d, J=6.0Hz)<br>13.35(1H, s) | KBr<br>2953<br>1641<br>1585<br>1542<br>1457<br>1355<br>1221 | 455<br>free base, MH⁺) | $C_{21}H_{24}Cl_2N_2O_5 \cdot HCl$<br>Calculated<br>C, 51.29<br>H, 5.12<br>N, 5.70<br>Found<br>C, 50.78<br>H, 5.17<br>N, 5.58 |

TABLE 8

| Ex. No. | Compound | $^1$H-NMR δ (ppm), 300 MHz | IR (cm$^{-1}$) | FAB-MS | Elemental analysis(%) |
|---|---|---|---|---|---|
| 13 | MeNH—(CH$_2$)$_4$—O-(3,5-dichloro-2-hydroxyphenyl)-CONH-CH(CH$_2$Ph)-COOMe | DMSO-d$_6$<br>1.63–1.95(4H, m)<br>2.55((3H, s)<br>2.92–3.07(4H, m)<br>3.57(3H, s)<br>3.88(2H, t, J=6.0Hz)<br>4.65–4.71(1H, m)<br>7.18–7.30(6H, m)<br>7.50(1H, s)<br>8.41(1H, brds)<br>12.25–12.27(1H, m) | KBr<br>3423<br>2951<br>1743<br>1618<br>1571<br>1541<br>1434<br>1205<br>1065 | 469 (MH$^+$) | |
| 14 | MeNH—(CH$_2$)$_4$—O-(3,5-dichloro-2-methoxyphenyl)-CONH-CH(CH$_2$Ph)-COOMe · HCl | DMSO-d$_6$<br>1.84(4H, s)<br>2.54(3H, s)<br>2.90–3.25(4H, m)<br>3.58(3H, s)<br>3.68(3H, s)<br>4.02(2H, m)<br>4.76(1H, m)<br>7.20–7.32(5H, m)<br>7.41(1h, m)<br>8.75(1H, d, J=9Hz) | | 483 (free base, MH$^+$) | |

TABLE 9

| Ex. No. | Compound | $^1$H-NMR δ (ppm), 300 MHz | IR (cm$^{-1}$) | FAB-MS | Elemental analysis (%) |
|---|---|---|---|---|---|
| 15 | MeNH—(CH$_2$)$_4$—O-(3,5-dichloro-2-hydroxyphenyl)-CONH-CH(CH$_2$-C$_6$H$_4$-OH)-COOMe · HCl | DMSO-d$_6$<br>1.79–1.89(4H, m)<br>2.55(2H, t, J=6.0Hz)<br>2.85–3.00(2H, m)<br>3.06(1H, dd, J=15.5, 8.4Hz)<br>3.57(3H, s)<br>3.65(3H, s)<br>4.01–4.11(1H, m)<br>4.50–4.53(2H, m)<br>4.59–4.71(1H, m)<br>6.66(2H, d, J=9.0Hz)<br>7.06(2H, d, J=6.0Hz)<br>8.20(1H, brs)<br>8.65(2H, brs)<br>9.26(1H, s)<br>9.40(1H, d, J=4.0Hz)<br>13.37(1H, s) | KBr<br>1640<br>1586<br>1515<br>1458<br>1354<br>1221 | 485 (free base, MH$^+$) | C$_{22}$H$_{26}$Cl$_2$N$_2$O$_6$·HCl<br>Calculated<br>C, 50.64<br>H, 5.22<br>N, 5.37<br>Found<br>C, 49.62<br>H, 5.29<br>N, 5.46 |

TABLE 10

| Ex. No. | Compound | ¹H-NMR δ (ppm), 300 MHz | IR (cm⁻¹) | FAB-MS | Elemental analysis (%) |
|---|---|---|---|---|---|
| 16 | EtNH—(CH₂)₄—O—[3,5-diCl-2-OH-phenyl]—CONH—CH(CH₂Ph)—COOMe ·HCl | DMSO-d₆ 1.20(3H, t, J=6.0Hz) 1.82–1.88(4H, m) 2.92–2.95(4H, m) 3.09–3.33(2H, m) 3.66(3H, s) 4.03–4.07(2H, m) 4.71–4.79(1H, m) 7.19–7.29(5H, m) 8.20(1H, s) 8.58–8.76(2H, m) 9.48(1H, d, J=6.0Hz) 13.35(1H, s) | KBr 2954 1747 1641 1584 1542 1458 1354 1219 | 483 (free base, MH⁺) | $C_{23}H_{28}Cl_2N_2O_5$·HCl Calculated C, 53.14 H, 5.62 N, 5.39 Found C, 52.54 H, 5.50 N, 5.40 |
| 17 | Me₂N—(CH₂)₄—O—[3,5-diCl-2-OH-phenyl]—CONH—CH(CH₂Ph)—COOMe | CDCl₃ 1.80–1.91(2H, m) 1.95–2.07(2H, m) 2.59(6H, s) 2.96–3.13(2H, m) 3.18–3.32(2H, m) 3.73(3H, s) 3.96–4.07(2H, m) 5.15(1H, 1, J=6Hz) 7.10–7.30(5H, m) 7.85(1H, s) 9.97(1H, brs) | Neat 2952 2360 1743 1633 1437 | 483 (MH⁺) | |

TABEL 11

| Ex. No. | Compound | ¹H-NMR δ (ppm), 300 MHz | IR (cm⁻¹) | FAB-MS | Elemental analysis (%) |
|---|---|---|---|---|---|
| 18 | Me₂N—(CH₂)₄—O—[3,5-diCl-2-OH-phenyl]—CONH—CH(CH₂Ph)—COOMe ·HCl | CDCl₃ 1.90–2.01(2H, m) 2.13–2.25(2H, m) 2.83(6H, s) 3.13–3.30(4H, m) 3.81(3H, s) 4.09(2H, t, J=6Hz) 5.02(1H, q, J=7Hz) 7.14–7.43(7H, m) 7.48(1H, s) | Neat 3241 2955 2671 1743 1640 1584 1461 | 483 (free base, MH⁺) | $C_{23}H_{28}Cl_2N_2O_5$·HCl Calculated C, 53.14 H, 5.62 N, 5.39 Found C, 53.24 H, 5.63 N, 5.34 |
| 19 | H₂N—(CH₂)₄—O—[3,5-diCl-2-OH-phenyl]—CONH—CH(CH₂Ph)—COOEt ·HCl | DMSO-d₆ 1.14(3H, t, J=6.0Hz) 1.70–1.95(4H, m) 2.80–2.95(2H, m) 3.05–3.28(2H, m) 3.95–4.15(4H, m) 4.60–4.75(1H, m) 7.18–7.40(5H, m) 7.91(3H, brs) 8.21(1H, s) 9.47(1H, d, J=6.0Hz) 13.36(1H, s) | KBr 2961 1722 1706 1643 1544 1459 1354 1216 | 469 (free base, MH⁺) | $C_{22}H_{26}Cl_2N_2O_5$·HCl Calculated C, 52.34 H, 5.19 N, 5.55 Found C, 51.62 H, 5.41 N, 5.48 |

TABLE 12

| Ex. No. | Compound | ¹H-NMR δ (ppm), 300 MHz | IR (cm⁻¹) | FAB-MS | Elemental analysis (%) |
|---|---|---|---|---|---|
| 20 | 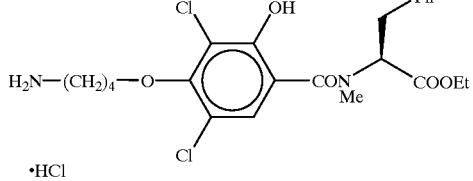 •HCl | DMSO-$d_6$<br>1.20(3H, t, J=7Hz)<br>1.81(4H, brs)<br>2.55–3.39(7H, m)<br>3.96(2H, brs)<br>4.01–4.28(2, 3H, m)<br>5.15(0.7H, m)<br>6.94–7.39(5H, m)<br>7.91(3H, brs)<br>10.14(1H, brs) | KBr<br>3422<br>2959<br>1736<br>1627<br>1447<br>1406<br>1333<br>1182 | 483 (free base, MH⁺) | $C_{23}H_{28}Cl_2N_2O_5 \cdot HCl$<br>Calculated<br>C, 53.14<br>H, 5.62<br>N, 5.39<br>Found<br>C, 52.85<br>H, 5.69<br>N, 5.24 |
| 21 | 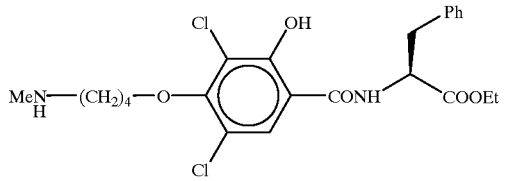 | CDCl₃<br>1.16(3H, t, J=8Hz)<br>1.50–1.75(4H, m)<br>2.38(3H, s)<br>2.90–3.05(2H, m)<br>3.26(2H, dq, J=12Hz)<br>3.30–3.45(2H, m)<br>4.00–4.10(2H, m)<br>5.02–5.10(1H, m)<br>7.10–7.15(2H, m)<br>7.20–7.30(3H, m)<br>8.00(1H, s)<br>10.76(1H, brs) | | 483 (MH⁺) | |

TABLE 13

| Ex. No. | Compound | ¹H-NMR δ (ppm), 300 MHz | IR (cm⁻¹) | FAB-MS | Elemental analysis (%) |
|---|---|---|---|---|---|
| 22 | 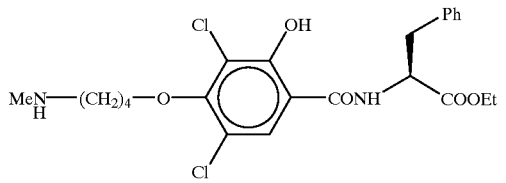 •HCl | DMSO-$d_6$<br>1.14(3H, t, J=6.0Hz)<br>1.77–1.91(4H, m)<br>2.54(3H, t, J=6.0Hz)<br>2.89–3.00(2H, m)<br>3.13(1H, dd, J=9.0, 15.0Hz)<br>3.22(1H, dd, J=6.6, 15.0Hz)<br>4.00–4.11(2H, m)<br>4.08(2H, q, J=6.0Hz)<br>4.68–4.79(1H, m)<br>7.18–7.32(5H, m)<br>8.21(1H, s)<br>8.72(2H, brs)<br>9.48(1H, d, J=6.9Hz)<br>13.36(1H, s) | KBr<br>1740<br>1584<br>1459<br>1352<br>1216 | 483 (free base, MH⁺) | $C_{23}H_{28}Cl_2N_2O_5 \cdot HCl$<br>Calculated<br>C, 53.14<br>H, 5.62<br>N, 5.39<br>Found<br>C, 53.36<br>H, 5.71<br>N, 5.53 |
| 23 | 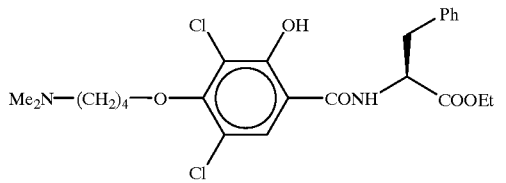 | CDCl₃<br>1.27(3H, t, J=7.5Hz)<br>1.82–2.04(4H, m)<br>2.55(6H, s)<br>2.95–3.11(2H, m)<br>3.25(2H, d, J=4Hz)<br>3.93–4.04(2H, m)<br>4.12–4.22(2H, m)<br>5.11–5.18(1H, m)<br>7.13–7.30(5H, m)<br>7.90(1H, s)<br>10.31(1H, brs) | Neat<br>2956<br>1738<br>1634<br>1574<br>1538<br>1440 | 497 (MH⁺) | |

TABLE 14

| Ex. No. | Compound | $^1$H-NMR δ (ppm), 300 MHz | IR (cm$^{-1}$) | FAB-MS | Elemental analysis (%) |
|---|---|---|---|---|---|
| 24 | 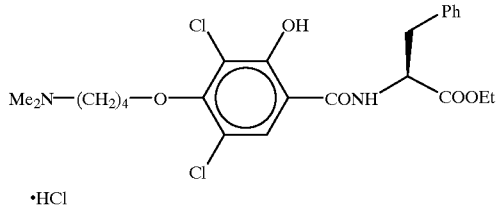 ·HCl | DMSO-d$_6$<br>1.13(3H, t, J=7.5Hz)<br>1.76–1.95(4H, m)<br>2.74(6H, s)<br>3.06–3.24(4H, m)<br>4.04–4.14(4H, m)<br>4.68–4.75(1H, m)<br>7.18–7.29(5H, m)<br>8.21(1H, s)<br>9.54(1H, brs) | Neat<br>2956<br>1738<br>1639<br>1583<br>1461 | 497<br>(free base, MH$^+$) | C$_{22}$H$_{26}$Cl$_2$N$_2$O$_5$·HCl<br>Calculated<br>C, 53.99<br>H, 5.85<br>N, 5.25<br>Found<br>C, 54.11<br>H, 5.86<br>N, 5.27 |
| 25 | 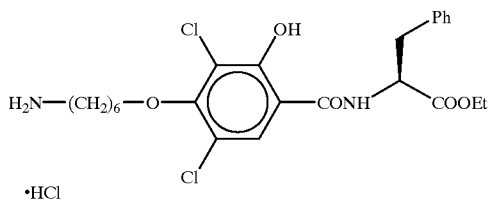 ·HCl | DMSO-d$_6$<br>1.13(3H, t, J=6.0Hz)<br>1.30–1.62(6H, m)<br>1.65–1.80(2H, m)<br>2.80–2.88(2H, m)<br>3.03–3.27(2H, m)<br>3.98–4.15(4H, m)<br>4.60–4.78(1H, m)<br>7.10–7.40(5H, m)<br>7.78(3H, brs)<br>8.19(1H, s)<br>9.44(1H, d, J=6.0Hz)<br>13.35(1H, s) | KBr<br>1641<br>1585<br>1458<br>1219 | 497<br>(free base, MH$^+$) | C$_{24}$H$_{30}$Cl$_2$N$_2$O$_5$·HCl<br>Calculated<br>C, 53.99<br>H, 5.85<br>N, 5.25<br>Found<br>C, 52.75<br>H, 5.59<br>N, 4.72 |

TABLE 15

| Ex. No. | Compound | $^1$H-NMR δ (ppm), 300 MHz | IR (cm$^{-1}$) | FAB-MS | Elemental analysis (%) |
|---|---|---|---|---|---|
| 26 | 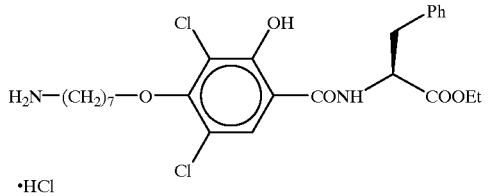 ·HCl | DMSO-d$_6$<br>1.13(3H, t, J=7.1Hz)<br>1.33–1.36(4H, m)<br>1.47–1.58(4H, m)<br>1.73–1.83(2H, m)<br>2.72–2.82(2H, m)<br>3.08–3.26(2H, m)<br>4.03(2H, t, J=6.4Hz)<br>4.11(2H, q, J=7.1Hz)<br>4.66–4.73(1H, m)<br>7.18–7.29(5H, m)<br>7.73–7.84(3H, m)<br>8.19(1H, s)<br>9.45(1H, d, J=7.1Hz)<br>13.36(1H, s) | KBr<br>3420<br>2936<br>1719<br>1641<br>1585<br>1543<br>1458<br>1352<br>1219 | 511<br>(free base, MH$^+$) | C$_{25}$H$_{32}$Cl$_2$N$_2$O$_5$·HCl<br>Calculated<br>C, 54.80<br>H, 6.07<br>N, 5.11<br>Found<br>C, 53.81<br>H, 6.10<br>N, 4.96 |
| 27 | 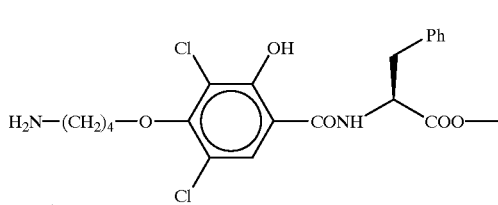 ·HCl | DMSO-d$_6$<br>1.08–1.10(3H, d, J=6.0Hz)<br>1.17–1.19(3H, d, J=6.0Hz)<br>1.82(4H, brs)<br>2.88(2H, brs)<br>3.10–3.30(2H, m)<br>4.04(2H, brs)<br>4.60–4.90(2H, m)<br>7.21–7.30(5H, m)<br>7.89(3H, brs)<br>8.19(1H, s)<br>9.50(1H, brs)<br>13.38(1H, brs) | KBr<br>3420<br>2981<br>1717<br>1641<br>1585<br>1458 | 483<br>(free base, MH$^+$) | C$_{23}$H$_{28}$Cl$_2$N$_2$O$_5$·HCl<br>Calculated<br>C, 53.14<br>H, 5.62<br>N, 5.39<br>Found<br>C, 51.51<br>H, 5.41<br>N, 4.99 |

TABLE 16

| Ex. No. | Compound | $^1$H-NMR δ (ppm), 300 MHz | IR (cm$^{-1}$) | FAB-MS | Elemental analysis (%) |
|---|---|---|---|---|---|
| 28 | H$_2$N—(CH$_2$)$_4$—O—[3,5-Cl$_2$-2-OH-phenyl]—CONH—CH(CH$_2$Ph)—COO—CH$_2$CH(CH$_3$)$_2$ · HCl | DMSO-d$_6$ 0.82(6H, d, J=6.0Hz) 1.74–1.90(4H, m) 2.80–2.95(2H, m) 3.10–3.28(3H, m) 3.86(2H, d, J=6.0Hz) 4.06–4.10(2H, m) 4.70–4.78(1H, m) 7.16–7.32(5H, m) 7.85(3H, brs) 8.19(1H, s) 9.45(1H, d, J=7.0Hz) 13.37(1H, s) | KBr 3385 2962 1721 1642 1585 1542 1458 1355 1218 | 497 (free base, MH$^+$) | C$_{24}$H$_{30}$Cl$_2$N$_2$O$_5$·HCl Calculated C, 55.99 H, 5.85 N, 5.25 Found C, 53.22 H, 5.94 N, 5.21 |
| 29 | MeNH—(CH$_2$)$_4$—O—[3,5-Cl$_2$-2-OH-phenyl]—CONH—CH(CH$_2$Ph)—COO—CH$_2$CH(CH$_3$)$_2$ · HCl | DMSO-d$_6$ 0.82(6H, d, J=6.7Hz) 1.75–1.90(5H, m) 2.54(3H, s) 2.90–3.30(4H, m) 3.85(2H, d, J=7.0Hz) 4.00–4.10(2H, m) 4.60–4.70(1H, m) 7.15–7.32(5H, m) 8.19(1H, s) 8.67(2H, brs) 9.50(1H, brs) 13.38(1H, s) | KBr 3360 2961 1740 1640 1584 1460 | 511 (free base, MH$^+$) | C$_{25}$H$_{32}$Cl$_2$N$_2$O$_5$·HCl Calculated C, 54.80 H, 6.07 N, 5.11 Found C, 54.59 H, 6.06 N, 4.98 |

TABLE 17

| Ex. No. | Compound | $^1$H-NMR δ (ppm), 300 MHz | IR (cm$^{-1}$) | FAB-MS | Elemental analysis (%) |
|---|---|---|---|---|---|
| 30 | H$_2$N—(CH$_2$)$_4$—O—[3,5-Cl$_2$-2-OH-phenyl]—CONH—CH(CH$_2$Ph)—COO—C(CH$_3$)$_3$ · HCl | DMSO-d$_6$ 1.35(9H, s) 1.70–1.94 2.77–3.01(2H, m) 3.05–3.18(2H, m) 4.00–4.10(2H, m) 4.52–4.68(1H, m) 7.15–7.34(5H, m) 7.80–8.03(3H, brs) 8.21(1H, s) 9.40(1H, brs) 13.44(1H,s) | KBr 2977 1640 1586 1386 1153 | 497 (free base, MH$^+$) | C$_{24}$H$_{30}$Cl$_2$N$_2$O$_5$·HCl Calculated C, 53.99 H, 5.85 N, 5.25 Found C, 53.83 H, 6.14 N, 5.07 |
| 31 | MeNH—(CH$_2$)$_4$—O—[3,5-Cl$_2$-2-OH-phenyl]—CONH—CH(CH$_2$Ph)—COO(CH$_2$)$_5$Me · HCl | DMSO-d$_6$ 0.81(3H, t, J=6.0Hz) 1.12–1.24(8H, m) 1.44–1.54(2H, m) 1.78–1.89(4H, m) 2.53–2.57(3H, m) 2.91–2.98(2H, m) 3.10–3.25(2H, m) 4.05(4H, t, J=6.0Hz) 4.68–4.75(1H, m) 7.16–7.35(5H, m) 8.20(1H, s) 8.70–8.78(2H, m) 9.48(1H, d, J=9.0Hz) 13.40(1H, s) | KBr 3423 2957 2856 1741 1638 1584 1541 1461 1411 1364 1259 1226 | 553 (free base, MH$^+$) | C$_{28}$H$_{38}$Cl$_2$N$_2$O$_5$·HCl Calculated C, 57.00 H, 6.66 N, 4.75 Found, C, 56.96 H, 6.83 N, 4.53 |

TABLE 18

| Ex. No. | Compound | $^1$H-NMR δ (ppm), 300 MHz | IR (cm$^{-1}$) | FAB-MS | Elemental analysis(%) |
|---|---|---|---|---|---|
| 32 | H$_2$N-C(=NH)-NH-(CH$_2$)$_4$-O-[3,5-Cl$_2$-2-OH-C$_6$H]-CONH-CH(CH$_2$Ph)-COOMe · HCl | DMSO-d$_6$<br>1.64–1.87(4H, m)<br>3.07–3.27(4H, m)<br>3.67(3H, s)<br>4.05(2H, t, J=6Hz)<br>4.71–4.81(1H, m)<br>6.90–7.60(10H, m)<br>7.73(1H, t, J=6Hz)<br>8.20(1H, s)<br>9.50(1H, d, J=9Hz)<br>13.35(1H, s) | Neat<br>3348<br>1726<br>1644<br>1584<br>1456 | 497 (free base, MH$^+$) | |
| 33 | H$_2$N-C(=NH)-NH-(CH$_2$)$_4$-O-[3,5-Cl$_2$-2-OH-C$_6$H]-CONH-CH(CH$_2$Ph)-COOEt · 2HCl | DMSO-d$_6$<br>1/14(3H, t, J=7.5Hz)<br>1.65–1.86(4H, m)<br>3.10–3.25(4H, m)<br>4.05(2H, t, J=6Hz)<br>4.11(2H, 1, J=6Hz)<br>4.68–4.77(1H, m)<br>6.88–7.60(10H, m)<br>7.76(1H, t, J=6Hz)<br>8.22(1H, s)<br>9.49(1H, d, J=9Hz)<br>13.36(1H, s) | Neat<br>3345<br>1721<br>1644<br>1584<br>1457 | 511 (free base, MH$^+$) | |

TABLE 19

| Ex. No. | Compound | $^1$H-NMR δ (ppm), 300 MHz | IR (cm$^{-1}$) | FAB-MS | Elemental analysis (%) |
|---|---|---|---|---|---|
| 34 | MeNH-(CH$_2$)$_4$-O-[3,5-Cl$_2$-2-OH-C$_6$H]-CONH-CH(CH$_2$-cyclohexyl)-COOMe · HCl | DMSO-d$_6$<br>0.80–1.48(5H, m)<br>1.50–1.90(10H, m)<br>2.55(3H, t, J=5.3Hz)<br>2.96(1H, brs)<br>3.66(3h, s)<br>4.04–4.12(2H, m)<br>4.52–4.62(1H, m)<br>8.29(1H, s)<br>8.68(2H, brs)<br>9.31(1H, d, J=6.8Hz)<br>13.54(1H, s) | KBr<br>3290<br>2925<br>1750<br>1584<br>1461<br>1225 | 475 (free base, MH$^+$) | C$_{22}$H$_{32}$Cl$_2$N$_2$O$_5$·HCl<br>Calculated<br>C, 51.62<br>H, 6.50<br>N, 5.47<br>Found<br>C, 51.65<br>H, 6.20<br>N, 5.73 |
| 35 | MeN(H)(CH$_2$)$_2$O(CH$_2$)$_2$-O-[3,5-Cl$_2$-2-OH-C$_6$H]-CONH-CH(CH$_2$Ph)-COOMe | DMSO-d$_6$<br>2.58(3H, s)<br>2.98–3.13(4H, m)<br>3.59(3H, s)<br>3.74–3.83(4H, m)<br>4.09(2H, t, J=6.0Hz)<br>4.66–4.74(1H, m)<br>7.20–7.28(7H, m)<br>7.53–7.69(1H, m) | KBr<br>3424<br>2952<br>1743<br>1625<br>1542<br>1435<br>1209<br>1067 | 485 (MH$^+$) | |

TABLE 20

| Ex. No. | Compound | $^1$H-NMR δ (ppm), 300 MHz | IR (cm$^{-1}$) | FAB-MS | Elemental analysis (%) |
|---|---|---|---|---|---|
| 36 | MeNH(CH$_2$)$_2$O(CH$_2$)$_2$-O-[3,5-Cl$_2$-2-OH-phenyl]-CONH-CH(CH$_2$Ph)-COOMe ·HCl | DMSO-d$_6$<br>2.54–2.58(3H, m)<br>3.09–3.22(4H, m)<br>3.66(3H, s)<br>3.78(2H, t, J=5.2Hz)<br>3.83(2H, t, J=4.5Hz)<br>4.22(2H, t, J=4.5Hz)<br>4.72–4.80(1H, m)<br>7.18–7.29(5H, m)<br>8.20(1H, s)<br>8.72(2H, m)<br>9.50(1H, d, J=6.5Hz)<br>13.36(1H, brds) | KBr<br>2953<br>2749<br>1745<br>1639<br>1584<br>1541<br>1468<br>1349<br>1220 | 485<br>(free base, MH$^+$) | C$_{22}$H$_{26}$Cl$_2$N$_2$O$_6$·HCl<br>Calculated<br>C, 50.64<br>H, 5.22<br>N, 5.37<br>Found<br>C, 50.64<br>H, 5.13<br>N, 5.27 |
| 37 | Me$_2$N(CH$_2$)$_2$O(CH$_2$)$_2$O-[3,5-Cl$_2$-2-OH-phenyl]-CONH-CH(CH$_2$Ph)-COOMe | CDCl$_3$<br>2.65(6H, s)<br>2.96–3.15(2H, m)<br>3.19–3.32(2H, m)<br>3.74(3H, s)<br>3.79–3.86(4H, m)<br>4.18(2H, t, J=6.0Hz)<br>5.09–5.13(1H, m)<br>7.12–7.14(2H, m)<br>7.21–7.28(4H, m)<br>7.76(1H, s)<br>9.18(1H, brds) | | 499<br>(MH$^+$) | |

TABLE 21

| Ex. No. | Compound | $^1$H-NMR δ (ppm), 300 MHz | IR (cm$^{-1}$) | FAB-MS | Elemental analysis (%) |
|---|---|---|---|---|---|
| 38 | MeNH(CH$_2$)$_2$O(CH$_2$)$_2$-O-[3,5-Cl$_2$-2-OH-phenyl]-CONH-CH(CH$_2$Ph)-COOEt | CDCl$_3$<br>1.25(3H, t, J=7.1Hz)<br>2.53(3H, s)<br>2.91–2.95(2H, m)<br>3.21–3.25(2H, m)<br>3.62–3.66(2H, m)<br>3.78–3.82(2H, m)<br>4.10–4.18(4H, m)<br>5.11–5.17(1H, m)<br>7.13–7.26(6H, m)<br>8.00(1H, s)<br>11.18(1H, brds) | | 499<br>(MH$^+$) | |
| 39 | MeNH(CH$_2$)$_2$O(CH$_2$)$_2$-O-[3,5-Cl$_2$-2-OH-phenyl]-CONH-CH(CH$_2$Ph)-COOEt ·HCl | DMSO-d$_6$<br>1.13(3H, t, J=7.0Hz)<br>2.56(3H, brds)<br>3.10–3.26(4H, m)<br>3.76(2H, t, J=5.0Hz)<br>3.81–3.85(2H, m)<br>4.11(2H, q, J=7.0Hz)<br>4.21–4.25(2H, m)<br>4.69–4.76(1H, m)<br>7.19–7.30(5H, m)<br>8.22(1H, s)<br>8.71(2h, m)<br>9.55–9.57(1H, m)<br>13.38(1H, brds) | KBr<br>2978<br>1743<br>1638<br>1584<br>1540<br>1469<br>1348<br>1260<br>1214 | 499<br>(free base, MH$^+$) | C$_{23}$H$_{28}$Cl$_2$N$_2$O$_6$·HCl<br>Calculated<br>C, 51.55<br>H, 5.45<br>N, 5.23<br>Found<br>C, 51.49<br>H, 5.44<br>N, 5.24 |

TABLE 22

| Ex. No. | Compound | $^1$H-NMR δ (ppm), 300 MHz | IR (cm$^{-1}$) | FAB-MS | Elemental analysis (%) |
|---|---|---|---|---|---|
| 40 | 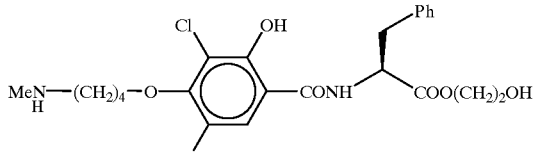 | DMSO-d$_6$<br>1.84(4H, brs)<br>2.54(3H, s)<br>2.95(2H, brs)<br>3.09–3.40(4H, m)<br>3.33(3H, s)<br>3.50–3.60(2H, m)<br>4.05(2H, brs)<br>4.11(2H, t, J=6Hz)<br>4.74–4.84(1H, m)<br>7.20–7.30(5h, m)<br>8.22(1H, s)<br>8.74(2H, brs)<br>9.50(1H, s) | | 499 (free base, MH$^+$) | |
| 41 | 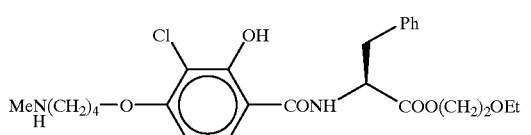 | DSMO-d$_6$<br>1.03(3H, t, J=6.2Hz)<br>1.83(4H, brs)<br>2.53(3H, t, J=5.3Hz)<br>2.80–3.60(6H, m)<br>4.05(2H, m)<br>4.20(2H, m)<br>4.76(1H, m)<br>7.20–7.40(5H, m)<br>8.19(1H, s)<br>8.55–8.85(2H, m)<br>9.48(1H, br)<br>13.37(1H, s) | | 527 (free base, MH$^+$) | |

TABLE 23

| Ex No. | Compound | $^1$H-NMR δ (ppm), 300 MHz | IR (cm$^{-1}$) | FAB-MS | Elemental analysis (%) |
|---|---|---|---|---|---|
| 42 | 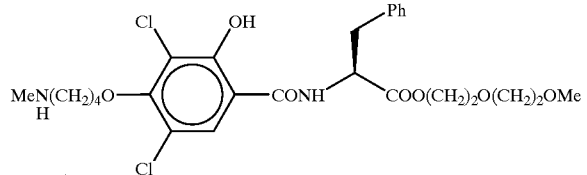 | DMSO-d$_6$<br>1.72–1.94(4H, m)<br>2.55(3H, t, J=5.5Hz)<br>2.85–3.02(2H, m)<br>3.20(3H, s)<br>3.04–3.28(2H, m)<br>3.30–3.42(2H, m)<br>3.48–3.62(2H, m)<br>3.93–4.08(2H, m)<br>4.09–4.21(2H, m)<br>4.77–4.84(1H, m)<br>7.18–7.35(5H, m)<br>8.20(1H, s)<br>8.67(2H, brs)<br>9.47(1H, d, J=5.0Hz)<br>13.37(1H, s) | | 555 (free base, MH$^+$) | |
| 43 | 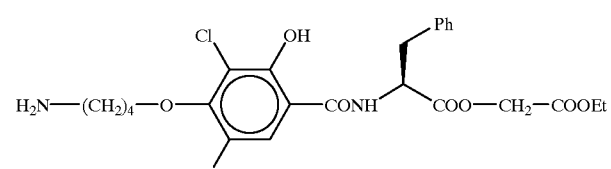 | DMSO-d$_6$<br>1.20(3H, t, J=7.4Hz)<br>1.80–1.84(4H, m)<br>2.82–2.92(2H, m)<br>3.14–3.32(2H, m)<br>4.00–4.04(2H, m)<br>4.12(2H, q, J=7.4Hz)<br>4.72(2H, s)<br>4.76–4.88(1H, m)<br>7.16–7.34(5H, m)<br>7.91(2H, bs)<br>8.21(1H, s)<br>9.54(1H, d, J=8.8Hz)<br>13.33(1H, s) | KBr<br>3426<br>2960<br>1751<br>1640<br>1585<br>1458<br>1178 | 527 (free base, MH$^+$) | |

TABLE 24

| Ex No. | Compound | $^1$H-NMR δ (ppm), 300 MHz | IR (cm$^{-1}$) | FAB-MS | Elemental analysis (%) |
|---|---|---|---|---|---|
| 44 | [Structure: 3,5-dichloro-2-hydroxy-4-(4-(methylamino)butoxy)benzoyl-Phe-OCH$_2$OCO-tBu · HCl] | DMSO-d$_6$ 1.11(9H, s) 1.77–1.91(4H, m) 2.54(3H, s) 2.75–3.25(4H, m) 4.00–4.10(2H, m) 4.40–4.80(1H, m) 5.76(2H, s) 7.20–7.40(5H, m) 8.17(1H, s) 8.74(2H, brs) 9.55(1H, brs) 13.29(1H, s) | Neat 2971 1754 1640 1584 1460 | 569 (free base, MH$^+$) | C$_{27}$H$_{34}$Cl$_2$N$_2$O$_7$·HCl Calculated C, 53.52 H, 5.82 N, 4.62 Found C, 53.34 H, 5.97 N, 4.39 |
| 45 | [Structure: 3,5-dichloro-2-hydroxy-4-(4-aminobutoxy)benzoyl-Phe-O-cyclohexyl · HCl] | DMSO-d$_6$ 1.15–1.90(14H, m) 2.82–2.93(2H, m) 3.10–3.24(2H, m) 4.01–4.08(2H, m) 4.65–4.75(2H, m) 7.18–7.32(5H, m) 7.92(3H, brs) 8.21(1H, s) 9.47(1H, d) 13.39(1H, brs) | KBr 3422 2939 1718 1641 1585 1458 | 523 (free base, MH$^+$) | C$_{26}$H$_{32}$Cl$_2$N$_2$O$_5$·HCl Calculated C, 55.77 H, 5.94 N, 5.00 Found C, 55.37 H, 6.02 N, 4.86 |

TABLE 25

| Ex No. | Compound | $^1$H-NMR δ (ppm), 300 MHz | IR (cm$^{-1}$) | FAB-MS | Elemental analysis (%) |
|---|---|---|---|---|---|
| 46 | [Structure: 3,5-dichloro-2-hydroxy-4-(4-(methylamino)butoxy)benzoyl-Phe-O-cyclohexyl · HCl] | DMSO-d$_6$ 1.13–1.92(10H, m) 2.55(3H, t, J=6.0Hz) 2.85–3.02(2H, m) 3.08–3.26(2H, m) 4.00–4.11(2H, m) 4.60–4.71(2H, m) 7.25–7.34(5H, m) 8.20(1H, s) 8.64(2H, brs) 9.43(1H, d, J=6.0Hz) 13.39(1H, s) | KBr 2938 1641 1584 1458 1357 1219 | 537 (free base, MH$^+$) | C$_{27}$H$_{34}$Cl$_2$N$_2$O$_5$·HCl Calculated C, 56.50 H, 6.15 N, 4.88 Found C, 54.51 H, 5.63 N, 4.64 |
| 47 | [Structure: 3,5-dichloro-2-hydroxy-4-(4-aminobutoxy)benzoyl-Phe-O-(2,6-dimethylcyclohexyl) · HCl] | DMSO-d$_6$ 0.66–0.88(4H, m) 0.92–1.92(8H, m) 2.50(6H, d, J=3.0Hz) 2.72–2.92(2H, m) 3.22–3.78(4H, m) 4.04–4.12(2H, m) 4.62–4.96(1H, m) 7.22–7.42(6H, m) 8.20(1H, s) 9.44(1H, br) 13.43(1H, s) | KBr 2929 1718 1642 1584 1458 1221 | 551 (free base, MH$^+$) | |

TABLE 26

| Ex No. | Compound | $^1$H-NMR δ (ppm), 300 MHz | IR (cm$^{-1}$) | FAB-MS | Elemental analysis (%) |
|---|---|---|---|---|---|
| 48 | H$_2$N—(CH$_2$)$_4$—O—[3,5-Cl$_2$,2-OH-phenyl]—CONH—CH(CH$_2$Ph)—COO—[1-Me-piperidin-4-yl] · 2HCl | DMSO-d$_6$<br>1.60–2.15(8H, m)<br>2.72(3H, s,)<br>2.80–3.60(6H, m)<br>4.05–4.10(2H, m)<br>4.60–4.91(2H, m)<br>7.20–7.39(6H, m)<br>7.82(3H, brs)<br>8.19–8.26(1H, m) | Neat<br>2964<br>1740<br>1674<br>1584<br>1458 | 538 (free base, MH$^+$) | |
| 49 | H$_2$N—(CH$_2$)$_4$—O—[3,5-Cl$_2$,2-OH-phenyl]—CONH—CH(CH$_2$Ph)—COO—adamantyl · HCl | DMSO-d$_6$<br>1.40–1.53(2H, m)<br>1.65–1.96(16H, m)<br>2.82–2.93(2H, m,)<br>3.13–3.40(2H, m)<br>4.05(2H, t, J=6Hz)<br>4.74–4.88(2H, m)<br>7.08–7.16(5H, m)<br>7.91(3H, brs)<br>8.21(1H, s)<br>9.48(1H, d, J=9Hz)<br>13.39(1H, s) | KBr<br>3386<br>2909<br>1718<br>1642<br>1585<br>1541<br>1456 | 575 (free base, MH$^+$) | |

TABLE 27

| Ex. No. | Compound | $^1$H-NMR δ (ppm), 300 MHz | IR (cm$^{-1}$) | FAB-MS | Elemental analysis (%) |
|---|---|---|---|---|---|
| 50 | MeNH—(CH$_2$)$_4$—O—[3,5-Cl$_2$,2-OH-phenyl]—CONH—CH(CH$_2$Ph)—CONHCH$_2$COOH · HCl | DMSO-d$_6$<br>1.75–1.91(4H, m)<br>2.54(3H, t, J=4.5Hz)<br>2.90–3.08(3H, m)<br>3.22(1H, dd, J=12, 3Hz)<br>3.82(2H, d, J=6Hz)<br>3.98–4.08(2H, m)<br>4.78–4.88(1H, m)<br>7.12–7.37(5H, m)<br>8.27(1H, s)<br>8.64(1H, t, J=6Hz)<br>8.70(2H, brs)<br>9.30(1H, d, J=6Hz)<br>13.20(1H, brs)<br>13.52(1H, s) | KBr<br>3398<br>2958<br>1736<br>1641<br>1585<br>1542 | 512 (free base, MH$^+$) | |
| 51 | MeNH—(CH$_2$)$_4$—O—[3,5-Cl$_2$,2-OH-phenyl]—CONH—CH(CH$_2$Ph)—CONHCH$_2$COOMe · HCl | DMSO-d$_6$<br>1.77–1.91(4H, m)<br>2.54(3H, t, J=6Hz)<br>2.95(2H, brs)<br>3.03(1H, dd, J=15, 12Hz)<br>3.22(1H, dd, J=15, 6Hz)<br>3.64(3H, s)<br>3.91(2H, d, J=6Hz)<br>4.00–4.09(2H, m)<br>4.77–4.87(1H, m)<br>7.13–7.38(5H, m)<br>8.27(1H, s)<br>8.70–8.87(3H, m)<br>9.34(1H, d, J=9Hz)<br>13.52(1H, s) | Neat<br>2951<br>1747<br>1661<br>1584<br>1556 | 526 (free base, MH$^+$) | |

TABLE 28

| Ex No. | Compound | $^1$H-NMR δ (ppm), 300 MHz | IR (cm$^{-1}$) | FAB-MS | Elemental analysis (%) |
|---|---|---|---|---|---|
| 52 | H$_2$N—(CH$_2$)$_4$—O—[3,5-Cl$_2$, 2-OH-C$_6$H]—CONH—CH(CH$_2$Ph)—COSEt · HCl | DMSO-d$_6$<br>1.17(3H, t, J=6.0Hz)<br>1.62–1.92(4H, m)<br>2.77–2.97(4H, m)<br>3.09(1H, dd, J=15.0, 12.0Hz)<br>3.11–3.35(1H, m)<br>3.99–4.12(2H, m)<br>4.82–4.96(1H, m)<br>7.13–7.36(5H, m)<br>7.92(2H, brs)<br>8.25(1H, s)<br>9.61–9.73(1H, m)<br>13.23(1H, s) | KBr<br>2930<br>1641<br>1584<br>1535<br>1457<br>1226 | 485<br>(free base, MH$^+$) | C$_{22}$H$_{26}$Cl$_2$N$_2$O$_4$S·HCl<br>Calculated<br>C, 50.63<br>H, 5.21<br>N, 5.37<br>Found<br>C, 50.40<br>H, 5.29<br>N, 5.28 |
| 53 | H$_2$N—(CH$_2$)$_4$—O—[3,5-Cl$_2$, 2-OH-C$_6$H]—CONH—CH(CH$_2$Ph)—COOCH$_2$Ph · HCl | DMSO-d$_6$<br>1.82(4H, m)<br>2.80(2H, m)<br>3.16(1H, dd, J=9, 12Hz)<br>3.24(1H, dd, J=6, 12Hz)<br>4.05(2H, brs)<br>4.81(1H, ddd, J=6, 7.9Hz)<br>5.14(1H, d, J=12Hz)<br>5.17(1H, d, J=12Hz)<br>7.16–7.39(10H, m)<br>7.91(3H, brs)<br>8.19(1H, s)<br>9.50(1H, d, J=7Hz)<br>13.32(1H, s) | KBr<br>3397<br>2958<br>1719<br>1642<br>1586<br>1543 | 531<br>(free base, MH$^+$) | C$_{27}$H$_{28}$Cl$_2$N$_2$O$_5$·HCl<br>Calculated<br>C, 57.11<br>H, 5.15<br>N, 4.93<br>Found<br>C, 56.97<br>H, 5.22<br>N, 5.15 |

TABLE 29

| Ex No. | Compound | $^1$H-NMR δ (ppm), 300 MHz | IR (cm$^{-1}$) | FAB-MS | Elemental analysis (%) |
|---|---|---|---|---|---|
| 54 | MeNH—(CH$_2$)$_4$—O—[3,5-Cl$_2$, 2-OH-C$_6$H]—CONH—CH(CH$_2$Ph)—COOCH$_2$Ph · HCl | DMSO-d$_6$<br>1.84(4H, brs)<br>2.54(3H, t, J=6Hz)<br>2.95(2H, brs)<br>3.16(1H, d, J=10, 12Hz)<br>3.25(1H, d, J=6, 12Hz)<br>4.05(2H, brs)<br>4.81(1H, ddd, J=6, 7, 9Hz)<br>5.14(1H, d, J=12Hz)<br>5.17(1H, d, J=12Hz)<br>7.28–7.87(10H, m)<br>8.19(1H, s)<br>8.75(2H, brs)<br>9.50(1H, d, J=7Hz)<br>13.32(1H, s) | KBr<br>3412<br>3300<br>2958<br>2789<br>1745<br>1639<br>1584<br>1541 | 545<br>(free base, MH$^+$) | C$_{28}$H$_{30}$Cl$_2$N$_2$O$_5$·HCl<br>Calculated<br>C, 57.79<br>H, 5.37<br>N, 4.81<br>Found<br>C, 57.34<br>H, 5.44<br>N, 4.78 |
| 55 | Me$_2$N—(CH$_2$)$_4$—O—[3,5-Cl$_2$, 2-OH-C$_6$H]—CONH—CH(CH$_2$Ph)—COOCH$_2$Ph · HCl | DMSO-d$_6$<br>1.76–1.95(4H, m)<br>2.75(6H, s)<br>3.05–3.30(4H, m)<br>4.06(2H, t, J=7Hz)<br>4.75–4.87(1H, m)<br>5.10–5.20(2H, m)<br>7.18–7.40(10H, m)<br>8.18(1H, s)<br>9.52(1H, brs)<br>10.20(1H, brs)<br>13.40(1H, brs) | KBr<br>2957<br>2690<br>1740<br>1638<br>1584<br>1456 | 558<br>(free base, MH$^+$) | C$_{29}$H$_{32}$Cl$_2$N$_2$O$_5$·HCl<br>Calculated<br>C, 58.45<br>H, 5.58<br>N, 4.70<br>Found<br>C, 58.18<br>H, 5.49<br>N, 4.72 |

TABLE 30

| Ex No. | Compound | ¹H-NMR δ (ppm), 300 MHz | IR (cm⁻¹) | FAB-MS | Elemental analysis (%) |
|---|---|---|---|---|---|
| 56 | 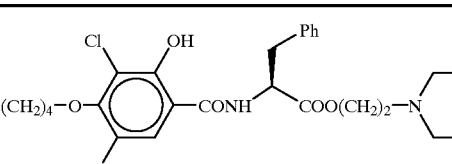 ·3HCl | DMSO-d₆ 1.82(4H, m) 2.95(2H, m) 3.08–3.55(12H, m) 4.04(2H, brs) 4.41(2H, m) 4.88(1H, m) 7.12–7.36(5H, m) 7.97(3H, brs) 8.31(1H, s) 9.63(3H, m) | KBr 3423 2957 1751 1638 1585 1542 1458 | 553 (free base, MH⁺) | $C_{26}H_{34}Cl_2N_4O_5 \cdot 3HCl$ Calculated C, 47.11 H, 5.63 N, 8.45 Found C, 45.84 H, 5.72 N, 7.76 |
| 57 | 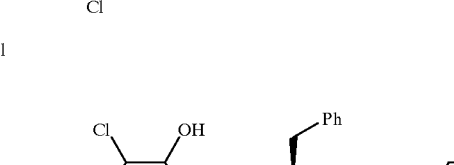 ·HCl | DMSO-d₆ 1.42–1.86(10H, m) 2.22–2.40(4H, m) 2.72–2.84(2H, m) 3.18–3.28(2H, m) 4.66–4.72(1H, m) 7.16–7.34(5H, m) 7.84(2H, br) 8.20, 8.22(1H, s) 9.34, 9.53 (1H, d, J=5.8Hz) 13.32, 13.48 (1H, s) | KBr 3422 2937 1752 1639 1584 1541 1457 1346 1227 | 536 (free base, MH⁺) | |

TABLE 31

| Ex No. | Compound | ¹H-NMR δ (ppm), 300 MHz | IR (cm⁻¹) | FAB-MS | Elemental analysis (%) |
|---|---|---|---|---|---|
| 58 | 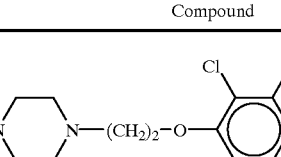 ·2HCl | DMSO-d₆ 2.81(3H, s) 3.13–3.80(10H, m) 4.27–4.47(2H, m) 4.66–4.83(1H, m) 7.13–7.32(5H, m) 8.22(1H, s) 9.49(1H, d, J=8.5Hz) 13.71(1H, brs) | KBr 1740 1641 1584 1457 1355 1220 | 510 (free base, MH⁺) | $C_{24}H_{29}Cl_2N_3O_5 \cdot 2HCl$ Calculated C, 49.42 H, 5.36 N, 7.20 Found C, 47.94 H, 5.52 N, 6.77 |
| 59 |  | DMSO-d₆ 1.15(3H, d, J=6.2Hz) 2.78–3.95(13H, m) 3.67(3H, s) 4.54–4.72(1H, m) 7.17–7.34(5H, m) 7.45(1H, s) 8.69–8.82(1H, m) 12.27–12.36(1H, m) | | 510(MH⁺) | |

TABLE 32

| Ex No. | Compound | $^1$H-NMR δ (ppm), 300 MHz | IR (cm$^{-1}$) | FAB-MS | Elemental analysis (%) |
|---|---|---|---|---|---|
| 60 | [structure with piperazine-Me, CH₂CH₂-O-dichlorophenol-CONH-CH(CH₂Ph)-COOMe] · 2HCl | DMSO-d₆ 1.30(3H, d, J=6Hz) 3.00–3.70(11H, m) 3.67(3H, s) 4.42(2H, s) 4.76(1H, m) 7.18–7.30(5H, m) 8.23(1H, s) 9.52(1H, d, J=9Hz) 9.80(1H, br) 13.39(1H, br) | | 510 (free base, MH⁺) | |
| 61 | [structure with (S)-piperazine-Me, CH₂CH₂-O-dichlorophenol-CONH-CH(CH₂Ph)-COOMe] · 2HCl | DMSO-d₆ 1.29(3H, d, J=6.3Hz) 3.00–3.20(9H, m) 3.66(3H, s) 4.41(2H, brs) 4.77(1H, m) 7.15–7.30(5H, m) 8.22(1H, s) 9.49(1H, d, J=7.6Hz) 9.70(2H, br) 13.35(1H, brs) | KBr 3427 1736 1641 1458 1222 | 510 (free base, MH⁺) | Optical rotation: [α]$^{25}_D$ = −53.0° (c = 0.37, MeOH) |

TABLE 33

| Ex. No. | Compound | $^1$H-NMR δ (ppm), 300MHz | IR (cm$^{-1}$) | FAB-MS | Elemental analysis (%) |
|---|---|---|---|---|---|
| 62 | [structure with (R)-piperazine-Me, CH₂CH₂-O-dichlorophenol-CONH-CH(CH₂Ph)-COOMe] · 2HCl | DMSO-d₆ 1.30(3H, d, J=6.0Hz) 3.09–3.83 (11H, m) 3.67(3H, s) 4.34–4.47(2H, m) 4.73–6.81(1H, m) 7.17–7.29(5H, m) 8.23(1H, s) 9.51(1H, d, J=6.0Hz) 9.63–9.92(1H, m) 13.35–13.47(1H, m) | KBr 3425 2450 1747 1664 1452 1248 1213 | 510 (free base, MH⁺) | C₂₄H₂₉Cl₂N₃O₅·2HCl Calculated C, 54.16 H, 5.13 N, 6.11 Found C, 53.21 H, 5.25 N, 5.96 |
| 63 | [structure with dimethyl-piperazine, CH₂CH₂-O-dichlorophenol-CONH-CH(CH₂Ph)-COOMe] · 2HCl | DMSO-d₆ 1.34(3H, d, J=8Hz) 2.80(3H, s) 3.00–3.70(11H, m) 3.67(3H, s) 4.37(2H, brs) 4.75(1H, m) 7.15–7.32(5H, m) 8.22(1H, s) 9.50(1H, d, J=6Hz) 13.39(1H, s) | | 524 (free base, MH⁺) | |

TABLE 34

| Ex. No. | Compound | ¹H-NMR δ (ppm), 300MHz | IR (cm⁻¹) | FAB-MS | Elemental analysis (%) |
|---|---|---|---|---|---|
| 64 | 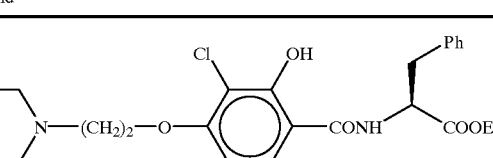 •HCl | DMSO-d₆ 1.14(3H, t, J=7.6Hz) 2.48–2.52(8H, m) 3.14–3.38(4H, m) 4.11(2H, q, J=7.6Hz) 4.39(2H, bs) 4.68–4.80(1H, m) 7.18–7.32(5H, m) 8.23(1H, s) 9.47(1H, d, J=8.8Hz) | KBr 2950 2784 1745 1637 1589 1544 1465 1369 1264 1097 | 510 (free base, MH⁺) | |
| 65 | 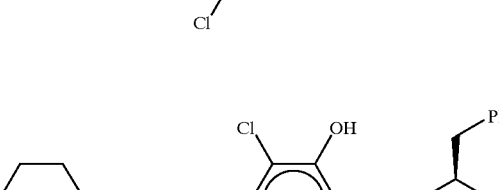 | DMSO-d₆ 1.11(3H, t, J=6.0Hz) 2.60–3.20(13H, m) 4.00–4.10(4H, m) 4.62–4.66(1H, m) 7.20–7.30(5H, m) 7.75(1H, s) | KBr 3422 2940 2360 1736 1638 1456 | 524 (MH⁺) | |

TABLE 35

| Ex. No. | Compound | ¹H-NMR δ (ppm), 300 MHz | IR (cm⁻¹) | FAB-MS | Elemental analysis (%) |
|---|---|---|---|---|---|
| 66 | 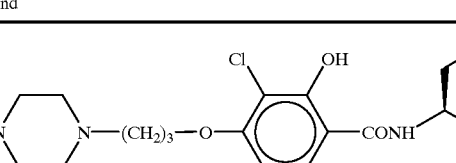 •2HCl | DMSO-d₆ 2.10–2.35 (2H, m) 2.80(3H, s) 3.10–3.94(12H, m) 3.66(3H, s) 4.10–4.22 (2H, m) 4.62–4.72(1H, m) 7.20–7.41(5H, m) 8.20(1H, s) 9.47(1H, d, J=6.0Hz) 13.3(1H, brs) | KBr 3423 1740 1640 1584 1458 1356 1219 | 524 (free base, MH⁺) | $C_{25}H_{31}Cl_2N_3O_5 \cdot 2HCl$ Calculated C, 50.27 H, 5.57 N, 7.03 Found C, 49.88 H, 5.56 N, 6.93 |
| 67 | 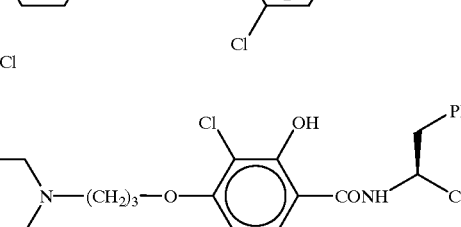 •2HCl | DMSO-d₆ 1.14(3H, t, J=6.0Hz) 2.23(2H, m) 3.00–3.05(10H, m) 4.05–4.16(4H, m) 4.67–4.77(1H, m) 7.12–7.35(5H, m) 7.50–7.66(1H, m) 8.21(1H, brs) 9.40–9.60(1H, brs) 9.45(1H, d, J=6.0Hz) 13.40(1H, brs) | KBr 2361 2343 1584 1458 1352 1216 | 524 (free base, MH⁺) | $C_{25}H_{31}Cl_2N_3O_5 \cdot 2HCl$ Calculated C, 50.27 H, 5.57 N, 7.03 Found C, 49.68 H, 5.68 N, 6.66 |

TABLE 36

| Ex. No. | Compound | $^1$H-NMR δ (ppm), 300 MHz | IR (cm$^{-1}$) | FAB-MS | Elemental analysis (%) |
|---|---|---|---|---|---|
| 68 | 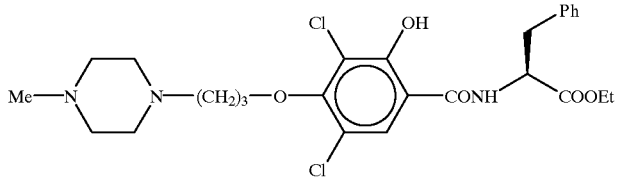 •2HCl | DMSO-d$_6$ 1.21(3H, t, J=8Hz) 2.25(2H, brs) 2.82(3H, s) 3.08–3.90(12H, m) 4.06–4.13 (4H, m) 4.70(1H, m) 7.16–7.28 (5H, m) 8.21(1H, s) 9.45(1H, d, J=8Hz) 13.36(1H, brs) | | 538 (free base, MH$^+$) | |
| 69 | 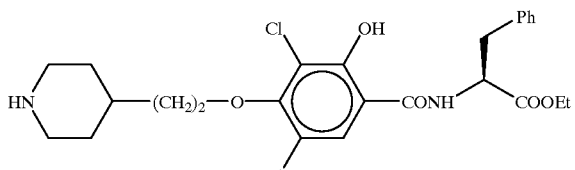 •HCl | DMSO-d$_6$ 1.12(3H, t, J=6.9Hz) 1.29–1.47(2H, m) 1.73(2H, dd, J=5.7, 12.0Hz) 1.80–1.95 (4H, m) 2.85(2H, m) 3.07–3.28 (4H, m) 4.04–4.13(4H, m) 4.67–4.75(1H, m) 7.16–7.28 (5H, m) 8.20(1H, s) 8.65(1H, brs) 8.87(1H, brs) 9.50(1H, brs) 13.35(1H, brs) | KBr 3372 2940 2805 2726 2489 1739 1642 1585 1544 1460 1412 1360 1352 1219 | 509 (free base, M$^+$) | |

TABLE 37

| Ex. No. | Compound | $^1$H-NMR δ (ppm), 300 MHz | IR (cm$^{-1}$) | FAB-MS | Elemental analysis (%) |
|---|---|---|---|---|---|
| 70 | 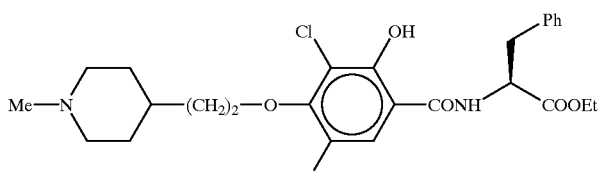 •HCl | DMSO-d$_6$ 1.23(3H, t, J=7.1Hz) 1.42–1.57 (2H, m) 1.68–1.98 (5H, m) 2.69(3H, s) 2.88–2.96(2H, m) 3.10–3.24(2H, m) 3.31–3.39(2H, m) 4.05–4.14(4H, m) 4.72(1H, ddd, J=6.3, 7.5, 9.1Hz) 7.15–7.29 (5H, m) 8.21(1H, s) 9.48(1H, d, J=7.5Hz) 10.34(1H, brs) 13.35 (1H, brs) | KBr 3406 2938 1736 1638 1584 1460 1412 1352 1215 1075 957 701 | 523 (free base, MH$^+$) | |
| 71 | 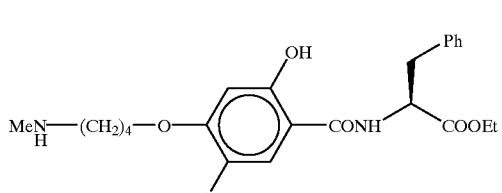 •HCl | CDCl$_3$ 1.13(3H, t, J=7.0Hz) 1.70–1.88 (4H, m) 2.49–2.53(5H, m) 3.07–3.21(2H, m) 4.06–4.13(4H, m) 4.69 (1H, dd, J=8.4, 15.6Hz) 6.67(1H, s) 7.18–7.32(5H, m) 8.04(1H, s) 8.75(1H, brs) 8.99(1H, d, J=7.2Hz) 12.51(1H, brs) | | 449.1 (free base, MH$^+$) | C$_{23}$H$_{30}$Cl$_2$N$_2$O$_5$·HCl Calculated C, 56.91 H, 6.23 N, 5.77 Found C, 56.90 H, 6.29 N, 5.73 |

TABLE 38

| Ex. No. | Compound | $^1$H-NMR δ (ppm), 300MHz | IR (cm$^{-1}$) | FAB-MS | Elemental analysis (%) |
|---|---|---|---|---|---|
| 72 | 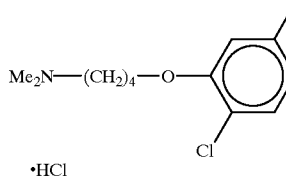 Me$_2$N—(CH$_2$)$_4$—O—[ring: OH, Cl, CONH—CH(CH$_2$Ph)—COOEt] ·HCl | DMSO-d$_6$ 1.13(3H, t, J=7.0 Hz) 1.75–1.90(4H, brs) 2.74(3H, s) 2.75(3H, s) 3.12–3.33(4H, m) 4.10(4H, m) 4.70(1H, dd, J=4.3, 14.4Hz) 6.65(1H, brs) 7.21–7.29(5H, m) 8.04(1H, s) 8.98(1H, d, J=7.8Hz) 12.51(1H, s) | KBr 3428 2958 2686 1736 1637 1604 1541 1493 1375 1267 1198 | 463 (free base, MH$^+$) | |
| 73 | 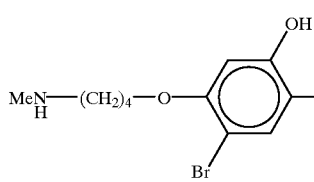 MeNH—(CH$_2$)$_4$—O—[ring: OH, Br, CONH—CH(CH$_2$Ph)—COOMe] ·HCl | CDCl$_3$ 1.95–2.10(4H, m) 2.70(3H, s) 3.11(2H, t, J=7.5Hz) 3.21(2H, m) 3.77(3H, s) 4.01(2H, t, J=6.0Hz) 5.00(1H, m) 6.38(1H, s) 7.02(1H, d, J=7.2Hz) 7.14–7.32(5H, m) 7.52(1H, s) 9.43(2H, brs) 12.2(1H, s) | KBr 1741 1637 1489 1265 | 479 free base, MH$^+$) | |

TABLE 39

| Ex. No. | Compound | $^1$H-NMR δ (ppm), 300MHz | IR (cm$^{-1}$) | FAB-MS | Elemental analysis (%) |
|---|---|---|---|---|---|
| 74 | 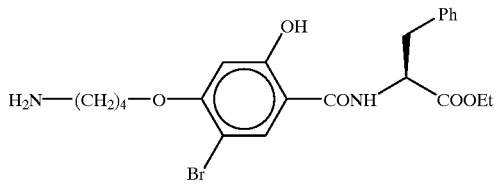 H$_2$N—(CH$_2$)$_4$—O—[ring: OH, Br, CONH—CH(CH$_2$Ph)—COOEt] ·HCl | DMSO-d$_6$ 1.13(3H, t, J=7.0 Hz) 1.70–1.89(4H, m) 2.87(2H, m) 3.2(2H, m) 4.0–4.1(4H, m) 4.7(1H, m) 6.65(1H, s) 7.15–7.30(5H, m) 7.92(3H, brs) 8.17(1H, s) 8.98(1H, d, J=5.6Hz) 12.51(1H, s) | KBr 1736 1601 1489 1373 1263 | 479 (free base, MH$^+$) | C$_{22}$H$_{27}$BrN$_2$O$_5$·HCl Calculated C, 5.123 H, 5.47 N, 5.43 Found C, 50.93 H, 5.51 N, 5.34 |
| 75 | 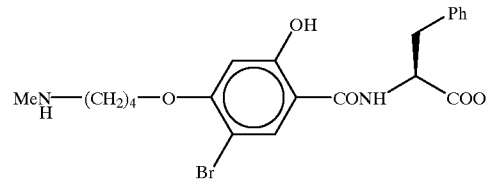 MeNH—(CH$_2$)$_4$—O—[ring: OH, Br, CONH—CH(CH$_2$Ph)—COOEt] ·HCl | CDCl$_3$ 1.27(3H, t, J=7.2 Hz) 1.93–2.02(2H, m) 2.07–2.17(2H, m) 2.71(3H, s) 3.1–3.2(2H, m) 3.2–3.3(2H, m) 4.03(2H, t, J=6Hz) 4.23(2H, q, J=7Hz) 4.98(1H, dt, J=7, 6Hz) 6.39(1H, s) 6.88(1H, d, J=7.8Hz) 7.14–7.18(2H, m) 7.22–7.32(3H, m) 7.49(1H, s) 9.51(2H, brs) 12.29(1H, brs) | KBr 3374 2960 1736 1638 1599 1376 1266 1199 | 493 (free base, MH$^+$) | |

TABLE 40

| Ex. No. | Compound | $^1$H-NMR δ (ppm), 300MHz | IR (cm$^{-1}$) | FAB-MS | Elemental analysis (%) |
|---|---|---|---|---|---|
| 76 | 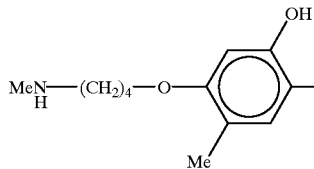 •HCl | DMSO-d$_6$ 1.91(4H, m) 2.12(3H, s) 2.57(3H, s) 2.98(2H, m) 3.10–3.30(2H, m) 3.70(3H, s) 3.99(2H, m) 4.78(1H, m) 6.35(1H, s) 7.15–7.30(5H, m) 7.65(1H, s) 8.62(1H, brs) 9.24(2H, brs) 12.09(1H, s) | | 449 (free base, M−1) | |
| 77 | 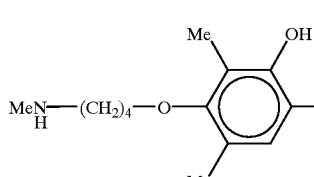 •HCl | CDCl$_3$ 1.13(3H, t, J=7Hz) 1.85–1.95(4H, m) 2.04(3H, s) 2.18(3H, s) 2.51(3H, s) 2.93(2H, m) 3.16–3.20(2H, m) 3.76(2H, m) 4.10(2H, q, J=7Hz) 4.69(1H, m) 7.17–7.32(5H, m) 7.71(1H, s) 9.01(2H, brs) 9.07(1H, d, J=8Hz) 12.66(1H, s) | | 442 (free base, MH$^+$) | |

TABLE 41

| Ex. No. | Compound | $^1$H-NMR δ (ppm), 300MHz | IR (cm$^{-1}$) | FAB-MS | Elemental analysis (%) |
|---|---|---|---|---|---|
| 78 | 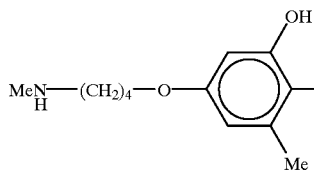 •HCl | DMSO-d$_6$ 1.63–1.78(4H, m) 2.02(3H, s) 2.55(3H, s) 2.82–3.11(4H, m) 3.62(3H, s) 3.84–3.95(2H, m) 4.58–4.65(1H, m) 6.21(1H, d, J=2.4Hz) 6.24(1H, d, J=2.4Hz) 7.18–7.36(5H, m) 8.38(1H, d, J=7.5Hz) 8.62–8.78(2H, m) 9.70(1H, brs) | | 415 (free base, MH$^+$) | |
| 79 | 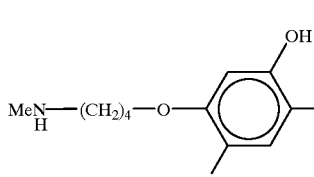 •HCl | DMSO-d$_6$ 1.80(4H, m) 2.50(3H, m) 2.95(2H, m) 3.08–3.22(2H, m) 3.65(3H, s) 3.95–4.15(2H, m) 4.60–4.75(3H, m) 6.54(1H, s) 7.15–7.32(5H, m) 7.99(1H, s) 8.68(2H, brs) 8.93(1H, d, J=8Hz) 12.54(1H, s) | | 431 (free base, MH$^+$) | |

TABLE 42

| Ex. No. | Compound | ¹H-NMR δ (ppm), 300MHz | IR (cm⁻¹) | FAB-MS | Elemental analysis (%) |
|---|---|---|---|---|---|
| 80 | MeNH—(CH$_2$)$_4$—O—[Ar(OH, Br, Me)]—CONH—CH(CH$_2$Ph)—COOMe ·HCl | DMSO-d$_6$ 1.71–1.83(4H, m) 2.02(3H, s) 2.55(3H, s) 2.88–3.11(4H, m) 3.63(3H, s) 3.92–4.03(1H, m) 6.45(1H, s) 7.08–7.37(5H, m) 8.57–8.78(2H, m) 8.59(1H, d, J=7.8Hz) 9.80(1H, brs) | | 493 (free base, MH⁺) | |
| 81 | MeNH—(CH$_2$)$_4$—O—[Ar(Br, OH, Br, Me)]—CONH—CH(CH$_2$Ph)—COOMe ·HCl | DMSO-d$_6$ 1.79–1.93(4H, m) 2.00(3H, s) 2.56(3H, s) 2.91–3.11(4H, m) 3.63(3H, s) 3.83–3.95(2H, m) 4.60–4.66(1H, m) 7.20–7.36(5H, m) 8.54–8.66(2H, m) 8.93(1H, d, J=7.8Hz) 9.61(1H, s) | | 571 (free base, MH⁺) | |

TABLE 43

| Ex. No. | Compound | ¹H-NMR δ (ppm), 300MHz | IR (cm⁻¹) | FAB-MS | Elemental analysis (%) |
|---|---|---|---|---|---|
| 82 | MeNH—(CH$_2$)$_4$—O—[Ar(Cl, OH, Cl)]—CONH—CH(CH$_2$Ph)—COOCH$_2$COOEt ·HCl | DMSO-d$_6$ 1.19 (3H, t, J=7.1Hz) 1.83(4H, brs) 2.48–2.53(5H, m) 2.94(2H, brs) 3.16–3.34(5H, m) 4.02–4.18(4H, m) 4.76(2H, d, J=2.2Hz) 4.84–4.92(1H, m) 7.16–7.36(5H, m) 8.22(1H, s) 8.87(2H, brs) 9.56(1H, d, J=7.2Hz) 13.31(1H, s) | KBr 2961 1750 1461 1178 | 541 (free base, MH⁺) | C$_{25}$H$_{30}$Cl$_2$N$_2$O$_7$·HCl Calculated C, 51.96 H, 5.41 N, 4.85 Found C, 51.88 H, 5.40 N, 4.82 |
| 83 | MeNH—(CH$_2$)$_4$—O—[Ar(Cl, OH, Cl)]—CONH—CH(CH$_2$Ph)—COO—[C$_6$H$_4$]—COOEt ·HCl | DMSO-d$_6$ 1.32 (3H, t, J=7.0Hz) 1.82(4H, brs) 2.57(3H, brs) 2.97(2H, brs) 4.06(2H, brs) 4.32(2H, q, J=7.0Hz) 4.99(1H, dd, J=5.7, 14.1Hz) 7.16–7.36(7H, m) 8.01(2H, d, J=8.7Hz) 8.23(1H, brs) 8.33(2H, brs) 9.66(1H, brs) 11.3(1H, brs) | KBr 3426 2960 1717 1641 1604 1457 1278 1162 | 603 (free base, M⁺) | C$_{30}$H$_{33}$O$_7$N$_2$O$_3$·HCl Calculated C, 56.31 H, 5.20 N, 4.38 Found C, 54.81 H, 5.30 N, 4.34 |

TABLE 44

| Ex. No. | Compound | $^1$H-NMR δ (ppm), 300 MHz | IR (cm$^{-1}$) | FAB-MS | Elemental analysis (%) |
|---|---|---|---|---|---|
| 84 | 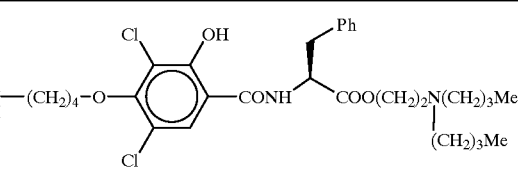 •2HCl | DMSO-d$_6$<br>1.15(6H, t, J=7 Hz)<br>1.75–2.00(6H, m)<br>2.49(3H, s)<br>2.90–3.05(8H, m)<br>3.10–3.25(2H, m)<br>4.00–4.21(4H, m)<br>4.74(1H, m)<br>7.17–7.30(5H, m)<br>8.28(1H, s)<br>8.88(2H, brs)<br>9.64(1H, brs)<br>10.43(1H, brs)<br>13.37(1H, brs) | | 568 (free base, MH$^+$) | |
| 85 | •2HCl | DMSO-d$_6$<br>1.28(12H, m)<br>1.84(4H, m)<br>2.53(3H, t, J=5.7 Hz)<br>2.94(2H, m)<br>3.13–3.93(4H, m)<br>3.63(2H, m)<br>4.01(2H, m)<br>4.37–4.48(1H, m)<br>7.18–7.29(5H, m)<br>8.31(1H, s)<br>8.86(2H, brs)<br>9.70(1H, brs)<br>10.03(1H, brs)<br>13.37(1H, brs) | | 582 (free base, MH$^+$) | |

TABLE 45

| Ex. No. | Compound | $^1$H-NMR δ (ppm), 300 MHz | IR (cm$^{-1}$) | FAB-MS | Elemental analysis (%) |
|---|---|---|---|---|---|
| 86 |  •2HCl | DMSO-d$_6$<br>0.72–0.97(6H, m)<br>1.18–1.42(4H, m)<br>1.51–1.73(4H, m)<br>1.75–1.83(4H, m)<br>2.83–3.15(6H, m)<br>3.16–3.39(5H, m)<br>4.02–4.10(2H, m)<br>4.37–4.55(2H, m)<br>4.75–4.91(1H, m)<br>7.20–7.30(5H, m)<br>8.36(1H, s)<br>8.68–8.96(2H, m)<br>9.74–9.88(1H, m)<br>10.56–10.73(1H, m)<br>13.32–13.47(1H, m) | | 610 (free base, MH$^+$) | |
| 87 | | CDCl$_3$<br>1.80–1.89(2H, m)<br>1.91–2.01(2H, m)<br>3.21(1H, dd, J=14, 6 Hz)<br>3.28(1H, dd, J=14, 6 Hz)<br>3.76(2H, t, J=7 Hz)<br>3.80(3H, s)<br>4.12(2H, t, J=6 Hz)<br>5.03(1H, ddd, J=8, 6, 6 Hz)<br>6.77(1H, d, J=8 Hz)<br>7.09–7.13(2H, m)<br>7.28–7.35(3H, m)<br>12.64(1H, s) | | 455 (free base, MH$^+$) | |

TABLE 46

| Ex. No. | Compound | $^1$H-NMR δ (ppm), 300 MHz | IR (cm$^{-1}$) | FAB-MS | Elemental analysis (%) |
|---|---|---|---|---|---|
| 88 | MeNH-(CH$_2$)$_4$-[phenyl(OH)]-CONH-CH(CH$_2$Ph)-COOMe ·HCl | DMSO-d$_6$<br>1.70(2H, m)<br>1.85(2H, m)<br>2.04(2H, m)<br>2.62(3H, s)<br>2.93(2H, brs)<br>3.18–3.20(2H, m)<br>3.76(3H, s)<br>5.01(1H, m)<br>6.65(1H, d, J=7 Hz)<br>6.78(1H, s)<br>7.09–7.32(5H, m)<br>9.35(2H, brs)<br>11.87(1H, s) | | 384<br>(free base, MH$^+$) | |
| 89 | MeNH-(CH$_2$)$_5$-[phenyl(OH)]-CONH-CH(CH$_2$Ph)-COOMe ·HCl | DMSO-d$_6$<br>1.30(2H, m)<br>1.58(4H, m)<br>2.49(3H, s)<br>2.82(2H, t, J=8 Hz)<br>3.11(1H, dd, J=14, 9 Hz)<br>3.19(1H, dd, J=14, 6 Hz)<br>3.65(3H, s)<br>4.74(1H, m)<br>6.75(2H, m)<br>7.18–7.31(5H, m)<br>7.81(1H, d, J=9 Hz)<br>8.75(2H, brs)<br>9.00(1H, d, J=8 Hz) | | 399<br>(free base, MH$^+$) | |

TABLE 47

| Ex. No. | Compound | $^1$H-NMR δ (ppm), 300 MHz | IR (cm$^{-1}$) | FAB-MS | Elemental analysis (%) |
|---|---|---|---|---|---|
| 90 | MeNH-(CH$_2$)$_6$-[phenyl(OH)]-CONH-CH(CH$_2$Ph)-COOMe ·HCl | CDCl$_3$<br>1.25–1.45(4H, m)<br>1.55–1.64(2H, m)<br>1.77–1.87(2H, m)<br>2.54(2H, t, J=7.5 Hz)<br>2.64(3H, s)<br>2.90(2H, t, J=7.8 Hz)<br>3.23(2H, m)<br>6.63(2H, dd, J=8.1, 1.8 Hz)<br>6.77(1H, d, J=1.5 Hz)<br>6.88(2H, d, J=7.8 Hz)<br>7.10–7.32(6H, m)<br>9.38(2H, brs)<br>11.90(1H, brs) | | 413<br>(free base, MH$^+$) | |

TABLE 48

| Ex. No. | Compound | $^1$H-NMR δ (ppm), 300 MHz | IR (cm$^{-1}$) | FAB-MS | Elemental analysis (%) |
|---|---|---|---|---|---|
| 91 | MeNH—(CH$_2$)$_5$—[3,5-dichloro-2-hydroxyphenyl]-CONH-CH(CH$_2$Ph)-COOMe · HCl | CDCl$_3$<br>1.45–1.65(4H, m)<br>1.90–2.00(2H, m)<br>2.67(3H, s)<br>2.86–2.90(2H, t, J=7.5 Hz)<br>2.80–3.05(2H, m)<br>3.18–3.31(2H, m)<br>3.80(3H, s)<br>5.00–5.05(1H, m)<br>7.15–7.32(6H, m)<br>9.48(2H, brs)<br>12.44(1H, s) | KBr<br>3429<br>2949<br>1743<br>1641<br>1587 | 467.0 (free base, MH$^+$) | C$_{23}$H$_{28}$Cl$_2$N$_2$O$_4$·HCl<br>Calculated<br>C, 54.83<br>H, 5.80<br>N, 5.56<br>Found<br>C, 54.63<br>H, 6.07<br>N, 5.48 |
| 92 | MeNH—(CH$_2$)$_5$—[5-chloro-2-hydroxyphenyl]-CONH-CH(CH$_2$Ph)-COOMe · HCl | DMSO-d$_6$<br>1.36(2H, m)<br>1.45–1.65(4H, m)<br>2.49(3H, s)<br>2.82(2H, t, J=7 Hz)<br>2.83(2H, m)<br>3.15(2H, m)<br>3.64(3H, s)<br>4.74(1H, m)<br>6.92(1H, s)<br>7.16–7.31(5H, m)<br>7.93(1H, s)<br>8.76(2H, brs)<br>9.05(1H, d, J=8 Hz)<br>12.01(1H, s) | | 433 (free base, MH$^+$) | |

TABLE 49

| Ex. No. | Compound | $^1$H-NMR δ (ppm), 300 MHz | IR (cm$^{-1}$) | FAB-MS | Elemental analysis (%) |
|---|---|---|---|---|---|
| 93 | MeNH—(CH$_2$)$_5$—[5-chloro-2-hydroxyphenyl]-CONH-CH(CH$_2$Ph)-COOEt · HCl | CDCl$_3$<br>1.28(3H, t, J=7.2 Hz)<br>1.40–1.51(2H, m)<br>1.57–1.67(2H, m)<br>1.84–1.95(2H, m)<br>2.62–2.68(5H, m)<br>2.88–3.01(2H, m)<br>3.16–3.29(2H, m)<br>4.24(2H, q, J=7.2 Hz)<br>4.99(1H, ddd, J=6.2, 6.2, 7.5 Hz)<br>6.77(1H, m)<br>7.17–7.33(6H, m)<br>7.35(1H, s)<br>9.41(2H, brs)<br>11.67(1H, brs) | KBr<br>3422<br>2940<br>1738<br>1644<br>1538<br>1484<br>1407<br>1373<br>1207<br>1096<br>1027<br>700 | 447 (free base, MH$^+$) | |
| 94 | Me$_2$N—(CH$_2$)$_5$—[5-chloro-2-hydroxyphenyl]-CONH-CH(CH$_2$Ph)-COOEt · HCl | CDCl$_3$<br>1.27(3H, t, J=7.1 Hz)<br>1.34–1.46(2H, m)<br>1.61–1.71(2H, m)<br>1.83–1.94(2H, m)<br>2.69(2H, t, J=7.5 Hz)<br>2.78(3H, s)<br>2.79(3H, s)<br>2.92–3.00(2H, m)<br>3.18–3.30(2H, m)<br>4.22(2H, q, J=7.1 Hz)<br>4.99(1H, ddd, J=6.0, 6.0, 7.2 Hz)<br>6.88(1H, s)<br>7.12–7.18(3H, m)<br>7.23–7.34(3H, m)<br>7.42(3H, s)<br>11.60(1H, brs)<br>12.26(1H, brs) | KBr<br>3423<br>2941<br>2693<br>1739<br>1644<br>1539<br>1483<br>1405<br>1372<br>1212<br>1095<br>1029<br>957<br>862<br>749<br>703 | 461 (free base, MH$^+$) | |

TABLE 50

| Ex. No. | Compound | $^1$H-NMR δ (ppm), 300 MHz | IR (cm$^{-1}$) | FAB-MS | Elemental analysis (%) |
|---|---|---|---|---|---|
| 95 | MeNH—(CH$_2$)$_5$—[aryl: OH, Br, CONH-CH(CH$_2$Ph)-COOMe] ·HCl | CDCl$_3$<br>1.4–1.6(4H, m)<br>1.90(2H, m)<br>2.50–2.66(5H, m)<br>2.94(2H, t, J=7.5 Hz)<br>3.20(2H, m)<br>5.02(1H, s)<br>6.77(1H, s)<br>7.16–7.36(6H, m)<br>7.54(1H, s)<br>9.38(2H, brs)<br>11.57(1H, brs) | KBr<br>3375<br>1744<br>1641<br>1604<br>1540 | 477 (free base, MH$^+$) | |
| 96 | MeNH—(CH$_2$)$_5$—[aryl: Br, OH, Br, CONH-CH(CH$_2$Ph)-COOMe] ·HCl | CDCl$_3$<br>1.47–1.60(4H, m)<br>1.96(2H, m)<br>2.68(3H, s)<br>2.94(4H, m)<br>3.24(2H, dt, J=7.8, 6.3 Hz)<br>3.80(3H, s)<br>5.05(1H, q, J=6.9 Hz)<br>7.14–7.34(6H, m)<br>7.50(1H, s) | | 557 (free base, MH$^+$) | |

TABLE 51

| Ex. No. | Compound | $^1$H-NMR δ (ppm), 300 MHz | IR (cm$^{-1}$) | FAB-MS | Elemental analysis (%) |
|---|---|---|---|---|---|
| 97 | MeNH—(CH$_2$)$_5$—[aryl: OH, C(=O)Me, CONH-CH(CH$_2$Ph)-COOMe] ·HCl | CDCl$_3$<br>1.45(2H, m)<br>1.55(2H, m)<br>1.87(2H, m)<br>2.46(3H, s)<br>2.67(3H, s)<br>2.80(2H, m)<br>2.94(2H, m)<br>3.19(1H, dd, J=14, 7 Hz)<br>3.30(1H, dd, J=14, 5 Hz)<br>3.80(3H, s)<br>5.00(1H, ddd, J=8, 7, 5 Hz)<br>6.74(1H, s)<br>7.16–7.34(5H, m)<br>7.83(1H, d, J=8 Hz)<br>7.93(1H, s)<br>9.31(2H, brs)<br>11.84(1H, brs) | | 441 (free base, MH$^+$) | |
| 98 | MeNH—(CH$_2$)$_5$—[aryl: Cl, OH, Cl, CONH-CH(CH$_2$Ph)-COOCH$_2$COOEt] ·HCl | DMSO-d$_6$<br>1.19(3H, t, J=7 Hz)<br>1.30–1.63(6H, m)<br>2.85–2.90(5H, m)<br>3.17(1H, dd, J=14, 11 Hz)<br>3.21(1H, dd, J=14, 5 Hz)<br>4.14(2H, q, J=7 Hz)<br>4.77(2H, q, J=16 Hz)<br>4.88(1H, m)<br>7.17–7.34(5H, m)<br>8.13(1H, s)<br>8.60(2H, brs)<br>9.55(1H, d, J=8 Hz)<br>13.14(1H, s) | | 539 (free base, MH$^+$) | |

TABLE 52

| Ex. No. | Compound | $^1$H-NMR δ (ppm), 300 MHz | IR (cm$^{-1}$) | FAB-MS | Elemental analysis (%) |
|---|---|---|---|---|---|
| 99 | 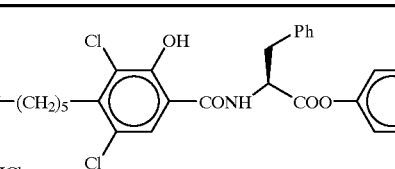 ·HCl | CDCl$_3$<br>1.38(3H, t, J=6.9 Hz)<br>1.40–2.0(6H, m)<br>2.65(3H, s)<br>2.80–3.00(4H, m)<br>3.38(2H, d, J=6.3 Hz)<br>4.37(2H, q, J=7.0 Hz)<br>5.22(2H, q, J=7.2 Hz)<br>7.08(2H, d, J=8.7 Hz)<br>7.23–7.38(7H, m)<br>8.07(2H, d, J=8.9 Hz)<br>9.44(2H, brs) | | 601<br>(free base,<br>MH$^+$) | |
| 100 | 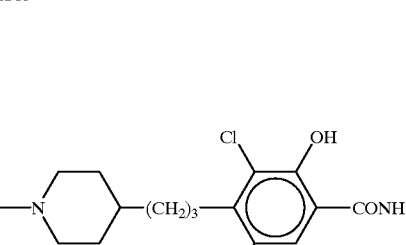 ·HCl | DMSO-d$_6$<br>1.13(3H, t, J=9 Hz)<br>1.20–1.60(7H, m)<br>1.80–1.87(2H, m)<br>2.70(3H, s)<br>2.80–2.95(4H, m)<br>3.10–3.40(4H, m)<br>4.11(2H, q, J=9 Hz)<br>4.70(1H, m)<br>7.18–7.30(5H, m)<br>8.11(1H, s)<br>9.47(1H, d, J=8 Hz)<br>9.75(1H, brs)<br>13.15(1H, brs) | | 521<br>(free base,<br>MH$^+$) | |

TABLE 53

| Ex. No. | Compound | $^1$H-NMR δ (ppm), 300 MHz | IR (cm$^{-1}$) | FAB-MS | Elemental analysis (%) |
|---|---|---|---|---|---|
| 101 | 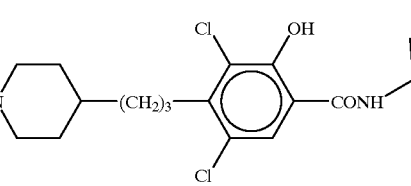 ·HCl | DMSO-d$_6$<br>1.15(3H, t, J=7.0 Hz)<br>1.20–1.40(4H, m)<br>1.45–1.65(3H, m)<br>1.73–1.85(2H, m)<br>2.51(2H, s)<br>2.70–2.90(2H, m)<br>3.10–3.30(4H, m)<br>4.11(2H, q, J=7.0 Hz)<br>4.72(1H, dd, J=6.0, 14.0 Hz)<br>7.15–7.30(5H, m)<br>8.13(1H, s)<br>8.87(1H, brs)<br>9.49(1H, brd, J=6.0 Hz)<br>13.2(1H, brs) | | 507<br>(free base,<br>MH$^+$) | |
| 102 | 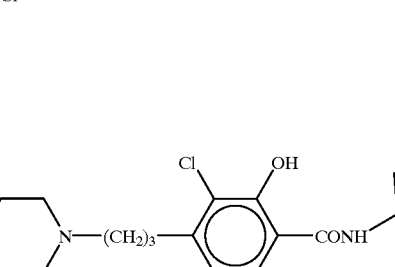 ·2HCl | 1.12(3H, t, J=7.1 Hz)<br>1.95(2H, brs)<br>2.92(2H, t, J=7.5 Hz)<br>3.09–3.78(12H, m)<br>4.10(2H, q, J=7.1 Hz)<br>4.71(1H, ddd, J=6.0, 7.2, 9.3 Hz)<br>7.17–7.28(5H, m)<br>8.16(1H, s)<br>9.51(1H, d, J=7.2 Hz)<br>9.64(2H, brs)<br>11.79(1H, brs)<br>13.20(1H, brs) | KBr<br>3396<br>2933<br>2656<br>1734<br>1644<br>1589<br>1543<br>1455<br>1405<br>1372<br>1254<br>1214<br>1099<br>1014<br>701 | 508.0<br>(free base,<br>MH$^+$) | |

TABLE 54

| Ex. No. | Compound | $^1$H-NMR δ (ppm), 300 MHz | IR (cm$^{-1}$) | FAB-MS | Elemental analysis (%) |
|---|---|---|---|---|---|
| 103 | 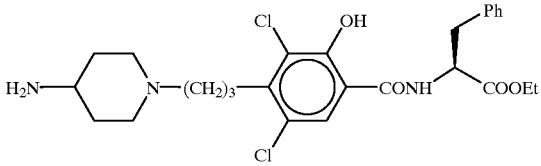 ·2HCl | DMSO-d$_6$<br>1.13(3H, t, J=7.2 Hz)<br>1.77–2.12(6H, m)<br>2.85–3.27(7H, m)<br>3.48(1H, brd, J=8.6 Hz)<br>4.10(2H, q, J=7.2 Hz)<br>4.67–4.78(1H, m)<br>7.19–7.28(5H, m)<br>8.15(1H, s)<br>8.22(3H, brs)<br>9.49(1H, brd, J=7.1 Hz)<br>10.27(1H, brs)<br>13.22(1H, brs) | | 522.1 (free base, MH$^+$) | |
| 104 | 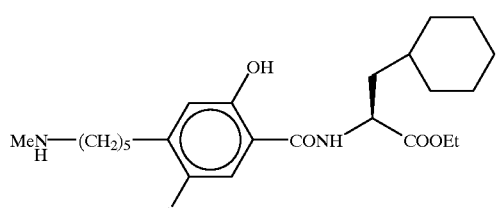 ·HCl | CDCl$_3$<br>0.90–2.05(20H, m)<br>2.50–2.70(5H, m)<br>2.96(2H, m)<br>3.82(1H, s)<br>4.82(1H, m)<br>6.68(1H, s)<br>7.45(1H, s)<br>7.52(1H, d, J=8.1 Hz) | | 439 (free base, MH$^+$) | |

TABLE 55

| Ex. No. | Compound | $^1$H-NMR δ (ppm), 300 MHz | IR (cm$^{-1}$) | FAB-MS | Elemental analysis (%) |
|---|---|---|---|---|---|
| 105 | 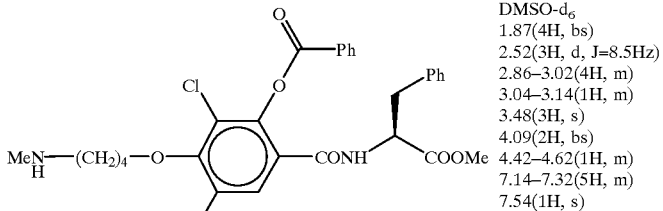 ·HCl | DMSO-d$_6$<br>1.87(4H, bs)<br>2.52(3H, d, J=8.5Hz)<br>2.86–3.02(4H, m)<br>3.04–3.14(1H, m)<br>3.48(3H, s)<br>4.09(2H, bs)<br>4.42–4.62(1H, m)<br>7.14–7.32(5H, m)<br>7.54(1H, s)<br>7.56–7.68(2H, m)<br>7.72–7.82(1H, m)<br>8.02(2H, d, J=7.6Hz)<br>9.04(1H, d, J=7.6Hz) | | 568 (free base, MH$^+$) | |
| 106 | 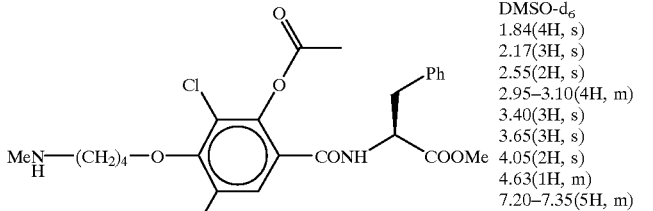 ·HCl | DMSO-d$_6$<br>1.84(4H, s)<br>2.17(3H, s)<br>2.55(2H, s)<br>2.95–3.10(4H, m)<br>3.40(3H, s)<br>3.65(3H, s)<br>4.05(2H, s)<br>4.63(1H, m)<br>7.20–7.35(5H, m)<br>7.50(1H, s)<br>8.66(1H, brs)<br>8.91(1H, d, J=9.0Hz) | | 511 (free base, MH$^+$) | |

TABLE 56

| Ex. No. | Compound | $^1$H-NMR δ (ppm), 300 MHz | IR (cm$^{-1}$) | FAB-MS | Elemental analysis (%) |
|---|---|---|---|---|---|
| 107 | [structure with isobutyryl ester, Ph, Cl, Cl, MeNH—(CH$_2$)$_4$—O—, CONH, COOMe; •HCl] | DMSO-d$_6$<br>1.15(3H, d, 6.0Hz)<br>1.17(3H, d, J=6.0Hz)<br>1.40–1.90(4H, m)<br>2.50–2.58(3H, m)<br>2.65–2.73(1H, m)<br>2.90–3.17(3H, m)<br>3.63(3H, s)<br>4.00–4.05(2H, m)<br>4.55–4.62(1H, m)<br>7.20–7.33(5H, m)<br>7.44(1H, s)<br>8.70–8.85(2H, m)<br>8.95(1H, d, J=7.0Hz) | KBr<br>3285<br>2950<br>2723<br>1768<br>1745<br>1648 | 539<br>(free base, MH$^+$) | C$_{26}$H$_{32}$Cl$_2$N$_2$O$_6$•HCl<br>Calculated<br>C, 54.22<br>H, 5.78<br>N, 4.66<br>Found<br>C, 54.24<br>H, 5.75<br>N, 4.83 |
| 108 | [structure with pivaloyl ester, Ph, Cl, Cl, MeNH—(CH$_2$)$_4$—O—, CONH, COOMe; •HCl] | DMSO-d$_6$<br>1.22(9H, s)<br>1.78–1.90(4H, m)<br>2.53(3H, m)<br>2.90–3.03(3H, m)<br>3.13(1H, dd, J=13.82, 5.53Hz)<br>3.62(3H, s)<br>4.00–4.08(2H, m)<br>4.53–4.60(1H, m)<br>7.20–7.32(5H, m)<br>7.38(1H, s)<br>8.82(2H, brs)<br>8.97(1H, d, J=7.80Hz) | Neat<br>2957<br>1749<br>1666<br>1456 | 553<br>(free base, MH$^+$) | |

TABLE 57

| Ex. No. | Compound | $^1$H-NMR δ (ppm), 300 MHz | IR (cm$^{-1}$) | FAB-MS | Elemental analysis (%) |
|---|---|---|---|---|---|
| 109 | [structure with —(CH$_2$)$_2$NH$_2$ ester, Ph, Cl, Cl, MeNH—(CH$_2$)$_4$—O—, CONH, COOMe; •2HCl] | DMSO-d$_6$<br>1.90–1.97(4H, m)<br>2.53(3H, t, J=6Hz)<br>2.99–3.12(7H, m)<br>3.16(1H, dd, J=12, 6Hz)<br>3.66(3H, s)<br>4.00–4.10(2H, m)<br>4.56–4.65(1H, m)<br>7.20–7.34(5H, m)<br>7.57(1H, s)<br>8.12(3H, brs)<br>8.88(2H, brs)<br>9.08(1H, d, J=6Hz) | KBr<br>3422<br>2954<br>1741<br>1646<br>1456 | 540<br>(free base, MH$^+$) | |
| 110 | [structure with CH$_2$OAc ester, Ph, Cl, Cl, MeNH—(CH$_2$)$_4$—O—, CONH, COOMe; •HCl] | DMSO-d$_6$<br>1.84(4H, bs)<br>2.11(3H, s)<br>2.49(2H, bs)<br>2.88–3.22(4H, m)<br>3.63(3H, s)<br>4.05(2H, bs)<br>4.52–4.68(1H, m)<br>4.82(2H, bs)<br>7.12–7.34(5H, m)<br>7.54(1H, s)<br>8.85(2H, br)<br>8.99(1H, d, J=7.6Hz) | | 571<br>(free base, M$^+$H) | |

TABLE 58

| Ex. No. | Compound | $^1$H-NMR δ (ppm), 300 MHz | IR (cm$^{-1}$) | FAB-MS | Elemental analysis (%) |
|---|---|---|---|---|---|
| 111 | [structure with MeNH-(CH$_2$)$_4$-O- dichlorophenyl, -O-C(O)-(CH$_2$)$_2$COOBn, -CONH-CH(CH$_2$Ph)-COOMe, ·HCl] | DMSO-d$_6$<br>1.89–1.96(4H, m)<br>2.54(3H, brs)<br>2.65–2.82(4H, m)<br>2.90–3.05(3H, m)<br>3.14(1H, dd, J=15.3Hz)<br>3.62(3H, s)<br>4.00–4.08(2H, m)<br>4.57–4.65(1H, m)<br>5.12(2H, s)<br>7.18–7.04(10H, m)<br>7.50(1H, s)<br>8.77(2H, brs)<br>8.94(1H, d, J=9Hz) | Neat<br>2954<br>2728<br>1778<br>1739<br>1667 | 659<br>(free base, MH$^+$) | |
| 112 | [structure with MeNH-(CH$_2$)$_4$-O- dichlorophenyl, -O-C(O)-cyclohexyl, -CONH-CH(CH$_2$Ph)-COOMe, ·HCl] | DMSO-d$_6$<br>1.1–1.9(14H, m)<br>2.49–2.51(1H, m)<br>2.54(3H, s)<br>2.93–3.17(4H, m)<br>3.63(3H, s)<br>4.0–4.10(2H, m)<br>4.55–4.15(1H, m)<br>7.23–7.32(5H, m)<br>7.44(1H, s)<br>8.72(1H, brs)<br>8.95(1H, d, J=7.0Hz) | KBr<br>3422<br>2935<br>1745<br>1654<br>1452 | 579<br>(free base, MH$^+$) | $C_{29}H_{36}Cl_2N_2O_6$·HCl<br>Calculated<br>C, 56.55<br>H, 6.05<br>N, 4.55<br>Found<br>C, 56.17<br>H, 6.16<br>N, 4.48 |

TABLE 59

| Ex. No. | Compound | $^1$H-NMR δ (ppm), 300 MHz | IR (cm$^{-1}$) | FAB-MS | Elemental analysis (%) |
|---|---|---|---|---|---|
| 113 | [structure with Me$_2$N-(CH$_2$)$_4$-O- dichlorophenyl, -O-C(O)-Ph, -CONH-CH(CH$_2$Ph)-COOMe, ·HCl] | DMSO-d$_6$<br>1.78–1.96(4H, m)<br>2.75(6H, brs)<br>2.95(1H, dd, J=15, 9Hz)<br>3.05–3.16(3H, m)<br>3.48(3H, s)<br>4.10(2H, t, J=6Hz)<br>4.48–4.56(1H, m)<br>7.17–7.29(5H, m)<br>7.49–7.65(3H, m)<br>7.73–7.81(1H, m)<br>8.00–8.05(2H, m)<br>9.04(1H, d, J=6Hz)<br>10.05(1H, brs) | Neat<br>2953<br>1747<br>1663<br>1453 | 587<br>(free base, MH$^+$) | |
| 114 | [structure with MeNH-(CH$_2$)$_4$-O- dichlorophenyl, -O-C(O)-(2-Me-phenyl), -CONH-CH(CH$_2$Ph)-COOMe, ·HCl] | DMSO-d$_6$<br>1.8–1.9(4H, m)<br>2.53(3H, s)<br>2.80–3.15(4H, m)<br>3.32(3H, s)<br>3.51(3H, s)<br>4.05–4.10(2H, m)<br>4.51–4.60(1H, m)<br>7.19–7.61(9H, m) | KBr<br>3433<br>2948<br>2719<br>1744<br>1645<br>1457 | 587<br>(free base, MH$^+$) | $C_{30}H_{32}Cl_2N_2O_6$·HCl<br>Calculated<br>C, 57.75<br>H, 5.33<br>N, 4.49<br>Found<br>C, 57.71<br>H, 5.31<br>N, 4.47 |

TABLE 60

| Ex. No. | Compound | ¹H-NMR δ (ppm), 300 MHz | IR (cm⁻¹) | FAB-MS | Elemental analysis (%) |
|---|---|---|---|---|---|
| 115 | (structure) ·HCl | DMSO-d₆ 1.76–1.94(4H, m) 2.23(3H, s) 2.30(6H, s) 2.50–2.58(3H, m) 2.86–3.03(3H, m) 3.11(1H, dd, J=13.5, 6.0Hz) 3.56(3H, s) 4.02–4.12(2H, m) 4.52–4.63(1H, m) 6.98(2H, s) 7.13–7.31(5H, m) 7.41(1H, s) 8.69(1H, brs) 9.08(1H, d, J=6.0Hz) | KBr 1748 1455 1211 1057 | 615 (free base, MH⁺) | C₃₂H₃₆Cl₂N₂O₆·HCl Calculated C, 58.95 H, 5.72 N, 4.30 Found C, 58.95 H, 5.98 N, 4.21 |
| 116 | (structure) ·HCl | DMSO-d₆ 1.26(3H, t, J=7.6Hz) 1.85(4H, bs) 2.56(3H, t, J=5.6Hz) 2.84–3.22(4H, m) 3.64(3H, s) 4.06(2H, bs) 4.22(2H, q, J=7.6Hz) 4.58–4.66(1H, m) 7.20–7.38(5H, m) 7.54(1H, s) 8.76(2H, brs) 9.01(1H, d, J=8.2Hz) | KBr 3423 2955 1774 1746 1669 1247 1215 1029 | 541 (free base, MH⁺) | |

TABLE 61

| Ex. No. | Compound | ¹H-NMR δ (ppm), 300 MHz | IR (cm⁻¹) | FAB-MS | Elemental analysis (%) |
|---|---|---|---|---|---|
| 117 | (structure) ·HCl | DMSO-d₆ 1.15(3H, t, J=6.0Hz) 1.76–1.91(4H, m) 2.17(3H, s) 2.50–2.59(3H, m) 2.90–3.07(3H, m) 3.14(1H, dd, J=6.0, 15.0Hz) 4.00–4.15(4H, m) 4.55–4.62(1H, m) 7.20–7.33(5H, m) 7.51(1H, s) 8.69(2H, brs) 8.89(1H, d, J=9.0Hz) | KBr 1646 1528 1456 1372 1190 | 525 (free base, MH⁺) | C₂₅H₃₀Cl₂N₂O₆·HCl Calculated C, 53.44 H, 5.56 N, 4.99 Found C, 52.79 H, 5.46 N, 4.94 |
| 118 | (structure) ·HCl | DMSO-d₆ 0.95–1.02(3H, d, J=6.0Hz) 1.03–1.12(3H, d, J=6.0Hz) 1.78–1.92(4H, m) 2.18(3H, s) 2.51–2.59(3H, brs) 2.39–3.17(3H, m) 3.11(1H, dd, J=13.5, 6.0Hz) 4.00–4.12(2H, m) 4.48–4.60(1H, m) 4.88(1H, tt, J=12.0, 6.0Hz) 7.19–7.36(5H, m) 7.52(1H, s) 8.74(1H, brs) 8.77(1H, d, J=9.0Hz) | KBr 1734 1655 1456 1373 1201 | 539 (free base, MH⁺) | C₂₆H₃₂Cl₂N₂O₆·HCl Calculated C, 54.22 H, 5.78 N, 4.86 Found C, 54.04 H, 5.68 N, 5.01 |

TABLE 62

| Ex. No. | Compound | $^1$H-NMR δ (ppm), 300 MHz | IR (cm$^{-1}$) | FAB-MS | Elemental analysis (%) |
|---|---|---|---|---|---|
| 119 | 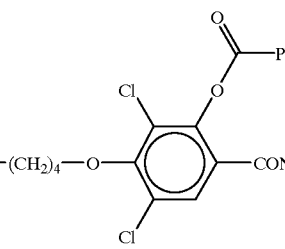 ·HCl | DMSO-d$_6$<br>1.00(3H, d, J=6Hz)<br>1.04(3H, d, J=6Hz)<br>1.75–1.90(4H, m)<br>2.82–3.09(4H, m)<br>4.05–4.12(2H, m)<br>4.40–4.50(1H, m)<br>4.70–4.85(1H, m)<br>7.05–8.05(14H, m)<br>9.02(1H, d, J=7.0Hz) | KBr<br>3420<br>2980<br>1749<br>1669<br>1522<br>1452 | 539<br>(free base, MH$^+$) | C$_{30}$H$_{32}$Cl$_2$N$_2$O$_6$·HCl<br>Calculated<br>C, 57.75<br>H, 5.33<br>N, 4.49<br>Found<br>C, 56.70<br>H, 5.21<br>N, 4.36 |
| 120 | 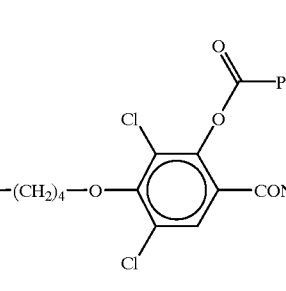 ·HCl | DMSO-d$_6$<br>1.00(3H, d, J=6Hz)<br>1.04(3H, d, J=6Hz)<br>1.80–1.93(4H, m)<br>2.54(3H, t, J=6Hz)<br>2.90–3.00(3H, m)<br>3.05(1H, dd, J=15, 6Hz)<br>4.05–4.13(2H, m)<br>4.40–4.50(1H, m)<br>4.74–4.81(1H, m)<br>7.17–7.29(5H, m)<br>7.55–7.63(3H, m)<br>7.73–7.80(1H, m)<br>8.00–8.05(2H, m)<br>8.74(2H, brs)<br>9.02(1H, d, J=9Hz) | Neat<br>2980<br>1746<br>1668<br>1453 | 601<br>(free base, MH$^+$) | |

TABLE 63

| Ex. No. | Compound | $^1$H-NMR δ (ppm), 300 MHz | IR (cm$^{-1}$) | FAB-MS | Elemental analysis (%) |
|---|---|---|---|---|---|
| 121 | 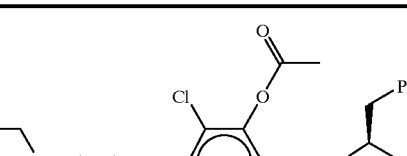 ·2HCl | DMSO-d$_6$<br>1.28(3H, d, J=6.40Hz)<br>2.17(3H, s)<br>2.90–3.90(11H, m)<br>4.38–4.40(2H, m)<br>4.45–4.61(1H, m)<br>7.15–7.30(5H, m)<br>7.52(1H, s)<br>7.75(1H, d, J=7.0Hz)<br>9.50–9.80(2H, m) | | 537<br>(free base, MH$^+$) | |
| 122 | 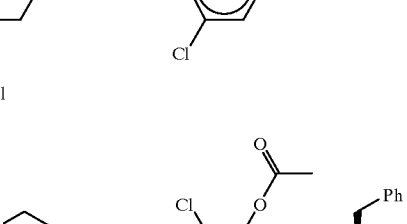 ·2HCl | DMSO-d$_6$<br>1.29(3H, d, J=6.3Hz)<br>2.18(1H, s)<br>3.02(1H, d, J=15.0, 8.5Hz)<br>3.16(1H, d, J=15.0 6.0Hz)<br>2.90–3.80(9H, m)<br>3.65(3H, s)<br>4.31–4.48(2H, m)<br>4.55–4.68(1H, m)<br>7.18–7.37(5H, m)<br>7.52(1H, s)<br>8.92(1H, d, J=14.0Hz)<br>9.58(2H, brs) | KBr<br>3422<br>1742<br>1664<br>1455<br>1368<br>1188<br>1151 | 551<br>(free base, MH$^+$) | C$_{26}$H$_{31}$Cl$_2$N$_3$O$_6$·2HCl<br>Calculated<br>C, 49.94<br>H, 5.32<br>N, 6.72<br>Found<br>48.39<br>H, 5.16<br>N, 6.46 |

TABLE 64

| Ex. No. | Compound | $^1$H-NMR δ (ppm), 300 MHz | IR (cm$^{-1}$) | FAB-MS | Elemental analysis (%) |
|---|---|---|---|---|---|
| 123 | 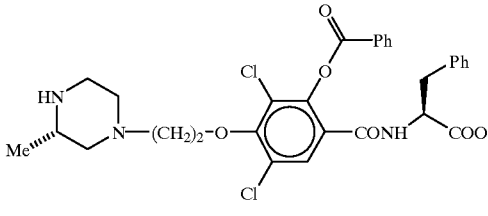 •2HCl | DMSO-d$_6$<br>1.29(3H, d, J=6.3Hz)<br>2.95(1H, dd, J=9.9, 13.8Hz)<br>3.09(1H, dd, J=9.9, 13.8Hz)<br>3.20–3.80(8H, m)<br>3.48(3H, s)<br>4.44(1H, brs)<br>4.49–4.55(2H, m)<br>7.18–7.28(5H, m)<br>7.56(1H, s)<br>7.62(2H, t, J=7.8Hz)<br>7.78(1H, t, J=7.5Hz)<br>7.53(2H, d, J=8.4Hz)<br>9.06(1H, d, J=7.8Hz) | KBr<br>3430<br>1747<br>1664 | 614<br>(free base,<br>MH$^+$) | Optical<br>rotation:<br>$[\alpha]^{25}_D =$<br>$-26.8°$<br>(c = 1.01, MeOH) |
| 124 | 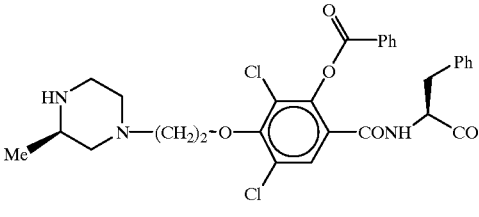 •2HCl | DMSO-d$_6$<br>1.29(3H, d, J=6.2Hz)<br>2.95(1H, dd, J=13.8, 9.8Hz)<br>3.09(1H, dd, J=13.8, 5.4Hz)<br>3.12–3.93(9H, m)<br>3.48(3H, s)<br>4.42–4.57(3H, m)<br>7.18–7.29(5H, m)<br>7.56–7.64(3H, m)<br>7.75–7.80(1H, m)<br>8.01–8.04(2H, m)<br>9.05(1H, d, J=7.8Hz)<br>9.55–9.87(2H, m) | KBr<br>3422<br>1741<br>1642<br>1585<br>1458<br>1357<br>1221 | 614<br>(free base,<br>MH$^+$) | $C_{31}H_{33}Cl_2N_3O_6$•2HCl<br>Calculated<br>C, 49.42<br>H, 5.36<br>N, 7.20<br>Found<br>48.47<br>H, 5.58<br>N, 6.91 |

TABLE 65

| Ex. No. | Compound | $^1$H-NMR δ (ppm), 300 MHz | IR (cm$^{-1}$) | FAB-MS | Elemental analysis (%) |
|---|---|---|---|---|---|
| 125 | 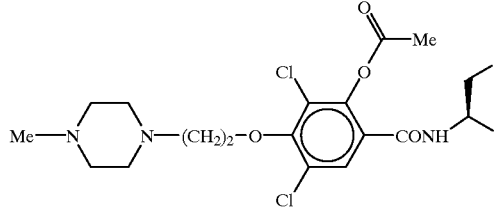 •2HCl | DMSO-d$_6$<br>1.15(3H, t, J=7.3Hz)<br>2.18(3H, s)<br>2.80(3H, s)<br>3.02(1H, dd, J=9.5, 13.8Hz)<br>3.14(1H, dd, J=5.7, 13.8Hz)<br>3.15–3.68(10H, m)<br>4.09(2H, q, J=7.3Hz)<br>4.38(2H, bs)<br>4.59(1H, ddd, J=5.7, 9.5, 7.6Hz)<br>7.23–7.33(5H, m)<br>7.53(1H, s)<br>8.91(1H, d, J=7.6Hz) | KBr<br>3433<br>2984<br>2418<br>1769<br>1735<br>1666<br>1529<br>1456<br>1378<br>1195<br>1064 | 566<br>(free base,<br>MH$^+$) | |

TABLE 66

| Ex. No. | Compound | $^1$H-NMR δ(ppm), 300MHz | IR (cm$^{-1}$) | FAB-MS | Elemental analysis (%) |
|---|---|---|---|---|---|
| 126 | MeNH—(CH$_2$)$_4$—O—[3,5-Cl$_2$,2-OH-phenyl]—CONH—CH(CH$_2$Ph)—COOH · HCl | DMSO-d$_6$<br>1.83(4H, bs)<br>2.54(3H, t, J=5.6Hz)<br>2.95(2H, bs)<br>3.08–3.78(2H, m)<br>4.05(2H, bs)<br>4.62–4.72(1H, m)<br>7.20–7.38(5H, m)<br>8.21(1H, s)<br>8.70(2H, bs)<br>9.36(1H, d, J=7.7Hz)<br>13.47(1H, s) | | 455<br>(free base,<br>MH$^+$) | |
| 127 | H$_2$N—(CH$_2$)$_4$—O—[3,5-Cl$_2$,2-OH-phenyl]—CONH—CH(CH$_2$Ph)—COOH · HCl | DMSO-d$_6$<br>1.69–1.92(4H, m)<br>2.79–2.96(2H, m)<br>3.09(1H, dd, J=15.0, 10.5Hz)<br>3.26(1H, dd, J=15.0, 6.6Hz)<br>3.96–4.11(2H, m)<br>4.63–4.77(1H, m)<br>7.13–7.35(5H, m)<br>7.86(3H, brs)<br>8.20(1H, s)<br>9.35(1H, d, J=9.0Hz)<br>12.10(1H, brs)<br>13.46(1H, s) | KBr<br>2971<br>1638<br>1585<br>1541<br>1457<br>1221 | 441<br>(free base,<br>MH$^+$) | C$_{20}$H$_{22}$Cl$_2$N$_2$O$_5$·HCl<br>Calculated<br>C, 50.27<br>H, 4.85<br>N, 5.86<br>Found<br>C, 50.22<br>H, 5.16<br>N, 5.47 |

TABLE 67

| Ex. No. | Compound | $^1$H-NMR δ(ppm), 300MHz | IR (cm$^{-1}$) | FAB-MS | Elemental analysis (%) |
|---|---|---|---|---|---|
| 128 | Me$_2$N—(CH$_2$)$_4$—O—[3,5-Cl$_2$,2-OH-phenyl]—CONH—CH(CH$_2$Ph)—COOH · HCl | DMSO-d$_6$<br>1.70–1.90(4H, m)<br>2.76(6H, s)<br>3.10–3.40(4H, m)<br>4.04–4.08(2H, t, J=7Hz)<br>4.60–4.75(1H, m)<br>7.19–7.30(5H, m)<br>8.18(1H, s)<br>9.41(1H, brs) | KBr<br>3422<br>1735<br>1638<br>1584<br>1458 | 469<br>(free base,<br>MH$^+$) | |
| 129 | 3-Me-piperazinyl—(CH$_2$)$_2$—O—[3,5-Cl$_2$,2-OH-phenyl]—CONH—CH(CH$_2$Ph)—COOH · 2HCl | CD$_3$CO$_2$D<br>1.51(3H, s)<br>3.10–3.40(2H, m)<br>3.70–4.30(9H, m)<br>4.51–4.60(2H, m)<br>5.09–5.06(2H, m)<br>7.29–7.21(5H, m)<br>7.94(1H, s) | KBr<br>3418<br>2941<br>1734<br>1641<br>1457 | 495<br>(free base,<br>MH$^+$) | C$_{23}$H$_{27}$Cl$_2$N$_3$O$_5$·2HCl<br>Calculated<br>C, 48.52<br>H, 5.13<br>N, 7.38<br>Found<br>C, 47.55<br>H, 5.02<br>N, 6.72 |

TABLE 68

| Ex. No. | Compound | ¹H-NMRδ(ppm), 300MHz | IR (cm⁻¹) | FAB-MS | Elemental analysis (%) |
|---|---|---|---|---|---|
| 130 | MeNH—(CH₂)₅—[aryl(OH, Cl)]—CONH—CH(CH₂Ph)—COOH ·HCl | DMSO-d₆<br>1.28–1.38(2H, m)<br>1.50–1.64(4H, m)<br>2.50(3H, s)<br>2.62(2H, t, J=7.5Hz)<br>2.80–2.89(2H, m)<br>3.07(1H, dd, J=8.9, 13.9Hz)<br>3.20(1H, dd, J=4.8, 13.9Hz)<br>4.69(1H, ddd, J=4.8, 7.8, 8.9Hz)<br>6.89(1H, s)<br>7.12–7.30(5H, m)<br>7.94(1H, s)<br>8.59(2H, brs)<br>8.98(1H, d, J=7.8Hz)<br>12.05(1H, brs)<br>12.98(1H, brs) | KBr<br>3368<br>2940<br>1733<br>1639<br>1543<br>1485<br>1408<br>1357<br>1258<br>1203<br>701 | 419<br>(free base, MH⁺) | |
| 131 | Me₂N—(CH₂)₅—[aryl(OH, Cl)]—CONH—CH(CH₂Ph)—COOH ·HCl | DMSO-d₆<br>1.25–1.40(2H, m)<br>1.50–1.70(4H, m)<br>2.80–2.70(8H, m)<br>2.94–3.40(4H, m)<br>4.68(1H, m)<br>6.90(1H, s)<br>7.09–7.20(5H, m)<br>7.95(1H, s)<br>8.97(1H, brs) | | 433<br>(free base MH⁺) | |

TABLE 69

| Ex. No. | Compound | ¹H-NMRδ(ppm), 300MHz | IR (cm⁻¹) | FAB-MS | Elemental analysis (%) |
|---|---|---|---|---|---|
| 132 | MeNH—(CH₂)₅—[aryl(Cl, OH, Cl)]—CONH—CH(CH₂Ph)—COOH ·HCl | DMSO-d₆<br>1.32–1.64(6H, m)<br>2.85(4H, m)<br>3.12–3.34(2H, m)<br>3.57(3H, s)<br>4.68–4.72(1H, m)<br>7.16–7.30(5H, m)<br>8.13(1H, s)<br>8.65(2H, brs)<br>9.38(1H, d, J=7.4Hz)<br>13.14(1H, brs) | | 453<br>(free base, MH⁺) | |
| 133 | Me₂N—(CH₂)₅—[aryl(Cl, OH, Cl)]—CONH—CH(CH₂Ph)—COOH ·HCl | DMSO-d₆<br>1.35(2H, m)<br>1.45–1.6(4H, m)<br>2.59(6H, s)<br>2.75(2H, m)<br>2.83(2H, m)<br>2.96(1H, dd, J=9, 14Hz)<br>3.13(1H, dd, J=5, 14Hz)<br>4.62(1H, dd, J=5, 8Hz)<br>7.15–7.2(2H, m)<br>7.2–7.3(4H, m)<br>7.60(1H, s) | | 467<br>(free base, MH⁺) | |

TABLE 70

| Ex. No. | Compound | $^1$H-NMR δ(ppm), 300MHz | IR (cm$^{-1}$) | FAB-MS | Elemental analysis (%) |
|---|---|---|---|---|---|
| 134 | 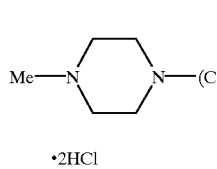 ·2HCl | DMSO-d$_6$<br>2.79(3H, s)<br>3.04–4.10(12H, m)<br>4.33(2H, brs)<br>4.70(1H, m)<br>7.17–7.30(5H, m)<br>8.21(1H, s)<br>9.36(1H, d, J=8Hz)<br>13.47(1H, brs) | | 496 (free base, MH$^+$) | |
| 135 | 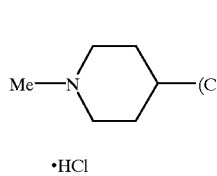 ·HCl | DMSO-d$_6$<br>1.36(2H, m)<br>1.69(2H, dd, J=6.3, 12.6Hz)<br>1.75–2.0(3H, m)<br>2.67(3H, s)<br>2.87(2H, m)<br>2.95(1H, dd, J=8.4, 14.5Hz)<br>3.11(1H, dd, J=5.4, 14.1Hz)<br>3.93(2H, t, J=6.3Hz)<br>4.64(1H, dd, J=5.7, 7.5Hz)<br>7.17–7.29(5H, m)<br>7.59(1H, s)<br>11.72(1H, brs) | | 495 (free base, MH$^+$) | |

TABLE 71

| Ex. No. | Compound | $^1$H-NMR δ(ppm), 300MHz | IR (cm$^{-1}$) | FAB-MS | Elemental analysis (%) |
|---|---|---|---|---|---|
| 136 | 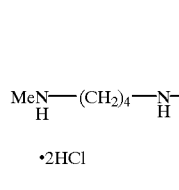 ·2HCl | DMSO-d$_6$<br>1.44–1.69(4H, m)<br>2.50–2.57(3H, m)<br>2.63–2.92(2H, m)<br>3.11(1H, dd, J=13.5, 9.0Hz)<br>3.21(1H, dd, J=13.5, 6.6Hz)<br>3.48–3.59(2H, m)<br>3.05(3H, s)<br>4.67–4.79(1H, m)<br>5.63(1H, brs)<br>7.17–7.34(5H, m)<br>8.02(1H, s)<br>8.57(2H, brs)<br>9.18(1H, d, J=9.0Hz)<br>13.43(1H, s) | | 468 (free base, MH$^+$) | |
| 137 | 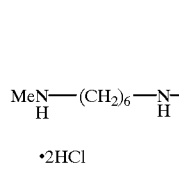 ·2HCl | DMSO-d$_6$<br>1.29–1.84(8H, m)<br>2.69(3H, s)<br>2.88–3.36(6H, m)<br>3.73(3H, s)<br>4.82–4.96(1H, m)<br>6.93(1H, d, J=8.5Hz)<br>7.18–7.34(6H, m)<br>7.93(1H, t, J=4.2Hz) | KBr<br>3422<br>2939<br>1741<br>1638<br>1542 | 428 (free base, M$^+$H) | |

TABLE 72

| Ex. No. | Compound | $^1$H-NMRδ(ppm), 300MHz | IR (cm$^{-1}$) | FAB-MS | Elemental analysis (%) |
|---|---|---|---|---|---|
| 138 | 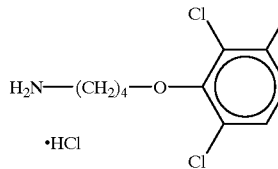 | DMSO-d$_6$<br>1.83(4H, bs)<br>2.82–2.94(2H, m)<br>3.16–3.32(2H, m)<br>4.02–4.06(2H, m)<br>4.88–5.02(1H, m)<br>7.06–7.42(8H, m)<br>7.62(2H, d, J=8.1Hz)<br>7.86(2H, bs)<br>8.32(1H, s)<br>10.38(1H, s) | KBr<br>3412<br>2954<br>1638<br>1599<br>1542<br>1445<br>1066 | 516<br>(free base, MH$^+$) | |
| 139 | 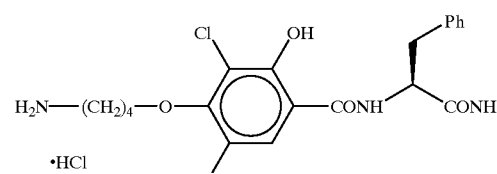 | DMSO-d$_6$<br>1.74–1.87(4H, m)<br>2.83–2.92(2H, m)<br>2.95–3.03(1H, m)<br>3.14–3.22(1H, m)<br>3.99–4.06(2H, m)<br>4.65–4.74(1H, m)<br>7.14–7.34(6H, m)<br>7.68–7.81(4H, m)<br>8.23(1H, s)<br>9.19–9.21(1H, m)<br>13.56(1H, s) | KBr<br>2955<br>1677<br>1458<br>1413<br>1352<br>1261<br>1203<br>1138 | 440<br>(free base, MH$^+$) | $C_{20}H_{23}Cl_2N_3O_4 \cdot$HCl<br>Calculated<br>C, 50.38<br>H, 5.07<br>N, 8.81<br>Found<br>C, 47.87<br>H, 4.6<br>N, 7.31 |

TABLE 73

| Ex. No. | Compound |
|---|---|
| 140 | 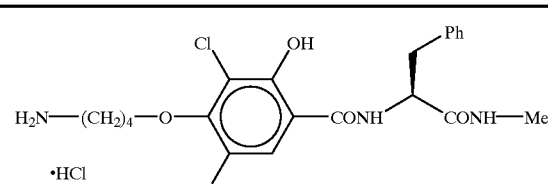 |
| 141 | 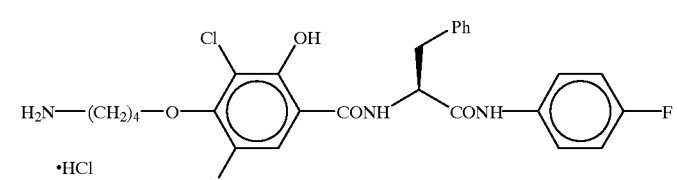 |

| Ex. No. | $^1$H-NMRδ(ppm), 300MHz | IR (cm$^{-1}$) | FAB-MS | Elemental analysis (%) |
|---|---|---|---|---|
| 140 | DMSO-d$_6$<br>1.80–1.84(4H, m)<br>2.62(3H, d, J=4.5Hz)<br>2.85–2.89(2H, m)<br>3.00(1H, dd, J=13.7, 10.8Hz)<br>3.16(1H, dd, J=13.7, 4.2Hz)<br>4.00–4.16(2H, m)<br>4.66–4.73(1H, m)<br>7.13–7.32(5H, m)<br>7.82–7.97(3H, m)<br>8.20(1H, q, J=4.5Hz)<br>8.27(1H, s)<br>9.31(1H, d, J=8.2Hz)<br>13.56(1H, s) | KBr<br>3422<br>2940<br>1641<br>1584<br>1458<br>1412<br>1348<br>1228 | 454<br>(free base, MH$^+$) | $C_{21}H_{25}Cl_2N_3O_4 \cdot$HCl<br>Calculated<br>C, 51.39<br>H, 5.34<br>N, 8.56<br>Found<br>C, 50.03<br>H, 5.38<br>N, 8.15 |

TABLE 73-continued

| | | | | |
|---|---|---|---|---|
| 141 | DMSO-$d_6$<br>1.78–1.86(4H, m)<br>2.78–2.94(2H, m)<br>3.18–3.78(2H, m)<br>4.02–4.10(2H, m)<br>4.86–4.96(1H, m)<br>7.12–7.42(8H, m)<br>7.60–7.66(2H, m)<br>7.32(2H, bs)<br>8.32(1H, s)<br>9.42(1H, d, J=8.8Hz)<br>10.44(1H, s) | KBr<br>2954<br>1670<br>1639<br>1542<br>1508<br>1217<br>1065 | 534<br>(free base,<br>MH$^+$) | |

TABLE 74

| Ex. No. | Compound | $^1$H-NMRδ(ppm), 300MHz | IR (cm$^{-1}$) | FAB-MS | Elemental analysis (%) |
|---|---|---|---|---|---|
| 142 | H$_2$N—(CH$_2$)$_4$—O—[3,5-Cl, 2-OH phenyl]—CONH—CH(CH$_2$Ph)—CONH—[2-pyridyl]<br>·2HCl | DMSO-$d_6$<br>1.73–1.88(4H, m)<br>2.79–2.92(2H, m)<br>3.08–3.30(2H, m)<br>4.01–4.07(2H, m)<br>5.02–5.32(1H, m)<br>7.17–7.21(2H, m)<br>7.26–7.31(2H, m)<br>7.45–7.47(2H, m)<br>7.84–8.08(5H, m)<br>8.30(1H, s)<br>8.37(1H, d, J=6.0Hz)<br>9.40(1H, d, J=9.0Hz)<br>11.24(1H, s)<br>13.42(1H, s) | KBr<br>3423<br>2957<br>1643<br>1572<br>1541<br>1439<br>1337<br>1260<br>1228 | 517 (free base, MH$^+$) | $C_{25}H_{26}Cl_2N_4O_4$·HCl<br>Calculated<br>C, 50.87<br>H, 4.78<br>N, 9.49<br>Found<br>C, 49.81<br>H, 5.14<br>N, 9.27 |
| 143 | MeNH—(CH$_2$)$_4$—O—[3,5-Cl, 2-OH phenyl]—CONH—CH(CH$_2$Ph)—CONHOH | DMSO-$d_6$<br>1.70–1.90(4H, m)<br>2.58(3H, s)<br>2.75–3.00(4H, m)<br>3.88–3.98(2H, m)<br>4.56–4.59(1H, m)<br>7.16–7.33(5H, m)<br>7.55(1H, s)<br>8.78(1H, m) | KBr<br>3422<br>1624<br>1570<br>1542<br>1431 | 470 (MH$^+$) | |

TABLE 75

| Ex. No. | Compound | ¹H-NMRδ(ppm), 300MHz | IR (cm⁻¹) | FAB-MS | Elemental analysis (%) |
|---|---|---|---|---|---|
| 144 | [structure: 3,5-dichloro-2-hydroxy-4-(4-aminobutoxy)-benzamide coupled to (1-benzyl-2-(3-methyl-1,2,4-oxadiazol-5-yl)ethyl) · HCl] | DMSO-d₆ 1.80–1.86(4H, m) 2.35(3H, s) 2.84–2.90(2H, m) 3.34–3.47(2H, m) 4.00–4.06(2H, m) 5.56–5.64(1H, m) 7.19–7.34(5H, m) 7.96(3H, brs) 8.22(1H, s) 9.86(1H, d, J=9Hz) 13.19(1H, brs) | KBr 3421 2935 1638 1588 1542 1457 | 479 (free base, MH⁺) | |
| 145 | [structure: 3,5-dichloro-2-hydroxy-4-(4-aminobutoxy)-benzamide coupled to (1-benzyl-3-hydroxy-propan-2-yl) · HCl] | DMSO-d₆ 1.70–1.92(4H, m) 2.73–3.01(4H, m) 3.42–3.58(2H, m) 3.95–4.11(2H, m) 4.13–4.32(1H, m) 4.97(1H, brs) 7.09–7.33(5H, m) 7.91(3H, brs) 8.25(1H, s) 8.92(1H, d, J=9.0Hz) 13.98(1H, s) | KBr 3421 2950 1637 1583 1458 | 427 (free base, MH⁺) | $C_{20}H_{24}Cl_2N_2O_4 \cdot HCl$ Calculated C, 51.80 H, 5.43 N, 6.04 Found C, 50.96 H, 5.46 N, 5.65 |

TABLE 76

| Ex. No. | Compound | ¹H-NMRδ(ppm), 300MHz | IR (cm⁻¹) | FAB-MS | Elemental analysis (%) |
|---|---|---|---|---|---|
| 146 | [structure: 3-hydroxy-6-(4-aminobutoxy)-2-naphthamide coupled to (1-benzyl-2-methoxycarbonyl-ethyl) · HCl] | DMSO-d₆ 1.58–1.82(4H, m) 2.68–2.84(2H, m) 3.02–3.26(2H, m) 3.67(3H, s) 4.12–4.20(2H, m) 4.82–4.88(1H, m) 6.92(1H, d, J=9.0Hz) 7.16–7.40(8H, m) 7.54(1H, s) 7.81(2H, br) 8.21(1H, s) 8.62(1H, d, J=7.2Hz) 10.21(1H, s) | KBr 3386 2952 1741 1647 1618 1527 1227 1188 | 437 (free base, MH⁺) | |
| 147 | [structure: 4'-(4-methylaminobutoxy)biphenyl-4-carboxamide coupled to (1-benzyl-2-ethoxycarbonyl-ethyl) · HCl] | DMSO-d₆ 1.20(3H, t, J=5.4Hz) 1.82–1.85(4H, m) 2.58–2.62(3H, m) 2.96–3.04(2H, m) 3.15–3.26(2H, m) 4.11(2H, t, J=4.3Hz) 4.16(2H, q, J=5.4Hz) 4.69–4.75(1H, m) 7.10(2H, d, J=6.6Hz) 7.24–7.28(1H, m) 7.32–7.38(4H, m) 7.73(2H, d, J=6.6Hz) 7.77(2H, d, J=6.3Hz) 7.94(2H, d, J=6.3Hz) 8.72–8.83(2H, m) 8.88(1H, d, J=5.8Hz) | KBr 3332 2938 2723 1750 1630 1605 1535 1495 1204 1183 | 475 (free base, MH⁺) | |

TABLE 77

| Ex. No. | Compound | $^1$H-NMR δ (ppm), 300 MHz | IR (cm$^{-1}$) | FAB-MS | Elemental analysis (%) |
|---|---|---|---|---|---|
| 148 | MeNH—(CH$_2$)$_4$—[oxadiazole]—[phenyl(OH)]—CONH—CH(CH$_2$Ph)—COOEt ·HCl | DMSO-d$_6$<br>1.16(3H, t, J=7Hz)<br>1.65–1.92(4H, m)<br>2.53(3H, s)<br>2.93(2H, t, J=6Hz)<br>3.07(2H, t, J=6Hz)<br>3.12–3.25(2H, m)<br>4.12(2H, t, J=7Hz)<br>7.19–7.33(5H, m)<br>7.54(1H, dd, J=3.9Hz)<br>7.59(1H, d, J=9Hz)<br>8.68(2H, brs)<br>9.08(1H, d, J=9Hz)<br>12.08(1H, brs) | KBr<br>3343<br>2936<br>1741<br>1638<br>1550 | 467<br>(free base, MH$^+$) | |
| 149 | MeNH—(CH$_2$)$_4$—[oxadiazole]—[phenyl]—CONH—CH(CH$_2$Ph)—COOEt ·HCl | DMSO-d$_6$<br>1.14(3H, t, J=6.8Hz)<br>1.66–1.82(4H, m)<br>2.42–2.58(6H, m)<br>2.84–3.22(6H, m)<br>4.09(2H, q, J=6.8Hz)<br>4.64–4.68(1H, m)<br>7.18–7.34(5H, m)<br>7.98(2H, d, J=8.6Hz)<br>8.08(2H, d, J=8.6Hz)<br>8.68(1H, br)<br>9.04(1H, d, J=7.2Hz) | KBr<br>3423<br>2938<br>1735<br>1617<br>1560<br>1211 | 451<br>(free base, MH$^+$) | |

TABLE 78

| Ex. No. | Compound | $^1$H-NMR δ (ppm), 300 MHz | IR (cm$^{-1}$) | FAB-MS | Elemental analysis (%) |
|---|---|---|---|---|---|
| 150 | MeNH—(CH$_2$)$_4$—[oxadiazole]—[phenyl(OH)]—CONH—CH(CH$_2$Ph)—COOH ·HCl | DMSO-d$_6$<br>1.70–1.88(4H, m)<br>2.53(3H, m)<br>2.90–3.70(6H, m)<br>4.76(1H, m)<br>7.20–7.28(5H, m)<br>7.55–7.56(2H, m)<br>8.04(1H, d, J=6.0Hz)<br>8.62(2H, m)<br>9.03(1H, d, J=6.0Hz)<br>12.12(1H, s)<br>13.0(1H, brs) | KBr<br>1735<br>1623<br>1545<br>1224 | 439<br>(free base, MH$^+$) | |
| 151 | MeNH—(CH$_2$)$_4$—[oxadiazole]—[phenyl(OH)]—CONH—CH(CH$_2$Ph)—[oxadiazole-Me] ·HCl | DMSO-d$_6$<br>1.69–1.88(4H, m)<br>2.34(3H, s)<br>2.53(3H, m)<br>2.89–3.80(6H, m)<br>5.62(1H, m)<br>7.20–7.32(5H, m)<br>7.52(1H, d, J=6Hz)<br>7.55(1H, s)<br>7.59(1H, d, J=6Hz)<br>8.69(2H, brs)<br>9.40(1H, d, J=6.0Hz)<br>12.06(1H, s) | KBr<br>1654<br>1542<br>1437<br>1231 | 477<br>(free base, MH$^+$) | |

TABLE 79

| Ex. No. | Compound | $^1$H-NMR δ (ppm), 300 MHz | IR (cm$^{-1}$) | FAB-MS | Elemental analysis (%) |
|---|---|---|---|---|---|
| 152 | MeNH—(CH$_2$)$_3$—S—[benzoxazole]—CONH—CH(CH$_2$Ph)—COOEt · HCl | DMSO-d$_6$<br>1.15(3H, t, J=15Hz)<br>2.18(2H, m)<br>2.57(3H, m)<br>2.90–3.50(6H, m)<br>4.12(2H, q, J=15Hz)<br>4.60(1H, m)<br>7.21–7.34(5H, m)<br>7.73(1H, d, J=9Hz)<br>7.82(1H, d, J=9Hz)<br>8.09(1H, s)<br>8.80(2H, brs)<br>8.91(1H, d, J=6Hz) | | 442 (free base, MH$^+$) | |
| 153 | MeNH—(CH$_2$)$_6$—S—[benzoxazole]—CONH—CH(CH$_2$Ph)—COOEt · HCl | DMSO-d$_6$<br>1.11–1.83(11H, m)<br>2.52(3H, m)<br>2.83–3.57(6H, m)<br>4.10(2H, q, J=18Hz)<br>4.65(1H, m)<br>7.20–7.83(7H, m)<br>8.12(1H, s)<br>8.94(3H, m) | KBr<br>1738<br>1643<br>1497<br>1469 | 484 (free base, MH$^+$) | |

TABLE 80

| Ex. No. | Compound | $^1$H-NMR δ (ppm), 300 MHz | IR (cm$^{-1}$) | FAB-MS | Elemental analysis (%) |
|---|---|---|---|---|---|
| 154 | MeNH—(CH$_2$)$_4$—S—[2-OMe-phenyl]—CONH—CH(CH$_2$Ph)—COOEt · HCl | CDCl$_3$<br>1.24(3H, t, J=7.3Hz)<br>1.70–1.83(2H, m)<br>1.97–2.08(2H, m)<br>2.65(3H, s)<br>2.92–3.02(4H, m)<br>3.21(2H, d, J=5.8Hz)<br>3.80(3H, s)<br>4.18(2H, q, J=7.3Hz)<br>5.03(1H, q, J=5.8Hz)<br>6.83(1H, d, J=1.3Hz)<br>6.93(1H, dd, J=8.2, 1.3Hz)<br>7.15–7.28(5H, m)<br>8.08(1H, d, J=8.2Hz)<br>8.27(1H, d, J=7.3Hz)<br>9.56(2H, brs) | | 445 (free base, MH$^+$) | |

TABLE 81

| Ex. No. | Compound | ¹H-NMR δ (ppm), 300 MHz | IR (cm⁻¹) | FAB-MS | Elemental analysis (%) |
|---|---|---|---|---|---|
| 155 | [Structure: HN-piperazine-N-(CH₂)₂-COO-(3,5-dichloro-4-OH-phenyl)-CONH-CH(CH₂Ph)-COOEt · 2HCl] | DMSO-$d_6$<br>1.14(3H, t, J=7Hz)<br>3.08–3.60(14H, m)<br>4.12(2H, q, J=7Hz)<br>7.15–7.32(5H, m)<br>8.31(1H, s)<br>9.58(1H, d, J=9Hz)<br>9.59(2H, brs) | KBr<br>3436<br>1774<br>1638<br>1459 | 538<br>(free base, MH⁺) | |
| 156 | [Structure: HN-(4-Et-piperidine)-COO-(5-Cl-2-OH-phenyl)-CONH-CH(CH₂Ph)-COOEt · HCl] | DMSO-$d_6$<br>0.93(3H, t, J=6.0Hz)<br>1.17(3H, t, J=6.0Hz)<br>1.66–1.92(4H, m)<br>2.22–2.34(2H, m)<br>2.78–3.36(6H, m)<br>4.11(2H, q, J=6.0Hz)<br>4.70–4.78(1H, m)<br>6.98(1H, s)<br>7.24–7.32(5H, m)<br>8.11(1H, s)<br>8.89(1H, brs)<br>9.08(1H, d, J=7.2Hz)<br>12.37(1H, s) | KBr<br>3342<br>2972<br>1738<br>1651<br>1262<br>1182 | 503<br>(free base, MH⁺) | |

TABLE 82

| Ex. No. | Compound | ¹H-NMR δ (ppm), 300 MHz | IR (cm⁻¹) | FAB-MS | Elemental analysis (%) |
|---|---|---|---|---|---|
| 157 | [Structure: MeNH-(CH₂)₃-COO-(2-OH-phenyl)-CONH-CH(CH₂Ph)-COOMe · HCl] | CDCl₃<br>2.20–2.34(2H, m)<br>2.71(3H, s)<br>2.77(2H, t, J=5Hz)<br>3.11(2H, brs)<br>3.23(2H, ddd, J=13, 8, 5Hz)<br>3.77(3H, s)<br>5.01(1H, ddd, J=8, 8, 5Hz)<br>6.60(1H, dd, J=9, 2Hz)<br>6.73(1H, d, J=2Hz)<br>6.97(1H, d, J=8Hz)<br>7.13(2H, dd, J=8, 2Hz)<br>7.24–7.32(3H, m)<br>7.37(1H, d, J=9Hz)<br>9.51(2H, brs)<br>12.12(1H, s) | | 415<br>(free base, MH⁺) | |
| 158 | [Structure: MeNH-(CH₂)₃-COO-(5-Br-2-OH-phenyl)-CONH-CH(CH₂Ph)-COOMe · HCl] | CDCl₃<br>2.20–2.40(2H, m)<br>2.71–2.85(4H, m)<br>3.05–3.25(4H, m)<br>3.77(1H, s)<br>4.9(1H, q, J=7.2Hz)<br>6.86(1H, s)<br>7.14–7.30(6H, m)<br>7.67(1H, s)<br>9.43(2H, brs)<br>11.91(1H, s) | | 493<br>(free base, MH⁺) | |

Formulation Examples of the pharmaceutical agents containing the compound of the present invention are shown in the following.

| Formulation Example 1 (Tablet) | |
|---|---|
| (1) Compound of Example 18 | 10 g |
| (2) Lactose | 50 g |
| (3) Corn starch | 15 g |
| (4) Carboxymethylcellulose sodium | 44 g |

| Formulation Example 1 (Tablet) | |
|---|---|
| (5) Magnesium stearate | 1 g |

The entire amounts of (1), (2) and (3), and 30 g of (4) were kneaded with water, dried in vacuo, and granulated. The granules were added with 14 g of (4) and 1 g of (5), and the mixture was compressed to give tablets, whereby 1,000 tablets containing 10 mg of the compound per tablet were prepared.

FORMULATION EXAMPLE 2
(Injection)

The compound of Example 18 (100 mg) was dissolved in an aqueous solution of mannitol (5 g) dissolved in water (100 ml) for injection, sterilized by filtration through a 0.22 μm filter, and filled in sterilized ampoules by 1 ml to give injections containing 1 mg of the compound per ampoule.

The results of experiments with respect to the suppression of production of inflammatory cytokines, suppression of LPS-induced peritonitis and suppression of LPS/D-glactosamine-induced hepatitis by the compound of the present invention are shown below.

EXPERIMENTAL EXAMPLE 1
Suppression of production of inflammatory cytokines

Thirty ml of human peripheral blood added with heparin was placed on Ficol-Paque (15 ml), and centrifuged at 400 G for 40 minutes at room temperature. The obtained monocyte fraction layers were collected and washed three times with E-MEM medium. The cells were adjusted to a final concentration of $0.5 \times 10^5$ cells/800 μl with RPMI-1640 medium containing 5% bovine fetal serum (2-mercaptoethanol), and seeded in a 24 well plate by 800 μl. A test sample (100 μl) was added and 100 μl of lipopolysarcharide (LPS, 100 μg/ml) was added one hour later. The supernatant was taken at 20 hours after stimulation with LPS, and amounts of various cytokines were determined using an ELISA kit. By plotting the cytokine amounts at various concentrations, the concentration of the test sample necessary for inhibition by 50% ($IC_{50}$) was determined. The results are shown in Tables 83–88.

TABLE 83

| | $IC_{50}$ (μM) | | |
|---|---|---|---|
| | IL-1β | TNF | IL-8 |
| Example No. 1 | 0.002 | 0.008 | 0.009 |
| Example No. 2 | — | — | 0.01 |
| Example No. 3 | >30 | 14 | >30 |
| Example No. 4 | 3 | 2 | 2 |
| Example No. 5 | 75 | 6 | 6 |
| Example No. 6 | 14 | 6 | 14 |
| Example No. 7 | — | — | 8 |
| Example No. 9 | — | — | <0.3 |
| Example No. 10 | — | — | 0.6 |
| Example No. 11 | — | — | 0.4 |
| Example No. 14 | — | — | 1 |
| Example No. 15 | — | — | 1 |
| Example No. 16 | — | — | 0.03 |
| Example No. 18 | — | — | <0.01 |
| Example No. 19 | — | — | <0.01 |
| Example No. 20 | — | — | 29 |
| Example No. 21 | — | — | <0.01 |
| Example No. 22 | — | — | <0.01 |
| Example No. 24 | — | — | 0.02 |

TABLE 83-continued

| | $IC_{50}$ (μM) | | |
|---|---|---|---|
| | IL-1β | TNF | IL-8 |
| Example No. 25 | — | — | 0.01 |
| Example No. 26 | — | — | 0.009 |

TABLE 84

| | $IC_{50}$ (μM) | | |
|---|---|---|---|
| | IL-1β | TNF | IL-8 |
| Example No. 27 | — | — | <0.01 |
| Example No. 28 | — | — | <0.01 |
| Example No. 29 | — | — | <0.01 |
| Example No. 30 | — | — | 0.6 |
| Example No. 31 | — | — | <0.01 |
| Example No. 32 | — | — | 0.5 |
| Example No. 34 | — | — | 2 |
| Example No. 36 | — | — | 0.06 |
| Example No. 37 | — | — | 0.3 |
| Example No. 39 | — | — | 0.02 |
| Example No. 40 | — | — | 0.01 |
| Example No. 41 | — | — | <0.01 |
| Example No. 42 | — | — | 0.1 |
| Example No. 43 | — | — | 0.03 |
| Example No. 44 | — | — | <0.01 |
| Example No. 45 | 0.0008 | 0.004 | 0.004 |
| Example No. 46 | — | — | <0.01 |
| Example No. 47 | — | — | 3 |
| Example No. 48 | — | — | 0.2 |
| Example No. 49 | — | — | 0.02 |
| Example No. 50 | — | — | 28 |

TABLE 85

| | $IC_{50}$ (μM) | | |
|---|---|---|---|
| | IL-1β | TNF | IL-8 |
| Example No. 51 | — | — | 7 |
| Example No. 52 | — | — | <0.01 |
| Example No. 53 | — | — | <0.01 |
| Example No. 54 | — | — | <0.01 |
| Example No. 55 | — | — | <0.01 |
| Example No. 56 | — | — | 4 |
| Example No. 57 | — | — | 0.05 |
| Example No. 58 | — | — | 0.02 |
| Example No. 60 | — | — | 0.03 |
| Example No. 63 | — | — | 0.1 |
| Example No. 64 | — | — | 0.05 |
| Example No. 67 | — | — | 0.05 |
| Example No. 68 | — | — | 0.001 |
| Example No. 69 | — | — | <0.001 |
| Example No. 70 | — | — | 0.006 |
| Example No. 71 | — | — | 0.04 |
| Example No. 72 | — | — | 0.1 |
| Example No. 73 | — | — | <0.01 |
| Example No. 74 | — | — | 0.07 |
| Example No. 75 | — | — | 0.04 |
| Example No. 76 | — | — | 0.3 |

TABLE 86

| | $IC_{50}$ (μM) | | |
|---|---|---|---|
| | IL-1β | TNF | IL-8 |
| Example No. 77 | — | — | 3 |
| Example No. 80 | — | — | 3 |
| Example No. 81 | — | — | 4 |

TABLE 86-continued

| | IC$_{50}$ ($\mu$M) | | |
|---|---|---|---|
| | IL-1β | TNF | IL-8 |
| Example No. 82 | — | — | 0.02 |
| Example No. 83 | — | — | 0.09 |
| Example No. 84 | — | — | 0.03 |
| Example No. 85 | — | — | 0.07 |
| Example No. 86 | — | — | <0.001 |
| Example No. 87 | — | — | 0.2 |
| Example No. 88 | — | — | 3 |
| Example No. 89 | — | — | 0.6 |
| Example No. 90 | — | — | 0.6 |
| Example No. 91 | — | — | 0.001 |
| Example No. 92 | — | — | 0.03 |
| Example No. 94 | — | — | 1 |
| Example No. 95 | — | — | 0.09 |
| Example No. 96 | — | — | 0.003 |
| Example No. 98 | — | — | 0.001 |
| Example No. 99 | — | — | 0.001 |
| Example No. 100 | — | — | 0.001 |
| Example No. 101 | — | — | 0.003 |

TABLE 87

| | IC$_{50}$ ($\mu$M) | | |
|---|---|---|---|
| | IL-1β | TNF | IL-8 |
| Example No. 102 | — | — | 0.002 |
| Example No. 103 | — | — | 0.7 |
| Example No. 104 | — | — | 0.7 |
| Example No. 105 | 0.001 | 0.004 | 0.005 |
| Example No. 106 | — | — | <0.01 |
| Example No. 110 | — | — | <0.01 |
| Example No. 111 | — | — | <0.01 |
| Example No. 117 | — | — | <0.01 |
| Example No. 122 | — | — | <0.01 |
| Example No. 125 | — | — | 0.01 |
| Example No. 126 | — | — | 0.8 |
| Example No. 127 | — | — | 0.2 |
| Example No. 128 | — | — | 0.2 |
| Example No. 129 | — | — | 2 |
| Example No. 132 | — | — | 0.07 |
| Example No. 133 | — | — | 0.2 |
| Example No. 134 | — | — | 0.2 |
| Example No. 136 | — | — | 0.2 |
| Example No. 137 | — | — | 2 |
| Example No. 138 | — | — | 1 |
| Example No. 139 | — | — | 4 |

TABLE 88

| | IC$_{50}$ ($\mu$M) | | |
|---|---|---|---|
| | IL-1β | TNF | IL-8 |
| Example No. 140 | — | — | 13 |
| Example No. 141 | — | — | 3 |
| Example No. 142 | — | — | 0.4 |
| Example No. 143 | — | — | 3 |
| Example No. 144 | — | — | 29 |
| Example No. 146 | — | — | 5 |
| Example No. 147 | — | — | 2 |
| Example No. 148 | — | — | 4 |
| Example No. 149 | — | — | 3 |
| Example No. 152 | — | — | 7 |
| Example No. 153 | — | — | 1 |
| Example No. 155 | — | — | 0.2 |
| Example No. 156 | — | — | 2 |

EXPERIMENTAL EXAMPLE 2
Suppression of LPS-induced peritonitis

LPS (30 $\mu$g/ml, 1 ml) prepared with physiological saline containing 0.5% CMC (carboxymethylcellulose) was intraperitoneally injected into male Balb/c mice to induce-peritonitis. One hour later, the mice were killed with carbon dioxide, and the amount of TNF α in the peritoneal fluid was determined using an ELISA kit.

The test sample (50 mg/kg) was administered from the tail vein at 60 minutes before LPS injection, and the degree of suppression was investigated. The suppression by the test sample is shown in the ratio relative to the suppression in the control group.

Suppression (%)=100−(TNF amount of group treated with test sample/TNF amount of control group)×100

The results are shown in Table 89 wherein ** means the presence of significant difference by p<0.01 from the control group.

TABLE 89

| | Inhibition (%) |
|---|---|
| Example No. 1 | 64** |
| Example No. 4 | 38** |
| Example No. 9 | 21 |
| Example No. 19 | 32** |
| Example No. 51 | 38** |
| Example No. 52 | 31** |
| Example No. 148 | 19 |
| Example No. 155 | 28** |

EXPERIMENTAL EXAMPLE 3

Suppression of LPS/D-galactosamine-induced hepatitis

LPS (5 $\mu$g/kg)/D-galactosamine (500 mg/kg) in physiological saline was intraperitoneally injected to male C57BL/6 mice to induce hepatitis. Six hours after the injection of LPS/D-galactosamine in physiological saline, blood was taken from the mice orbital venosus plexus. Plasma was separated from the blood, and ALT in blood was determined by a biochemical analyzer. The test sample was administered from the tail vein at 10 minutes before the injection of LPS/D-galactosamine in physiological saline, and the degree of suppression was investigated. The suppression by the test sample is shown in the ratio relative to the suppression in the control group.

Suppression (%)=100−(ALT amount of group treated with test sample/ALT amount of control group)×100

The results are shown in Tables 90–91.

TABLE 90

| | Dose (mg/kg) | Inhibition (%) |
|---|---|---|
| Example No. 1 | 5 | 88 |
| | 10 | 78 |
| Example No. 2 | 10 | 65 |
| Example No. 4 | 10 | 42 |
| Example No. 10 | 10 | 77 |
| Example No. 18 | 10 | 86 |
| Example No. 22 | 10 | 51 |
| Example No. 24 | 10 | 63 |
| Example No. 27 | 10 | 67 |
| Example No. 31 | 5 | 87 |
| Example No. 32 | 10 | 78 |
| Example No. 36 | 10 | 47 |
| Example No. 37 | 10 | 80 |

TABLE 91

| | Dose (mg/kg) | Inhibition (%) |
|---|---|---|
| Example No. 40 | 10 | 49 |
| Example No. 45 | 10 | 30 |
| Example No. 46 | 10 | 57 |
| Example No. 50 | 10 | 15 |
| Example No. 54 | 5 | 74 |
| Example No. 60 | 10 | 42 |
| Example No. 61 | 10 | 6 |
| Example No. 105 | 10 | 40 |
| Example No. 117 | 10 | 54 |
| Example No. 123 | 10 | 41 |
| Example No. 126 | 10 | 27 |
| Example No. 127 | 5 | 82 |
| Example No. 138 | 5 | 22 |

From the foregoing results, it is evident that the compound of the present invention suppresses production of inflammatory cytokines and is useful for the prophylaxis and therapy of noninfectious or infectious diseases accompanied by neutrophile migration, which are represented by rheumatic diseases (e.g., rheumatoid arthritis); arthritis due to gout; systemic lupus erythematosus; dermatopathy (e.g., psoriasis, pustulosis and atopic dermatitis); respiratory diseases (e.g., bronchial asthma, bronchitis, ARDS and diffused interstitial pneumonia); inflammatory bowel diseases (e.g., ulcerative colitis and Crohn's disease); acute or chronic hepatitis inclusive of fulminant hepatitis; acute or chronic glomerulonephritis; nephropyelitis; uveitis caused by Behcet disease and vogt-Koyanagi Harada disease; Mediterranean fever (polyserositis); ischemic diseases (e.g., myocardial infarction); and systemic circulatory failure and multiorgan failure caused by sepsis.

The test results with respect to inflammatory cytokines such as IL-6 and GM-CSF have confirmed suppression of these inflammatory cytokines by the compound of the present invention.

What is claimed is:

1. An amide compound of the formula (I):

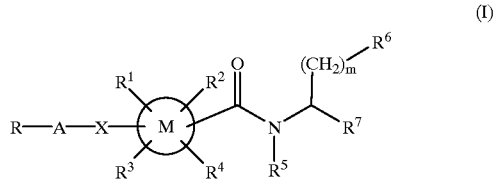

wherein;

R is a piperazinyl optionally substituted by lower alkyl, a piperidyl optionally substituted by lower alkyl or an amino
    wherein amino is optionally substituted by lower alkyl;
A is a linear alkylene;
X is an oxygen atom, a sulfur atom, —NH— or —CH$_2$—;
M is an arylene;
$R^1$, $R^2$, $R^3$ and $R^4$ are the same or different and each is a hydrogen atom, provided at least one of $R^1$, $R^2$, $R^3$ and $R^4$ is not a hydrogen atom, a hydroxy, a halogen atom, or —O—CO—$R^{11''''}$ wherein $R^{11''''}$ is lower alkyl optionally substituted by a substituent selected from the group consisting of amino, acyloxy and benzyloxycarbonyl, or phenyl optionally substituted by lower alkyl;
$R^5$ is a hydrogen atom;
m is 1;
$R^6$ is a phenyl and
$R^7$ is —COO—$R^{12''''}$
    wherein $R^{12''''}$ is hydrogen atom, aralkyl, adamantyl, cyclohexylideneamino,
    cyclohexyl optionally substituted by lower alkyl, piperidyl optionally substituted by lower alkyl, or alkyl optionally substituted by a substituent selected from the group consisting of hydroxy, lower alkoxy, lower alkoxy lower alkoxy, lower alkoxycarbonyl, acyloxy, piperazinyl and amino optionally substituted by lower alkyl;
or a pharmaceutically acceptable acid addition salt thereof.

2. The amide compound of claim 1, wherein H is phenylene, or a pharmaceutically acceptable acid addition salt thereof.

3. The amide compound of claim 1, wherein $R^7$ is —COO—$R^{12''''}$ wherein $R^{12''''}$ is lower alkyl, or cyclohexyl which is optionally substituted by lower alkyl, or a pharmaceutically acceptable acid addition salt thereof.

4. The amide compound of claim 1, wherein X is an oxygen atom or —CH$_2$—, or a pharmaceutically acceptable acid addition salt thereof.

5. The amide compound of claim 1, wherein $R^6$ is phenyl and m is 1, or a pharmaceutically acceptable acid addition salt thereof.

6. The amide compound of claim 1, wherein $R^1$, $R^2$, $R^3$ and $R^4$ are the same or different and each is a hydrogen atom provided that at least one of $R^1$, $R^2$, $R^3$ and $R^4$ is not a hydrogen atom, hydroxy, a halogen atom, or —O—CO—$R^{11''''}$ wherein $R^{11''''}$ is lower alkyl or phenyl, or a pharmaceutically acceptable acid addition salt thereof.

7. A pharmaceutical composition comprising a pharmaceutically acceptable carrier, and the amide compound of any one of claims 1 to 6 or a pharmaceutically acceptable acid addition salt thereof.

8. A method for suppressing the production of cytokines, comprising administering to a patient in need thereof, an inflammatory cytokine production suppressor comprising an amide compound of any one of claims 1 to 6 or a pharmaceutically acceptable acid addition salt thereof as an active ingredient.

9. A method for treating or prophylaxis of inflammatory diseases, comprising administering to a patient in need thereof, an agent for treating or prophylaxis of inflammatory diseases comprising an amide compound of any one of claims 1 to 6 or a pharmaceutically acceptable acid addition salt thereof as an active ingredient.

* * * * *